(12) United States Patent
Horiuchi

(10) Patent No.: US 7,504,537 B2
(45) Date of Patent: Mar. 17, 2009

(54) HYDROXAMIC ACID DERIVATIVE AND MMP INHIBITOR CONTAINING THE SAME AS ACTIVE INGREDIENT

(75) Inventor: Yoshihiro Horiuchi, Osaka (JP)

(73) Assignee: Dainippon Sumitomo Pharma Co., Ltd., Osaka-Fu (JP)

( * ) Notice: Subject to any disclaimer, the term of this patent is extended or adjusted under 35 U.S.C. 154(b) by 725 days.

(21) Appl. No.: 10/500,218

(22) PCT Filed: Dec. 26, 2002

(86) PCT No.: PCT/JP02/13580

§ 371 (c)(1),
(2), (4) Date: Jun. 25, 2004

(87) PCT Pub. No.: WO03/055851

PCT Pub. Date: Jul. 10, 2003

(65) Prior Publication Data

US 2005/0282905 A1 Dec. 22, 2005

(30) Foreign Application Priority Data

Dec. 27, 2001 (JP) .............................. 2001-397638

(51) Int. Cl.
*C07C 259/04* (2006.01)
(52) U.S. Cl. ..................................................... 562/621
(58) Field of Classification Search ................ 562/621
See application file for complete search history.

(56) References Cited

U.S. PATENT DOCUMENTS 5,817,404 A 10/1998 Kawakita et al.
5,863,949 A 1/1999 Robinson et al.
5,932,595 A 8/1999 Bender et al.
6,087,359 A 7/2000 Getman et al.
6,087,392 A 7/2000 Reiter
6,107,337 A 8/2000 Robinson
6,153,609 A 11/2000 Robinson et al.
6,156,798 A 12/2000 Reiter
6,303,636 B1 10/2001 Robinson, Jr. et al.
6,417,229 B1 7/2002 Sahagan et al.
6,673,804 B1 1/2004 Kimura et al.
6,713,477 B1 3/2004 Scarlato et al.

FOREIGN PATENT DOCUMENTS

| EP | 0895988 | 2/1999 |
| WO | 98/43963 | 10/1998 |
| WO | 98/50348 | 12/1998 |
| WO | 00/63165 | 10/2000 |
| WO | 00/63197 | 10/2000 |
| WO | 00/71514 | 11/2000 |

*Primary Examiner*—Taylor Victor Oh
(74) *Attorney, Agent, or Firm*—Wenderoth, Lind & Ponack, LLP

(57) ABSTRACT

A hydroxamic acid derivative represented by the following general formula (1) having selective MMP inhibitory activity,

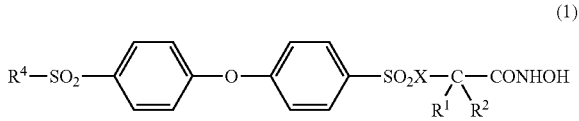

(1)

wherein $R^1$ and $R^2$ each represents hydrogen atom, lower alkyl group, lower haloalkyl etc., X represents methylene group or $NR^3$ ($R^3$ represents hydrogen atom, lower alkyl group, etc.), and $R^4$ represents C1~4 lower alkyl group.

13 Claims, No Drawings

HYDROXAMIC ACID DERIVATIVE AND MMP INHIBITOR CONTAINING THE SAME AS ACTIVE INGREDIENT

This application is a U.S. national stage of International application No. PCT/JP02/13580 filed Dec. 26, 2002.

TECHNICAL FIELD

The present invention relates to a hydroxamic acid derivative having matrix metalloproteinases (abbreviated as MMP hereinafter) inhibiting activity and a medicament containing the said derivative as an active ingredient.

BACKGROUND ART

MMP are proteolytic enzymes which play very important roles in various physiological processes, such as procreation, proliferation, differentiation, etc. Many functions of MMP are controlled by tissue inhibitors of metalloproteinases (TIMPs) under the normal physiological conditions.

MMP have a metal such as zinc in the active center, and there are known a sub-family consisting of 18 kinds (MMP-1, MMP-2, MMP-3, MMP-7, MMP-8, MMP-9, MMP-10, MMP-11, MMP-12, MMP-13, MMP-14, MMP-15, MMP-16, MMP-17, MMP-19, MMP-20, MMP-23 and MMP-24).

Recently it has been elucidated that when the functions of MMP are abnormally promoted, the function can not be controlled by TIMPs in the living body to cause various diseases. For example, in case of diseases relating to bone or cartilage, such as rheumatoid arthritis, osteoarthritis, etc., the amounts of glycoprotein and collagen in articular cartilage decrease due to the abnormal promotion of MMP (J. Trzaskos, et al., Acta Onthopaedica Scandinavica, 66, 150 (1995)). MMP are said to play the important roles in appearance of arteriosclerosis or re-stricturization (re-stenochoria) of post angiopoietic operation (C. M. Dollery et al., Cric Res., 77, 863 (1995)). Furthermore, MMP are known to be highly expressed in several tissues such as in mastocarcinoma tissue and therefore, it is strongly indicated that there is a possibility that MMP play the important roles in proliferation or metastasis (J. M. P. Freije et al., Journal of Biological Chemistry, Vol. 269, 16766-16773, (1994)). MMP are observed also in fibroblast isolated from the gums having inflammation (J. Periodontal Res., 16, 417-424 (1981)).

In addition, an enzyme which convert TNFα which is an exacerbation factor of inflammatory diseases from the latent type to the expression type, namely TNF converting enzyme (TACE) (Nature, 370, 555-557 (1994)), aggrecanase, and so on are within the category of MMP.

Among MMP, MMP-13 is an enzyme which localizes in joints together with aggrecanase which proteolyses aggrecan which is a main component of articular cartilage, and that shows potent proteolytic activity against collagen II which is another main component of cartilage. It is reported that MMP-13 is over-expressed in cartilage of a patient suffering from osteoarthritis (Mitchell, et al., J. Clin. Invest., 97, 761 (1996)). Such an over-expression is also observed in joints of patients suffering from bone arthritis and rheumatoid arthritis. Therefore, MMP-13 is considered as a factor relating to cartilage and bone-absorption, and it is expected that the therapeutic method by using an inhibitor of MMP-13 becomes an etiomatic therapy.

Namely, a compound inhibiting MMP-13 is considered to be useful as a prophylactic or therapeutic treating agent for arthritis such as osteoarthritis, rheumatoid, etc., and as an inhibitor of metastasis, invasion, or proliferation of various cells.

On the other hand, non-steroidal anti-inflammatory drugs (NSAID) are broadly used for treatment of osteoarthritis and rheumatoid arthritis. However, such a treatment is a symptomatic therapy, and it is desired to develop a medicament useful for etiomatic treatment such as to inhibit the progress of the diseases.

As mentioned above, it is considered that MMP inhibitors are effective for treatment and prophylaxis of the above diseases, as the promotion of the functions of MMP cause to various diseases.

As MMP inhibitors, there are reported arylsulfonamide derivatives having hydroxamic acid and so on. For example, in WO 97/27174, hydroxamic acid derivatives of α-amino acid are disclosed. In WO 99/51572 and U.S. Pat. No. 6,107,337, hydroxamic acid derivatives of α-amino acid having phenoxyphenyl as a partial structure are disclosed.

However, no compound having 4-(4-alkylsulfonylphenoxy)phenyl sulfonamide as a partial structure has been reported.

In regard to MMP inhibitors, clinical trials have been done on various compounds on cancer, rheumatoid arthritis, osteoarthritis, etc., but it is reported that many of these compounds caused side effects such as pains at skeletal muscles or joints.

MMP inhibition, such as MMP-1, MMP-14 (MT1-MMP) inhibition, is paid attention as these causes (Gendai-iryo, 32, 931 (2000), Protein, Nucleic acid and Enzyme, 45, 1083 (2000)). Among MMP knockout mice, MMP-9 and MMP-14 knockout mice indicate osteopsathyrosis. Especially, in the case of MMP-14 knockout mice, it is considered that the phenotype showed hypometabolism of connective tissue due to decrease or loss of collagen degradation ability in growth after the birth (Kenn Holmbedk et al., Cell, 99, 81-92 (1999)). Namely, it is suggested that in case of remodeling of bone or cartilage tissue the decrease or loss of collagen degradation ability occurs, and it is considered to greatly participate in the said side effect.

Therefore, it is desired to develop a MMP inhibitor having no side effects as mentioned above.

DISCLOSURE OF INVENTION

The present invention is to provide a compound which inhibits MMP-3 and/or MMP-13 selectively, and a medicament containing as an active ingredient, a MMP inhibitor which inhibits MMP-3 and/or MMP-13 selectively and has the reduced side effect.

The present inventors have considered that by evaluating on the selective inhibition between MMP-3 and/or MMP-13, and MMP-14 and MMP-1, and furthermore, MMP-2 and/or MMP-9, separation between the main activity and the side effect may be made large and the side effect may be reduced. Especially as they have considered that the causes of the side effect to skeletal muscles or joints consist in inhibition of MMP-14, they have extensively studied to find the compounds which do not inhibit MMP-14, and inhibit MMP-13 selectively. As a result, they have found that a novel hydroxamic acid derivative having 4-(4-alkyl sulfonylphenoxy)phenyl group, represented by a following general formula (1) has not only an excellent MMP-13 inhibiting activity, but also is extremely low in MMP-9 and MMP-14 inhibiting activity.

They have also found that a compound represented by a general formula (2) mentioned below, which is known as a MMP inhibitor(WO 00/63197), is not selective to MMP-1 and MMP-14.

The present invention has been completed based on the above findings.

In the present specification, "not selective to MMP-1 and/or MMP-14" means that inhibition activity to MMP-1 and/or MMP-14 is extremely low or there is no inhibiting activity to MMP-1 and/or MMP-14. Illustratively, it means that the 50% inhibition rate ($IC_{50}$) or Ki value of the compound to MMP-1 and/or MMP-14 is extremely small comparing with the 50% inhibiting rate or Ki value to MMP-13 and/or MMP-3.

"Non selective to MMP-14" means that the ratio of $IC_{50}$ to MMP-14 per $IC_{50}$ to MMP-13 is preferably more than 50, more preferably more than 100, and most preferably more than 300.

"Non selective to MMP-1" means that the ratio of $IC_{50}$ to MMP-1 per $IC_{50}$ to MMP-13 is preferably more than 100, more preferably more than 300, and most preferably more than 1000.

BEST MODE FOR CARRYING OUT THE INVENTION

The present invention relates to a hydroxamic acid derivative, a pharmaceutically acceptable salt thereof or a prodrug thereof, which is represented by the following formula (1),

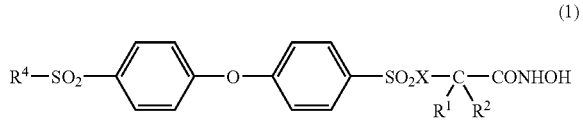

(1)

, wherein $R^1$ and $R^2$ are each independently hydrogen atom, optionally substituted lower alkyl group, or lower haloalkyl group, or $R^1$ and $R^2$ are bound together to form C2~7 straight alkylene group, or a group represented by a formula, —$(CH_2)_m$-Y—$(CH_2)_q$- (wherein Y is —O—, —$NR^5$—, —S—, —SO—, or —$SO_2$—, m and q are each independently an integer of 1 to 5, and the total of m and q are 2~6, and $R^5$ is hydrogen atom, optionally substituted lower alkyl group, optionally substituted lower alkyl carbonyl group, optionally substituted lower alkoxycarbonyl group, optionally substituted lower alkylsulfonyl group, optionally substituted sulfamoyl group or optionally substituted carbamoyl group), X is methylene group or $NR^3$ (wherein $R^3$ is hydrogen atom, or optionally substituted lower alkyl group, or $R^3$ is bound with $R^1$ together with their binding N atom and carbon atom to form optionally substituted heterocycloalkane.), and $R^4$ is C1~4 lower alkyl group.

In the present invention, the lower alkyl group is C1~5 saturated straight or branched alkyl group. For example, methyl group, ethyl group, propyl group, 1-methylethyl group, butyl group, 1-methylpropyl group, 2-methylpropyl group, 1,1-dimethylethyl group, pentyl group, and 2,2-dimethylpropyl group are illustrated.

The lower alkoxy group is a group formed by binding the above lower alkyl group with oxygen atom, such as methoxy group, ethoxy group, propoxy group, 1-methylethoxy group, butoxy group, 1-methylpropoxy group, 2-methylpropoxy group, 1,1-dimethylethoxy group, pentyloxy group, 2,2-dimethylpropoxy group, etc.

The lower alkylthio group is a group formed by binding the above lower alkyl group with sulfur atom, such as methylthio group, ethylthio group, propylthio group, 1-methylethylthio group, butylthio group, 1-methylpropylthio group, 2-methylpropylthio group, 1,1-dimethylethylthio group, pentylthio group, 2,2-dimethylpropylthio group, etc.

The lower alkylsulfinyl group is a group formed by binding the above lower alkyl group with sulfinyl, such as methylsulfinyl group, ethylsulfinyl group, propylsulfinyl group, 1-methylethylsulfinyl group, butylsulfinyl group, 1-methylpropylsulfinyl group, 2-methylpropylsulfinyl group, 1,1-dimethylethylsulfinyl group, pentylsulfinyl group, 2,2-dimethylpropylsulfinyl group, etc.

The lower alkylsulfonyl group is a group formed by binding the above lower alkyl group with sulfonyl, such as methylsulfonyl group, ethylsulfonyl group, propylsulfonyl group, 1-methylethylsulfonyl group, butylsulfonyl group, 1-methylpropylsulfonyl group, 2-methylpropylsulfonyl group, 1,1-dimethylethylsulfonyl group, pentylsulfonyl group, 2,2-dimethylpropylsulfonyl group, etc.

The lower alkylcarbonyl group is a group formed by binding the above lower alkyl group with carbonyl, such as acetyl group, propanoyl group, butanoyl group, 2-methylpropanoyl group, pentanoyl group, 2,2-dimethylpropanoyl group, etc.

The lower alkylcarbonyloxy group is a group formed by binding the above lower alkyl carbonyl group with oxygen atom, such as acetyloxy group, propanoyloxy group, butanoyloxy group, 2-methylpropanoyloxy group, pentanoyloxy group, 2,2-dimethylpropanoyloxy group, etc.

The lower alkoxycarbonyl group is a group formed by binding the above lower alkoxy group with carbonyl, such as methoxycarbonyl group, ethoxycarbonyl group, propoxycarbonyl group, 1-methylethoxycarbonyl group, butoxycarbonyl group, 1-methylpropoxycarbonyl group, 2-methylpropoxycarbonyl group, 1,1-dimethylethoxycarbonyl group, pentyloxycarbonyl group, 2,2-dimethylpropoxycarbonyl group, etc.

The halogen atom is fluorine atom, chlorine atom, bromine atom, or iodine atom, preferably fluorine atom or chlorine atom, and more preferably, fluorine atom.

The lower haloalkyl group is the above lower alkyl group substituted by 1 to 5 halogen atoms, such as trifluoromethyl group, pentafluoroethyl group, difluoromethyl group, 2,2,2-trifluoroethyl group, 2,2-difluoroethyl group, etc.

The lower haloalkoxy group is the above lower alkoxy group substituted by 1 to 5 halogen atoms, such as trifluoromethoxy group, pentafluoroethoxy group, difluoromethoxy group, 2,2,2-trifluoroethoxy group, 2,2-difluoroethoxy group, etc.

The C2~7 straight alkylene group includes ethylene, propylene, tetramethylene, pentamethylene, hexamethylene, heptamethylene, etc.

The lower cycloalkyl group includes cyclopropyl group, cyclobutyl group, cyclopentyl group, cyclohexyl group, etc.

The lower cycloalkoxy group is a group formed by binding the above lower cycloalkyl group with oxygen atom, such as cyclopropoxy group, cyclobutoxy group, cyclopentyloxy group, cyclohexyloxy group, etc.

The heterocycloalkane includes 4 to 7 membered heterocycloalkane containing at least one nitrogen atom and a nitrogen atom, an oxygen atom or a sulfur atom, and when the said heterocycloalkane contains sulfur atom, the said sulfur atom may be oxidized by 1 or 2 oxygen atoms.

The said heterocycloalkane includes azetidine, pyrrolidine, piperidine, piperazine, morpholine, thiomorpholine, thiomorpholine oxide, thiomorpholine dioxide, perhydroazepine, etc.

The aryl group includes phenyl group, naphthyl group, etc.

The aryloxy group is a group formed by binding the above aryl group with oxygen atom, such as phenoxy group, 1-naphtoxy group, 2-naphthoxy group, etc.

The arylthio group is a group formed by binding the above aryl group with sulfur atom.

The arylsulfonyl group is a group formed by binding the above aryl group with sulfonyl.

The arylcarbonyl group is a group formed by binding the above aryl group with carbonyl.

The arylcarbamoyl group is a group formed by binding the above aryl group with carbamoyl.

The heteroaryl group is mono or di cyclic heteroaryl group containing therein 1 to 3 heteroatoms selected from 0~3 nitrogen atoms, 0 or 1 oxygen atom, and 0 or 1 sulfur atom, such as furyl group, thienyl group, pyrrolyl group, azepinyl group, pirazolyl group, imidazolyl group, oxazolyl group, isoxazolyl group, thiazolyl group, isothiazolyl group, 1,2,4-thiadiazolyl group, 1,2,4-oxadiazolyl group, triazolyl group, thiadiazolyl group, pyranyl group, pyridyl group, pyridazinyl group, pyrimidyl group, pyrazinyl group, indolyl group, benzothienyl group, benzofuryl group, quinolyl group, isoquinolyl group, quinazolinyl group, quinoxalinyl group, etc.

The heteroaryloxy group is a group formed by binding the above heteroaryl group with oxygen atom via a carbon atom of the said heteroaryl group.

The heteroarylthio group is a group formed by binding the above heteroaryl group with sulfur atom via a carbon atom of the said heteroaryl group.

The heteroarylsulfonyl group is a group formed by binding the above heteroaryl group with sulfonyl via a carbon atom of the said heteroaryl group.

The heteroarylcarbonyl group is a group formed by binding the above heteroaryl group with carbonyl via a carbon atom of the said heteroaryl group.

The heteroarylcarbamoyl group is a group formed by binding the above heteroaryl group with carbamoyl via a carbon atom of the said heteroaryl group.

When in the present invention, aryl group, aryloxy group, arylthio group, arylcarbonyl group, arylcarbamoyl group, arylsulfonyl group, heteroaryl group, heteroaryloxy group, heteroarylthio group, heteroarylcarbonyl group, heteroarylcarbamoyl group, and heteroarylsulfonyl group have a substituent(s), the said substituent may be substituted by the same or different, and the number of the said substituents are 1 to 3. The said substituent includes the following a)~f):

a) Halogen atom, cyano group, hydroxy group, carboxy group, lower haloalkyl group, lower haloalkoxy group.

b) Lower alkoxy group, lower alkylthio group, lower alkylsulfinyl group, lower alkylsulfonyl group, lower cycloalkyl group, lower alkoxycarbonyl group.

c) —CONR$^{11}$R$^{12}$, —SO$_2$NR$^{11}$R$^{12}$, wherein R$^{11}$ and R$^{12}$ are each independently, hydrogen atom, lower alkyl group, or lower alkyl group substituted by lower alkoxy group, or —NR$^{11}$R$^{12}$ is a structure selected from the group consisting of the following formulas,

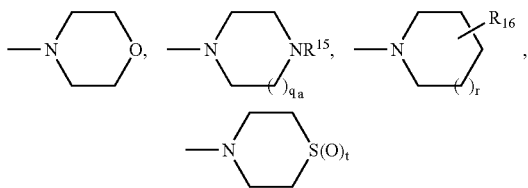

(wherein q$_a$ is an integer of 1 or 2, r is an integer of 0~2, t is an integer of 0~2, R$^{15}$ is lower alkyl group, lower alkylcarbonyl group, lower alkylsulfonyl group, or lower alkoxycarbonyl group, and R$^{16}$ is carboxy group, hydroxy group, lower alkoxy group, lower alkylcarbonyloxy group, lower alkylcarbonyl group, lower alkoxycarbonyl group, or carbamoyl group optionally substituted by 1 to 2 lower alkyl groups.).

d) —NR$^{13}$COR$^{14}$, —NR$^{13}$SO$_2$R$^{14}$, wherein R$^{13}$ and R$^{14}$ are each independently, hydrogen atom, or lower alkyl group.

e) —NR$^{17}$R$^{18}$, wherein R$^{17}$ is hydrogen atom or lower alkyl group, and R$^{18}$ is hydrogen atom, lower alkyl group, lower alkylcarbonyl group, lower alkoxycarbonyl group, or lower alkylsulfonyl group.

f) Non-substituted lower alkyl group, or lower alkyl group substituted by 1 to 3 substituent groups mentioned below. The said substituent group is lower alkoxy group, lower alkylthio group, lower alkylsulfinyl group, lower alkylsulfonyl group, lower alkylcarbonyl group, lower alkoxycarbonyl group, lower alkylcarbonyloxy group, cyano group, carboxy group, hydroxy group, —NR$^{17}$R$^{18}$ (wherein R$^{17}$ and R$^{18}$ are the same as defined above.), —CONR$^{11}$R$^{12}$, —SO$_2$NR$^{11}$R$^{12}$ (wherein R$^{11}$ and R$^{12}$ are the same as defined above.), —NR$^{13}$COR$^{14}$, or —NR$^{13}$SO$_2$R$^{14}$ (wherein R$^{13}$ and R$^{14}$ are the same as defined above.).

When in the present specification, lower alkyl groups in R$^1$ and R$^2$ have a substituent(s), the said substituent(s) are the same or different, and one or more. The said substituent includes halogen atom, hydroxy group, cyano group, lower alkoxy group, lower alkylthio group, lower alkylsulfinyl group, lower alkylsulfonyl group, lower cycloalkyl group, optionally substituted aryl group, optionally substituted heteroaryl group, optionally substituted aryloxy group, optionally substituted heteroaryloxy group, optionally substituted arylthio group, optionally substituted heteroarylthio group, optionally substituted arylsulfonyl group, optionally substituted heteroarylsulfonyl group, —NR$^{17}$R$^{18}$ (wherein R$^{17}$ and R$^{18}$ are the same as defined above.).

When lower alkyl group in R$^3$ has a substituent(s), the said substituent(s) are the same or different and the number of the said substituents are 1 to 3, and the said substituent group is illustrated as the following a)~f):

a) Carboxy group, hydroxy group, lower haloalkyl group, lower haloalkoxy group, cyano group.

b) Lower alkylcarbonyl group, lower alkylcarbonyloxy group, lower alkoxycarbonyl group.

c) —CONR$^{11}$R$^{12}$ group, —SO$_2$NR$^{11}$R$^{12}$ group, —NHCONR$^{11}$R$^{12}$ group, wherein R$^{11}$ and R$^{12}$ are the same as defined above.

d) —NR$^{13}$COR$^{14}$, —NR$^{13}$SO$_2$R$^{14}$, wherein R$^{13}$ and R$^{14}$ are the same as defined above.

e) Aryl group, heteroaryl group, aryloxy group, heteroaryloxy group, arylthio group, arylcarbonyl group, heteroarylcarbonyl group, heteroarylthio group, arylsulfonyl group, heteroarylsulfonyl group, and each group is optionally substituted (The said heteroaryl is preferably furyl and thienyl.), f) Lower alkoxy group, lower alkylthio group, lower alkylsulfinyl group, lower alkylsulfonyl group, and each group is optionally substituted by the same or different and 1 to 3 substituents. (The said substituent includes optionally substituted aryl group, optionally substituted heteroaryl group, lower alkoxy group, carbamoyl group substituted by 1 or 2 lower alkyl groups, and carbamoyl group substituted by lower cycloalkyl group. The said heteroaryl is preferably furyl and thienyl.)

When heterocycloalkane which R$^3$ forms together with R$^1$ with N atom and carbon atom which are binding has a substituent(s), the said substituents are the same or different, and 1 to 4 The said substituent group is illustrated as the following a) or b).

a) In case of the substituent being bound to carbon atom: hydroxy group, carboxy group, lower alkyl group, lower alkoxy group, lower alkoxycarbonyl group.

b) In case of the substituent being bound to nitrogen atom: lower alkyl group, lower alkoxycarbonyl group, lower alkylcarbonyl group, lower alkylsulfonyl group, and each group is respectively optionally substituted (The substituent on the said substituent group includes lower alkoxy group, optionally substituted aryl group, and optionally substituted heteroaryl group.);

Arylcarbonyl group, heteroarylcarbonyl group, and arylcarbamoyl group, and each group is optionally substituted (The substituent is the same as the substituent on the above aryl group.);

—$CONR^{11}R^{12}$, —$SO_2NR^{11}R^{12}$, wherein $R^{11}$ and $R^{12}$ are each independently hydrogen atom, lower alkyl group, lower alkyl group substituted by lower alkoxy group, and —$NR^{11}R^{12}$ is a structure selected from the group consisting of the following structures,

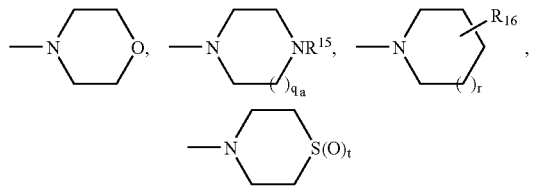

(wherein $q_a$, r, t, $R^{15}$ and $R^{16}$ are the same as defined above.)

The heteroaryl in the above heteroaryl group and the above heteroarylcarbonyl group is preferably furyl or thienyl. Or two substituents on adjacent two carbon atoms on the said heterocycloalkane may be bound to form optionally substituted benzene ring or an optionally substituted 5 to 6 membered monocyclic aromatic ring. The said 5 to 6 membered monocyclic aromatic ring includes a 5 to 6 membered monocyclic aromatic ring containing 1 or 2 hereroatoms selected from 1~2 nitrogen atom, an oxygen atom, and a sulfur atom, such as pyridine ring, pyrimidine ring, thiophen ring, or furan ring. The substituent on the above benzene ring and the above monocyclic heteroaromatic ring is the same as one on aryl group.

When lower alkyl group, lower alkylcarbonyl group, lower alkoxycarbonyl group, or lower alkylsulfonyl group in $R^5$ has a substituent(s), the substituents are the same or different and 1 to 3, and the said substituent includes lower alkoxy group, lower cycloalkoxy group and aryloxy group.

When carbamoyl group and sulfamoyl group in $R^5$ has a substituent(s), the substituents are the same or different and 1 to 2, and the said substituent includes lower alkyl group and lower alkoxy group and the said two substituents may bind with the adjacent nitrogen atom to form a structure selected from the group of the following structures:

-continued

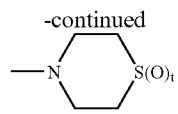

wherein $q_a$, r, t, $R^{15}$ and $R^{16}$ are the same as defined above.

One of the preferable embodiments of $R^1$ and $R^2$ in the general formula (1) of the present invention is the same each other, and hydrogen atom or lower alkyl group, more preferably hydrogen atom or C1~3 lower alkyl group. It is also a preferable embodiment that $R^1$ and $R^2$ are bound together to form C3~5 alkylene group, or $R^1$ and $R^2$ are bound to form —$(CH_2)$m-Y—$(CH_2)$q- (wherein both m and q are 2). It is also a preferable embodiment when Y is —S— or —O— in the above formula.

When Y is —$NR^5$—, the substituent on lower alkyl group, lower alkylcarbonyl group, lower alkylsulfonyl group, or lower alkoxycarbonyl group in $R^5$ includes the same as one on lower alkyl in the above $R^3$. The substituent on carbamoyl group in $R^5$ includes the same as $R^{11}$ and $R^{12}$ in the above —$CONR^{11}R^{12}$.

In addition, it is one of the most preferable embodiments when either $R^1$ or $R^2$ is hydrogen atom and the other is lower alkyl group, such as ethyl group, 1-methylethyl group, propyl group, 2-methylpropyl group, etc. In this case, the configuration of the carbon atom to which $R^1$ and $R^2$ are bound is preferably D configuration (In the present specification, the expression of the D configuration is accordance with Fisher's projection.).

$R^3$ is preferably, hydrogen atom, C1~4 lower alkyl group, or C1~4 lower alkyl group substituted by a group selected from the group consisting of carboxy group, phenyl group (the said phenyl group may be substituted by lower alkyl group, lower alkoxy group or halogen atom.), 2-pyridyl group, 3-pyridyl group, 4-pyridyl group (the said pyridyl group may be substituted by lower alkyl group.), C1~5 lower alkoxycarbonyl group and lower alkoxy group, such as hydrogen atom, methyl, ethyl, isobutyl, methoxyethyl, isopropoxyethyl, ethoxyethyl, methoxypropyl, carboxymethyl, carboxyethyl, lower alkoxycarbonylethyl, lower alkoxycarbonylmethyl, etc.

Heterocycloalkane which $R^3$ and $R^1$ form with the N atom and the carbon atom is preferably pyrrolidine, piperidine, thiomorpholine, piperazine and morpholine. The substituent on the carbon atom in the said heterocycloalkane is the same or different, and 1 to 3 substituents, preferably lower alkyl group, such as methyl, ethyl, isopropyl, etc. The substituent on nitrogen atom in the said heterocycloalkane is preferably lower alkylcarbonyl group, alkoxycarbonyl group wherein each group may be substituted by aryl group such as phenyl, etc. or heteroaryl group such as pyridyl, etc., heteroarylcarbonyl group, arylcarbonyl group, or —$CONR^{11}R^{12}$ (wherein $R^{11}$ and $R^{12}$ are preferably hydrogen atom or lower alkyl, or $R^{11}$ and $R^{12}$ may form with the nitrogen atom a ring, such as morpholine, piperidine, pyrrolidine, N-lower alkylcarbonylpiperazine, N-loweralkylpiperazine, piperazine.), especially preferably, benzyloxycarbonyl group, methyl group, ethyl group, isopropyl group, benzyl group, morpholinocarbonyl group, 1-pyrrolidinylcarbonyl group, 1-piperidinylcarbonyl group, carbamoyl group, N,N-dimethylcarbamoyl group, 2-pyridylcarbonyl group, 3-pyridylcarbonyl group, 4-pyridylcarbonyl group, acetyl group, propionyl group, 2-furylcarbonyl group, 2-thienylcarbonyl group, methanesulfonyl group, isopropylsulfonyl group, benzoyl group, 2-methoxybenzoyl group, 3-methoxybenzoyl group, 4-methoxybenzoyl group, 2-methoxyethyl group, 2-ethoxyethyl group, etc.

Herein the configuration of carbon atom to which $R^1$ is bound is preferably D configuration.

$R^4$ is preferably C1~3 lower alkyl group, and more preferably methyl group.

$R^5$ is preferably hydrogen atom, C1~4 lower alkyl group, or C1~4 lower alkyl group substituted by lower alkoxy group or lower cycloalkyl group.

A hydroxamic acid derivative of the general formula (1), wherein $R^1$ and $R^2$ are each independently hydrogen atom, or C1~3 lower alkyl group, X is —$NR^3$ (wherein the said $R^3$ is C1~3 lower alkyl group which may be substituted by phenyl, pyridyl, C1~5 lower alkoxycarbonyl, carboxy or C1~5 lower alkoxy.), and $R^4$ is methyl group, is preferable.

A hydroxamic acid derivative of the general formula (1), wherein $R^1$ and $R^2$ are bound to form C3~4 straight alkylene, or a formula:

—$(CH_2)_2$—O—$(CH_2)_2$—, and X is —N—$R^3$ (wherein, the said $R^3$ is C1~4 lower alkyl group which may be substituted by C1~4 lower alkoxy group) is also preferable.

The processes for preparation of a compound of the present invention are shown as follows:

(Process 1: Process for Preparation of the Starting Material) 4-(4-Lower alkylsulfonylphenoxy)phenylsulfonyl chloride

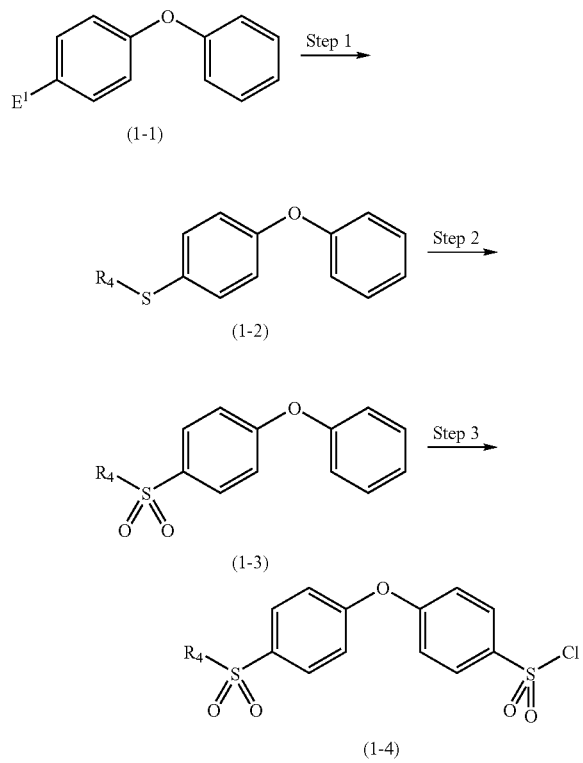

wherein $R^4$ is the same as defined above, and $E^1$ is iodine atom or bromine atom.

Step 1:

A compound (1-2) is prepared by reacting a compound (1-1) with an organic metal reagent, followed by reacting with a disulfide. The organic metal reagent includes, for example, an organic lithium reagent, such as n-butyl lithium, sec-butyl lithium, tert-butyl lithium, methyl lithium, phenyl lithium, etc., an organic magnesium reagent, such as isopropyl magnesium bromide, diisopropyl magnesium, etc. The disulfide includes methyl disulfide, ethyl disulfide, propyl disulfide, isopropyl disulfide, allyl disulfide, etc.

The solvent is not specifically limited as long as it does not inhibit the reaction and it can dissolve the starting material to some extent, and includes ethers, such as diethyl ether, diisopropyl ether, tetrahydrofuran, dioxane, etc., aromatic hydrocarbons such as benzene, toluene, xylene, etc., aliphatic hydrocarbons, such as pentane, hexane, heptane, etc., or a mixture thereof.

The reaction is carried out at −100° C. to room temperature, preferably −78° C. to 0° C. The reaction time is different in accordance with the reaction temperature, the starting material and the solvent used respectively, but is usually 30 minutes to 24 hours, preferably 1 to 24 hours.

Step 2:

A compound (1-3) is prepared by oxidizing a compound (1-2) with an oxidizing agent. The oxidizing agent includes OXONE (Registered T. M.), hydrogen peroxide, metachloroperbenzoic acid, peracetic acid, etc.

The solvent is not specifically limited as long as it is used for ordinal oxidation reaction, and includes, for example, halogenated hydrocarbons, such as dichloromethane, dichloroethane, etc., esters, such as methyl acetate, ethyl acetate, etc., aromatic hydrocarbons, such as benzene, toluene, xylene, etc., aliphatic hydrocarbons, such as pentane, hexane, heptane, etc., alcohols, such as methanol, ethanol, isopropanol, butanol, etc., water, or a mixture thereof. The reaction is carried out usually at −10° C. to 40° C., preferably for 30 minutes to 24 hours.

Step 3:

A compound (1-4) is prepared by being subjected to chlorosulfonylation of a compound (1-3). As a chlorosulfonylation agent, chlorosulfuric acid is used, if necessary in the presence of thionyl chloride. The chlorosulfonylation is carried out usually in the absence of a solvent, but is carried out in a solvent as long as it does not inhibit the reaction and can dissolve the starting material to some extent, such as a halogenated hydrocarbon, e.g., dichloromethane, dichloroethane, etc.

(Process 2)

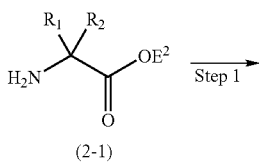

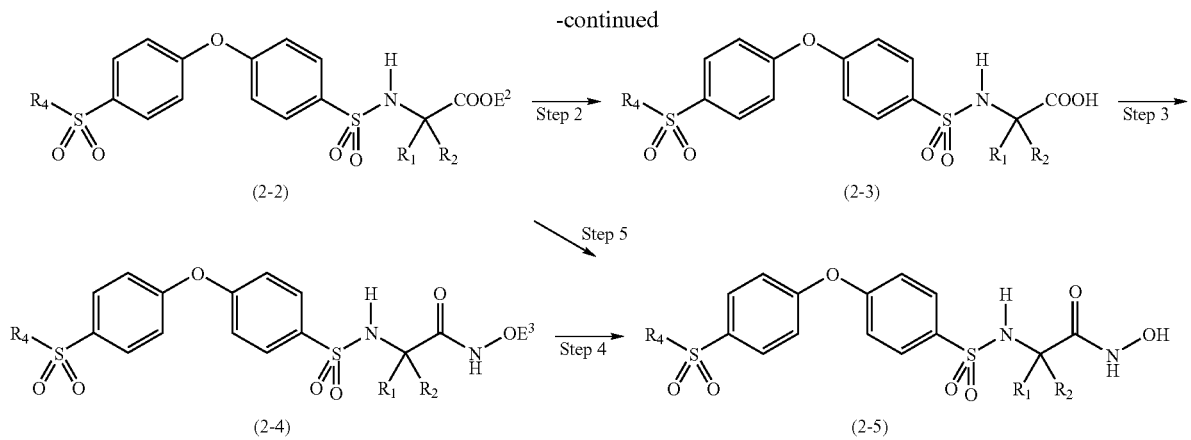

wherein, $R^1$, $R^2$ and $R^4$ are the same as defined above, $E^2$ is a protecting group of a carboxylic acid, such as methyl, ethyl, benzyl, tert-butyl, etc., and $E^3$ is hydrogen atom, or a protecting group of hydroxamic acid, such as, trimethylsilyl group, t-butyldimethylsilyl group, t-butyl group, allyl group, benzyl group, etc.

Step 1:

A compound (2-2) is prepared by reacting a compound (2-1) having a protected carboxyl group and arylsulfonyl chloride (1-4) in the presence or absence of a base.

The solvent is not specifically limited as long as it does not inhibit the reaction and it can dissolve the starting material to some extent, and includes preferably halogenated hydrocarbons, such as dichloromethane, chloroform, carbon tetrachloride, dichloroethane, etc., ethers, such as diethyl ether, diisopropyl ether, tetrahydrofuran, dioxane, etc., aprotic polar solvents, such as N,N-dimethylformamide, N,N-dimethylacetamide, N-methyl-2-pyrrolidinone, 1,3-dimethyl-2-imidazolidinone, dimethyl sulfoxide, etc., nitrites, such as acetonitrile, etc., esters, such as methyl acetate, ethyl acetate, etc., aromatic hydrocarbons, such as benzene, toluene, xylene, etc., aliphatic hydrocarbons, such as pentane, hexane, heptane, etc., or a mixture thereof.

The base is not specifically limited as long as it is used for usual amidation reaction, and includes preferably an organic base containing a nitrogen atom, such as triethylamine, diisopropylethylamine, tributylamine, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU), pyridine, dimethylaminopyridine, picoline, N-methylmorpholine (NMM), etc., an inorganic base, such as sodium hydrogencarbonate, potassium hydrogencarbonate, sodium carbonate, potassium carbonate, etc.

The reaction is carried out at $-20°$ C. to $150°$ C., preferably $0°$ C. to $60°$ C. The reaction time is different in accordance with the reaction temperature, the starting material and the solvent used respectively, but is usually 30 minutes to 48 hours, preferably 30 minutes to 24 hours.

Step 2:

This step is a process for preparation of a compound (2-3) by subjecting to deprotection reaction of the ester group of a compound (2-2). The step is carried out in accordance with the method described in Green, Protective Groups in Organic Synthesis (John Wiley & Sons Inc. (1981)).

The step is illustratively carried out as follows:

(1) When $E^2$ is lower alkyl group, such as methyl group, ethyl group, etc., a carboxylic acid is prepared by alkali hydrolysis or acid hydrolysis. Namely, a compound (2-3) is prepared by reacting a compound (2-2) with water in the presence of an alkali metal hydroxide or an alkaline earth metal hydroxide, such as sodium hydroxide, potassium hydroxide, lithium hydroxide, magnesium hydroxide, etc., in the presence or absence of an inert solvent, such as alcohols, e.g., methanol, ethanol, isopropanol, butanol, etc., ethers, e.g., diethyl ether, diisopropyl ether, tetrahydrofuran, dioxane, etc., aromatic hydrocarbons, e.g., benzene, toluene, xylene, etc., usually at room temperature to refluxing temperature for 30 minutes to 2 days.

In case of acid hydrolysis, the reaction is carried out in water in the presence of a mineral acid, such as sulfuric acid, hydrochloric acid, etc., or an organic acid, such as trifluoroacetic acid, trifluoromethanesulfonic acid, etc., usually at room temperature to refluxing temperature for 30 minutes to 2 days, to give a compound (2-3).

(2) When $E^2$ is benzyl group, the reaction is carried out under stirring in hydrogen atmosphere in the presence of a transition metal catalyst, such as palladium/carbon, palladium hydroxide, nickel, etc., and if necessary by adding ammonium formate, etc., to give a compound (2-3). The solvent includes alcohols, such as methanol, ethanol, isopropanol, butanol, etc., ethers, such as diethyl ether, diisopropyl ether, tetrahydrofuran, dioxane, etc., aromatic hydrocarbons, such as benzene, toluene, xylene, etc., esters, such as ethyl acetate, methyl acetate, or a mixture thereof.

(3) When $E^2$ is tert-butyl group, the reaction is carried out in the presence of an acid, such as hydrochloric acid, formic acid, paratoluenesulfonic acid, acetic acid-hydrobromic acid, trifluoroacetic acid, etc., or a Lewis acid such as boron trifluoride, etc., to give a compound (2-3). In this reaction acetonitrile or dioxane can be used as a solvent.

Step 3:

This step is carried out by activating carboxy group of a compound (2-3) followed by reacting with hydroxylamine or a protected hydroxylamine. The protected hydroxylamine includes preferably, N,O-bis(trimethylsilyl)hydroxylamine, O-(trimethylsilyl)hydroxylamine, etc.

The activating method of the carboxy group include acid anhydride-method, mixed acid anhydride-method, acid halide-method, active esterification-method, and acid azide-method, preferably acid halide-method, and mixed acid anhydride-method.

When the acid halide-method is adopted, the reaction is carried out by reacting a compound (2-3) with a halogenating agent, such as oxaryl chloride or thionyl chloride to prepare a halide, and then by reacting it with hydroxylamine or protected hydroxylamine in the presence of a base to give a compound (2-4).

The base is not specifically limited as long as it is used for usual amidation reaction, and includes preferably an organic base containing a nitrogen atom, such as triethylamine, diisopropylethylamine, tributylamine, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU), pyridine, dimethylaminopyridine, picoline, N-methylmorpholine (NMM), etc., an inorganic base, such as sodium hydrogencarbonate, potassium hydrogencarbonate, sodium carbonate, potassium carbonate, etc.

The solvent includes halogenated hydrocarbons, such as dichloromethane, chloroform, carbon tetrachloride, dichloroethane, etc., ethers, such as diethyl ether, diisopropyl ether, tetrahydrofuran, dioxane, etc., aromatic hydrocarbons, such as benzene, toluene, xylene, etc., esters, such as methyl acetate, ethyl acetate, etc., water, or a mixture thereof. The reaction is carried out at −80° C. to 150° C., preferably usually at −20° C. to 80° C.

The reaction time is different in accordance with the reaction temperature, the starting material and the solvent used respectively, but is usually 10 minutes to 48 hours, preferably 30 minutes to 24 hours.

When the mixed acid anhydride-method is adopted, the reaction is carried out by reacting a compound (2-3) with an acid halide to prepare a mixed acid anhydride and then by reacting it with hydroxylamine or protected hydroxylamine in the presence of a base to give a compound (2-4). The acid halide includes methoxycarbonyl chloride, ethoxycarbonyl chloride, isopropyloxycarbonyl chloride, isobutyloxycarbonyl chloride, paranitrophenoxycarbonyl chloride, t-butylcarbonyl chloride, etc. The base is not specifically limited, and includes preferably an organic base containing a nitrogen atom, such as triethylamine, diisopropylethylamine, tributylamine, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU), pyridine, dimethylaminopyridine, picoline, N-methylmorpholine (NMM), etc., an inorganic base, such as sodium hydrogencarbonate, potassium hydrogencarbonate, sodium carbonate, potassium carbonate, etc.

The solvent includes halogenated hydrocarbons, such as dichloromethane, chloroform, carbon tetrachloride, dichloroethane, etc., ethers, such as diethyl ether, diisopropyl ether, tetrahydrofuran, dioxane, etc., aromatichydrocarbons, such as benzene, toluene, xylene, etc., esters, such as methyl acetate, ethyl acetate, etc., or a mixture thereof.

The reaction is carried out at −40° C. to 80° C., preferably usually at −20° C. to 30° C. The reaction time is different in accordance with the reaction temperature, the starting material and the solvent used respectively, but is usually 10 minutes to 48 hours, preferably 30 minutes to 24 hours.

The compound (2-4) is also prepared by reacting a compound (2-3) with protected hydroxylamine in the presence or absence of a dehydrating-condensing agent and a base.

The condensing agent includes diphenylphosphorylazide (DPPA), diethylphosphorylcyanide (DEPC), dicyclohexylcarbodiimide (DCC), carbonyldiimidazole (CDI), 1-ethyl-3-(3-dimethylaminopropyl)carbodiimide.hydrochloride (EDC.HCl), O-(1H-benzotriazol-1-yl)-1,1,3,3-tetramethyluronium tetrahydoroborate (TBTU), O-(1H-benzotriazol-1-yl)-N,N,N',N'-tetramethyluronium hexafluorophosphate (HBTU), (benzotriazol-1-yloxy)tris(dimethylamino)phosphonium hexafluorophosphate, etc.

The solvent is not specifically limited as long as it does not react in this reaction, such as halogenated hydrocarbons, e.g., dichloromethane, chloroform, carbon tetrachloride, dichloroethane, etc., ethers, e.g., diethyl ether, diisopropyl ether, tetrahydrofuran, dioxane, etc., aromatic hydrocarbons, e.g., benzene, toluene, xylene, etc., esters, e.g., ethyl acetate methyl acetate, etc., aprotic polar solvents, e.g., N,N-dimethylformamide, N,N-dimethylacetamide, N-methyl-2-pyrrolidinone, 1,3-dimethyl-2-imidazolidinone, dimethyl sulfoxide, etc., water, or a mixture thereof.

The base is not specifically limited, but includes preferably an organic base containing a nitrogen atom, such as triethylamine, diisopropylethylamine, tributylamine, 1,5-diazabicyclo[4.3.0]nona-5-ene (DBN), 1,4-diazabicyclo[2.2.2]octane (DABCO), 1,8-diazabicyclo[5.4.0]undeca-7-ene (DBU), pyridine, dimethylaminopyridine, picoline, N-methylmorpholine (NMM), etc.

The reaction is carried out usually at −10° C. to refluxing temperature, preferably at −20° C. to 80° C. The reaction time is different in accordance with the reaction temperature, the starting material and the solvent used respectively, but is usually 30 minutes to 48 hours, preferably 30 minutes to 24 hours.

The activation method of a carboxylic acid is carried out in accordance with the methods described in WO 00/63197 and Comprehensive Organic Transformation (Larock, R. C., VCH Publishers, Inc. (1989)), etc.

Step 4:

A compound (2-4), wherein $E^3$ is a protecting group of hydroxamic acid, is subjected to deprotecting reaction in this step to give a compound (2-5). The deprotecting reaction is carried out depending on the property of the protecting group, in accordance with Green, Protective Groups in Organic Synthesis (John Wiley & Sons Inc. (1981)). Examples thereof are as follows:

When $E^3$ is t-butyl, the treatment by a strong acid, such as trifluoroacetic acid, hydrochloric acid, etc., is carried out, and when $E^3$ is benzyl, hydrogenolysis with palladium/carbon is carried out. When $E^3$ is allyl, the treatment by tributyltin hydride and acetic acid in the presence of bis(triphenylphosphine)palladium(II) chloride as catalyst is carried out, and when $E^3$ is trimethylsilyl group or t-butyldimethylsilyl group, the treatment by an acidic solution such as diluted hydrochloric acid is carried out.

Step 5:

A compound (2-2) is subjected to reaction with hydroxylamine to produce a compound (2-5).

For example, hydroxylamine hydrochloride is treated in an alcoholic solvent, such as ethanol, propanol, or methanol, with a base such as sodium hydroxide, potassium hydroxide, sodium methoxide, sodium ethoxide, or potassium t-butoxide, to prepare free hydroxylamine solution, and then it was treated with a compound of (2-2) to produce a compound (2-5).

The reaction is carried out usually at room temperature to 150° C. The reaction time is different in accordance with the reaction temperature, the starting material and the solvent used respectively, but is usually 10 minutes to 48 hours, preferably 30 minutes to 24 hours. This method is described in WO 00/63197.

(Process 3: Process for preparation of starting material)

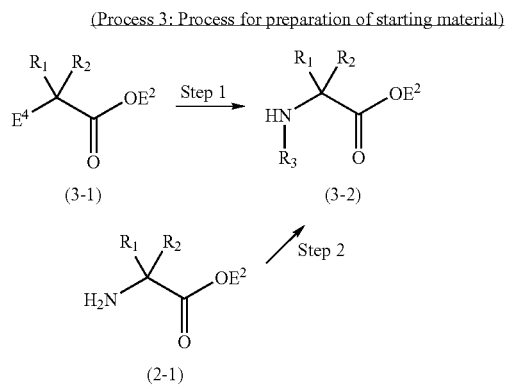

wherein $R^1$, $R^2$, $R^3$ and $E^2$ are the same as define above, and $E^4$ is chlorine atom, bromine atom or iodine atom.

Step 1:

A compound (3-1) can be subjected to reaction with $R^3$—$NH_2$ or a salt thereof in the presence or absence of a base to produce a compound (3-2).

The base is not specifically limited, and includes preferably an organic base containing a nitrogen atom, such as triethylamine, diisopropylethylamine, tributylamine, N-methylmorpholine (NMM), etc.

The solvent includes alcohols, such as methanol, ethanol, isopropanol, butanol, etc., ethers, such as diethyl ether, diisopropyl ether, tetrahydrofuran, dioxane, etc., or aprotic polar solvents, such as N,N-dimethylformamide, N,N-dimethylacetamide, N-methyl-2-pyrrolidinone, 1,3-dimethyl-2-imidazolidinone, dimethyl sulfoxide, etc.

The reaction is carried out usually at −10° C. to refluxing temperature, but preferably at 0° C. to 80° C. The reaction time is different in accordance with the reaction temperature, the starting material and the solvent used respectively, but is usually 1 hour to 48 hours, preferably 1 hour to 24 hours.

Step 2:

A compound (3-2) is prepared by reacting a compound (2-1) and $R^3$—Cl, $R^3$—Br, $R^3$—I, etc., in the same manner as the method of Step 1.

A compound (3-2) is also prepared by reacting an imine compound which is prepared by reacting a compound (2-1) and an aldehyde or a ketone, with a hydride reducing agent, such as sodium cyanoboron hydride, or sodium triacetoxy boron hydride.

The solvent includes organic acids, such as acetic acid, propanoic acid, alcohols, such as ethanol, methanol, halogenated hydrocarbons, such as dichloromethane, dichloroethane, etc., acetonitrile, etc.

The reaction is carried out usually at −10° C. to refluxing temperature, but preferably at 0° C. to 50° C. The reaction time is different in accordance with the reaction temperature, the starting material and the solvent used respectively, but is usually 1 hour to 48 hours, preferably 1 hour to 24 hours.

A compound (3-2) is treated in the same manner as the process 2 to produce a compound of the present invention.

(Process 4)

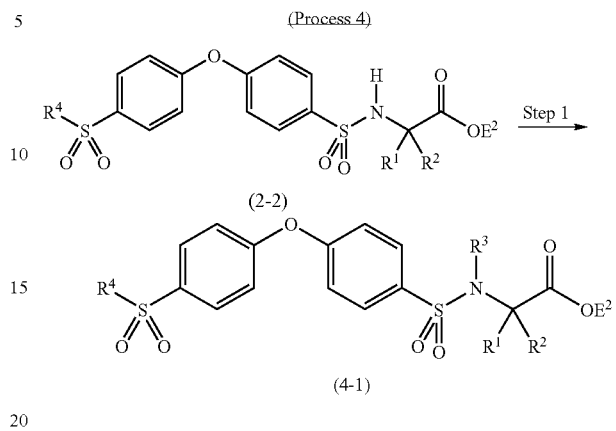

wherein $R^1$, $R^2$, $R^3$, $R^4$ and $E^2$ are the same as defined above.

Step 1:

A compound (2-2) is treated with a base, and then reacting with a halogenated compound, such as $R^3$—Cl, $R^3$—Br, $R^3$—I, etc., to produce a compound (4-1).

The base includes inorganic bases, such as potassium carbonate, sodium carbonate, etc., metal halides, such as sodium hydride, lithium hydride, etc., potassium hexamethyldisilazide, sodium hexamethyldisilazide, diisopropylamide, etc.

The solvent includes preferably ethers, such as diethyl ether, disopropyl ether, tetrahydrofuran, dioxane, etc., polar solvents, such as N,N-dimethylformamide, N,N-dimethylacetamide, N-methyl-2-pyrrolidinone, 1,3-dimethyl-2-imidazolidinone, dimethyl sulfoxide, etc.

The reaction time is different in accordance with the reaction temperature, the starting material and the solvent used respectively, but is preferably 30 minutes to 72 hours at room temperature to refluxing temperature.

A compound (4-1) is treated in the same manner as the process 2 to produce a compound of the present invention.

(Process 5)

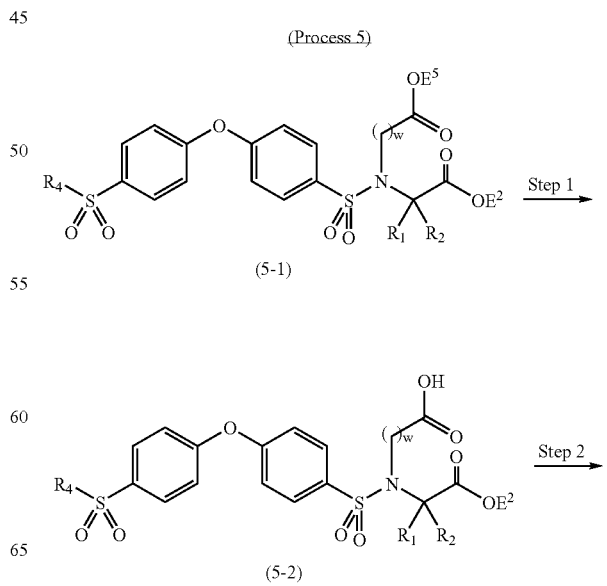

-continued

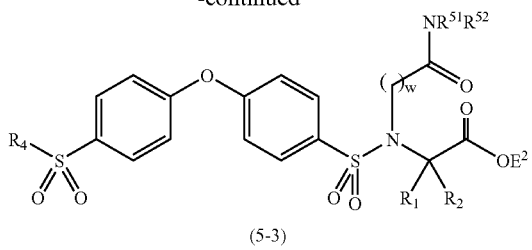

(5-3)

wherein $R^1$, $R^2$ and $E^2$ is the same as defined above, $E^5$ is a protecting group of the ester which can be deprotected by the method different from the deprotecting method in $E^2$, and $R^{51}$ and $R^{52}$ are the same as defined as the above $R^{11}$ and $R^{12}$, respectively, or a group convertible to $R^{11}$ and $R^{12}$, and w is an integer of 1~5.

Step 1:

A compound (5-1) is prepared by the process 3. A compound (5-1) is treated in accordance with the method of the process 2 to produce a compound (5-2), provided that the deprotection of the protecting group is selected from the condition that ester $E^2$ is not deprotected. For example, when $E^2$ is ethyl group and $E^5$ is benzyl group, only $E^5$ can be selectively deprotected by catalytic dehydrogenation. The said method is described in Green, Protective Groups in Organic Synthesis (John Wiley & Sons Inc. (1981)).

Step 2:

A compound (5-2) is treated with a mixed acid anhydride in the presence of a base to prepare a mixed anhydride and then, the product is reacted with an amine: $R^{51}R^{52}NH$ to produce a compound (5-3). The dehydrating-condensing with the mixed anhydride is carried out in accordance with the method of the process 2.

A compound (5-2) is reacted with an amine: $R^{51}R^{52}NH$ in the presence of an appropriate condensing agent and a base usually at 0° C. to room temperature for 1 hour to 48 hours to give a compound (5-3), too.

The examples of the condensing agent are described in Jikken Kagaku Kouza (edited by Nippon Kagaku Kai, Maruzen), Vol. 22, such as diethyl cyanophosphate, phosphate of diphenylphospholylazide, etc., carbodiimides such as 1-ethyl-3-(3-dimethylaminopropyl)carbodiimide.hydrochloride, dicyclohexylcarbodiimide, etc., a combination of disulfide such as 2,2'-dipyridyldisulfide, etc., and a phosphine such as triphenylphospine, phsphohalide such as N,N'-bis(2-oxo-3-oxazolizinyl)phosphinic chloride, etc., a combination of a azodicarboxylic acid diester such as azodicarboxylic acid diethyl ester, etc., and a phosphine such as triphenyl phosphine, 2-halo-1-lower alkylpyridinium halides, such as 2-chloro-1-methylpyridinium iodide, etc., 1,1'-carbonyldiimidazole, etc.

The inactive solvent includes organic solvents, such as ethers, such as tetrahydrofuran, diethyl ether, dioxane, 1,2-dimethoxyethane, etc., hydrocarbons, such as hexane, heptane, toluene, benzene, xylene, etc., halogenated hydrocarbons such as dichloromethane, chloroform, 1,2-dichloroethane, ketones such as acetone, polar organic solvents, such as acetonitrile, N,N-dimethylformamide, N-methyl-2-pyrrolidinone, 1,3-dimethyl-2-imidazolizinone, dimethyl sulfoxide, hexamethylenephosphoamide, or a mixture thereof.

The base is not limited as long as it is used as a base in the usual reaction, and includes an organic base containing a nitrogen atom, such as N-methylmorpholine, triethylamine, diisopropylethylamine, tributylamine, DBU, DBN, DABCO, pyridine, dimethylaminopyridine, pycoline, etc., an inorganic base, such as sodium hydrogencarbonate, potassium hydrogencarbonate, sodium carbonate, potassium carbonate, etc.

A compound (5-3) is treated in accordance with the process 2 to produce a compound (1) of the present invention.

(Process 6)

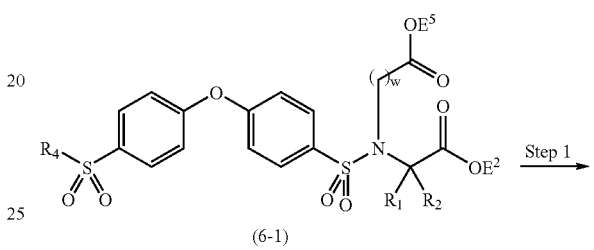

(6-1)

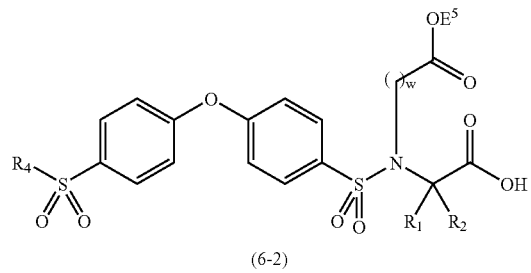

(6-2)

wherein $R^1$, $R^2$, $R^4$, w, $E^2$ and $E^5$ are the same as defined above.

Step 1:

A compound (6-1) can be prepared by the process 3. A compound (6-1) is treated in accordance with the method of the process 2 to produce a compound (6-2) provided that the deprotection of the protecting group is selected from the condition that ester $E^5$ is not deprotected. For example, when $E^5$ is ethyl group and $E^2$ is benzyl group, only $E^2$ can be selectively deprotected by catalytic dehydration. The said method is described in Protective Groups in Organic Synthesis (John Wiley & Sons Inc. (1981)). A compound (6-2) is treated by the process 2 to produce a compound (1) of the present invention. Namely —$COOE^2$ group can be converted to hydroxamic acid. Further, $E^5$ can be deprotected to give carboxy group.

(Process 7)

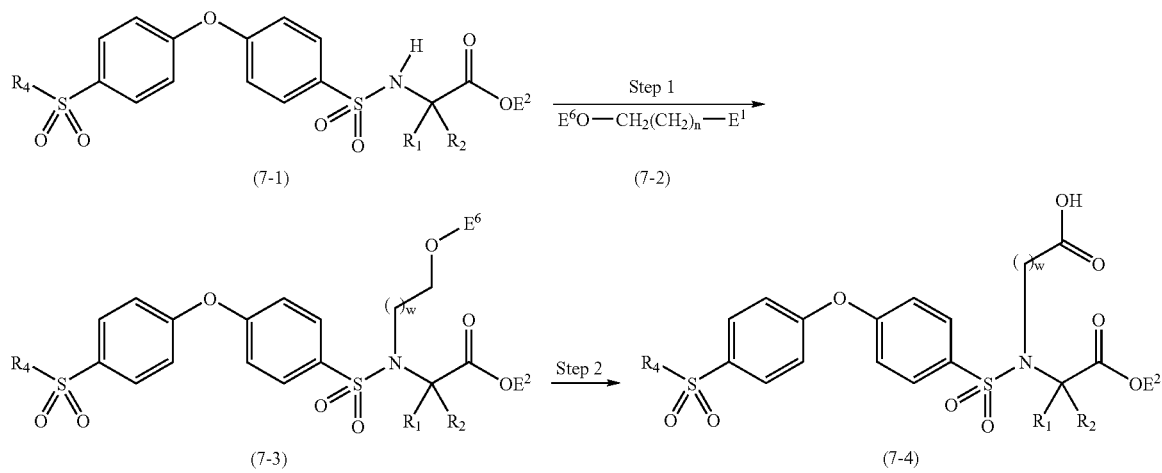

wherein $R^1$, $R^2$, $R^4$, w, $E^1$ and $E^2$ are the same as defined above, and $E^6$ is a protecting group of hydroxy group, such as t-butyl dimethylsilyl group, etc., or lower alkyl group which is optionally substituted or lower haloalkyl group which is optionally substituted.

Step 1:

A compound (7-1) is prepared by the process 2. A compound (7-1) and a compound (7-2) are reacted in accordance with the method of the process 3 to produce a compound (7-3).

Step 2:

When $E^6$ is a protecting group of hydroxy group, the said group of a compound (7-3) is deprotected to prepare an alcohol and then, hydroxy group is oxidized to produce a compound (7-4).

For example, when $E^6$ is t-butyldimethylsilyl group, the compound is reacted with boron trifluoride-ether complex in a halogenated hydrocarbon such as dichloromethane or chloroform at 0° C. to room temperature for 15 minutes to 6 hours to deprotecte $E^6$, and to produce an intermediate, alcohol. Then, the product is reacted with John's reagent in acetone at 0° C. to room temperature for 15 minutes to 30 minutes and there is obtained a compound (7-4).

After protecting carboxyl group of a compound (7-4) with an appropriate protecting group, a compound (1) is prepared by the method of the process 5 or 6. In the same manner as the process 2, by using a compound (7-3) the ester portion is converted into hydroxamic acid to give a compound (1) of the present invention.

(Process 8)

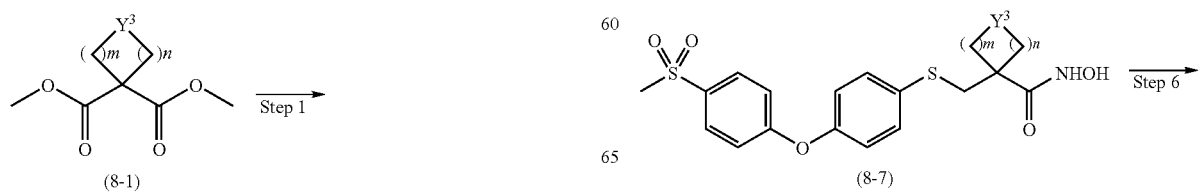

-continued

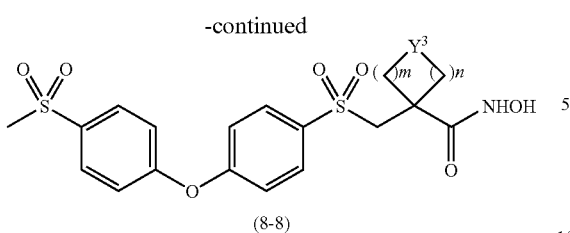

(8-8)

wherein m and n are the same as defined above, and $Y^3$ is —$CH_2$—O—, —$NR^5$— or —$SO_2$—.

Step 1:

This step is a step to prepare a compound (8-2) from a compound (8-1) with a reducing agent. It is an effective method that only one of esters is reduced to aldehyde which is further reduced to alcohol. A compound (8-1) is kept at −20° C. or less than −20° C. (preferably from−40° C. to −20° C.) in an inert organic solvent (preferably toluene) and is reacted with an appropriate week reducing agent, such as diisopropylalminium hydride and thereto is added methanol or ethanol. Furthermore, thereto sodium boron hydride is added and the temperature is elevated to room temperature to give a compound (8-2).

Step 2:

This step is a hydrolysis step of ester. A compound (8-2) is dissolved in a co-solvent of an alcohol such as methanol, etc., and water and, if necessary an ether such as tetrahydrofuran is added thereto. To this solution is added a base, such as lithium hydroxide or sodium hydroxide and the mixture is reacted at 50° C. to refluxing temperature and then treated under acidic condition to give a compound (8-3).

Step 3:

This step is a step to prepare a lactone compound (8-4) by reacting a compound (8-3) and an appropriate dehydrating agent.

The step is carried out by reacting a compound (8-3) in an inert solvent such as diethyl ether, etc., in the presence of a base such as the tertiary amine like ethylamine, with a dehydrating agent such as trifluoromethanesulfonic acid anhydride or methane sulfonic anhydride. The reaction is carried out preferably in a range of ice cooling to at room temperature, usually for 30 minutes to 1 day.

Step 4:

This step is a process for preparing a compound (8-6) by reacting a lactone: (8-4) with an anion of a thiol (8-5).

A compound (8-5) is reacted in an aprotic polar solvent such as dimethylformamide, etc., or an ether such as tetrahydrofuran, etc., from under ice cooling to room temperature with a base such as sodium hydride or potassium hydride. Thereto is added a compound (8-4) to produce a compound (8-6).

The reaction is carried out preferably at 0° C. from to 60° C., usually for 30 minutes to 12 hours.

Step 5:

This step is a step for preparing hydroxamic acid: (8-7) starting from a carboxylic acid: (8-6). The step is carried out in the same manner as step 3 of the process 2, preferably by using the acid halogenation method.

Step 6:

This step is an oxidation step from a sulfide: (8-7) to a sulfone: (8-8). The step is carried out in the same manner as step 2 of the process 1.

(Process 9)

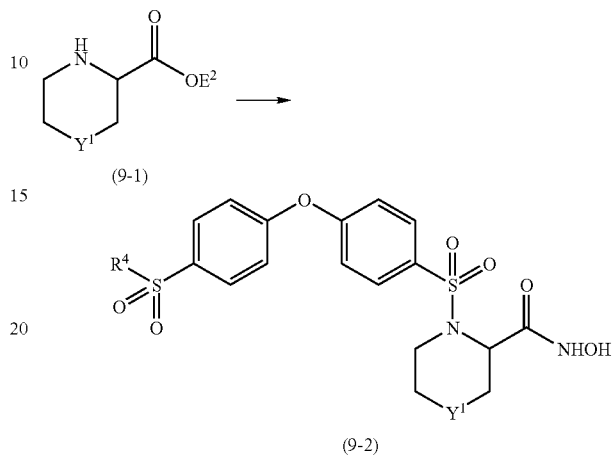

wherein $Y^1$ is a single bond, methylene, oxygen atom or sulfur atom, and $R^4$ and $E^2$ are the same as defined above.

A compound (9-2) can be prepared starting from a compound (9-1) in the same manner as the process 2. The compound (9-1) can be prepared by the known method.

(Process 10)

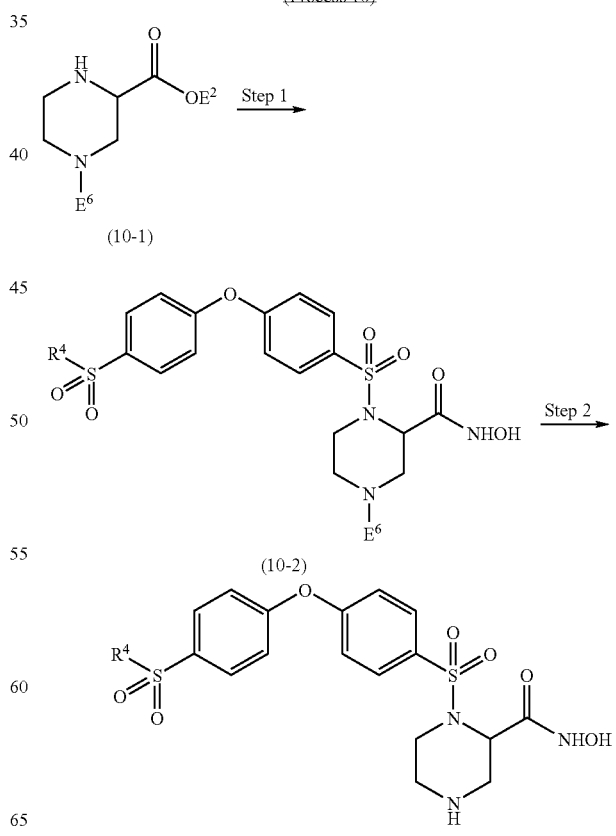

wherein $R^4$ and $E^2$ are the same as defined above, and $E^6$ is a protecting group of the amino group which can be deprotected by the method different from the deprotecting method in $E^2$ Step 1:

A compound (10-5) can be prepared staring from a compound (10-1) in the same manner as the process 2. When $E^6$ is a protecting group of the amino group, a combination of $E^6$ and $E^2$ includes, for example, benzyl group and lower alkyl group such as methyl group, or t-butoxycarbonyl group and lower alkyl group such as methyl group, etc. A compound (10-1) is commercially available or can be prepared by the known method.

Step 2:

The protective group of the compound (10-2) is deprotected by the method described in the above mentioned Protective Groups in Organic Synthesis (John Wiley & Sons Inc. 1981).

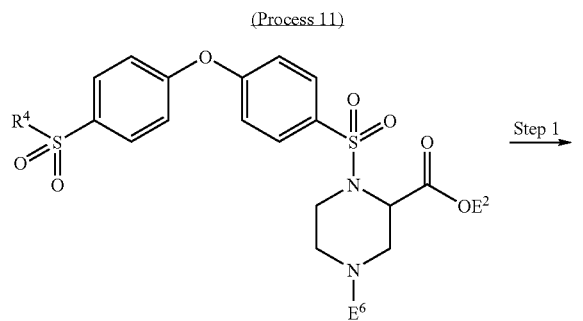

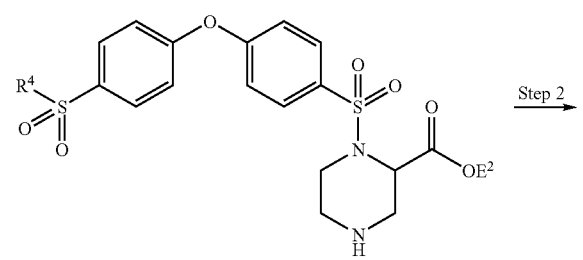

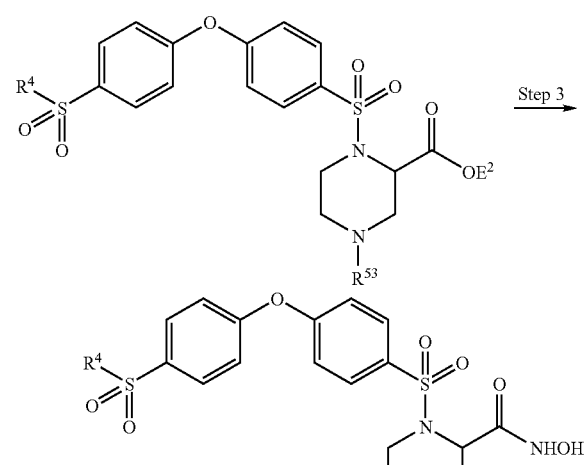

wherein $R^4$, $E^2$ and $E^6$ are the same as defined above, and $R^{53}$ is a substituent on heterocycloalkane which is formed by $R^3$ and $R^1$ in formula (1) combined together.

Step 1:

The protecting group of a compound (11-1) which is prepared in the same manner as the process 10 is deprotected to give a compound (11-2). The condition for deprotection is not limited as long as the protecting group $E^2$ of the ester does not react. For example, when $E^2$ is lower alkyl, such as methyl group, ethyl group, etc., and $E^6$ is benzyl group, the method described in step 2(2) of the process 2 can be used. When $E^6$ is t-butyl, the method described in step 2(3) of the process 2 can be used.

Step 2:

(When $R^{53}$ is lower alkyl carbonyl group, lower arylcarbonyl group, lower alkoxycarbonyl group, lower alkylsulfonyl group, lower allylsulfonyl group, etc.)

A compound (11-2) is reacted with an acyl halide such as an acyl chloride in an inert solvent in the presence of a base, such as a tertial amine such as triethylamine, and a base containing a nitrogen atom such as pyridine, or a base such as potassium carbonate, etc. The inert solvent includes preferably halogenated hydrocarbons such as dichloromethane, etc., ethers such as tetrahydrofuran, etc. The reaction is carried out at 0° C. to refluxing temperature, preferably at 0° C. to room temperature. Further, when a carboxylic acid is used, the product can be prepared in the same manner as step 2 of the process 5. (When $R^{53}$ is lower Alkyl, carbamoyl group, etc.)

The compound is prepared by reacting a compound (11-2) with isocyanate and, if necessary in the presence of a tertiary amine such as triethylamine, etc., a base containing a nitrogen atom such as pyridine, etc. After reacting a compound (11-2) with 4-nitrophenyl chloroformate or phosgene in an inert solvent in the presence of a tertiary amine, and then by reacting it with a primary amine or a secondary amine. The inert solvent includes halogenated hydrocarbon such as dichloromethane, etc., ethers such as tetrahydrofuran, etc., aromatic hydrocarbon such as toluene, etc. The reaction is carried out at 0° C. to refluxing temperature, preferably at room temperature to refluxing temperature.

(When $R^{53}$ is optionally substituted lower alkyl group, etc.)

The compound can be prepared in the same manner as the process 3.

Step 3:

The compound is prepared in the same manner as the process 2.

In the processes explained above, when any functional group other than a reaction site is changed under the condition mentioned above, or it is not suitable to carry out the method explained above, the reactive groups other than the reaction site are protected to prepare the object compound. The protecting groups which are usually used are ones described in Protective Groups in Organic Synthesis (John Wiley & Sons Inc. 1981), etc. For example, a protecting group of the amine includes ethoxycarbonyl, t-butoxycarbonyl, acetyl, benzyl etc., and a protecting group of hydroxy group includes tri lower alkylsilyl, acetyl, benzyl, etc.

The introduction or elimination of the protecting group is conducted accordance with the conventional method used in the field of organic synthesis (for example, see the above Protective Groups in Organic Synthesis), or the similar method therewith.

In addition, an intermediate or a final product in the above method can be converted to another compound of the present invention by suitably changing the functional group of the said compound. The conversion of the functional group is carried out by the conventional method (for example, see R. C. Larock, Comprehensive Organic Transformations (1989), etc.).

An intermediate or an object product in each the above method is subjected to purification methods such as neutrization, filtration, extraction, washing, drying, concentration, recrystalization, many kinds of chromatographies, etc. It is possible to serve the intermediate to next reaction with out purification.

In addition, an optical isomer is separated by a known method such as using an optically active column, fractional crystallization, etc., in a suitable course of the above methods. As a starting material, an optical active form of a compound (10-1) can be also used.

When the compounds (1) of the present invention have optical isomers, stereoisomers, tautomers and/or geometrical isomers, the compound (1) of the present invention includes all possible isomers and a mixture thereof as well as those isomers.

When there are optical isomers more than two based on asymmetric carbon atoms in the compound (1) of the present invention, the said optical isomers and a mixture thereof are also included within the scope of the present invention.

The compound (1) of the present invention also includes a pharmaceutically acceptable salt. When the compound (1) of the present invention has an acidic group such as carboxy group, the base which is used for preparation of its basic salt is a compound forming a nontoxic basic salt with these compounds. These nontoxic basic salts include cathion, for example an alkali metal salt (e.g., potassium salt and sodium salt) and an alkaline earth metal salt (e.g., calcium salt and magnesium salt), ammonium or aqueous amine additional salt, such as N-methylglucamine (meglumine), a pharmaceutically acceptable organic amine lower alkanolammonium salt or other basic salts, and does not limited to these salt, and includes a pharmaceutically acceptable solvate thereof such as water.

When the compound (1) of the present invention has a basic group such as pyridyl, etc., the acid used for preparation of its acid additional salt is an acid to form a nontoxic acid additional salt, namely a salt containing a pharmacologically acceptable anion, such as hydrochloride, hydrobromide, hydroiodide, nitrate, sulfate, hydrogensulfate, phosphate, acid phosphate, acetate, lactate, citrate, acidic citrate, tartarate, hydrogen tartarate, succinate, maleate, fumarate, gluconate, succharate, benzoate, methanesulfonate, ethanesulfonate, benzenesulfonate, p-toluenesulfonate, pamoate (1,1'-methylene-bis-(2-hydroxy-3-naphthoate)), etc.

When a salt of the compound (1) is desired, in case that the compound is obtained in a salt, the salt is purified itself, in case of a free base, it is dissolved or suspended in an appropriate solvent, and thereto is added an acid or base and the salt is prepared by the conventional method.

The compound (1) of the present invention or a pharmacologically acceptable salt thereof may present in a solvate with water or a solvent, and these addionals are included in the present invention.

The present invention includes also a prodrug of compound (1) of the present invention. A compound having free amino group, amide group, hydroxy group or carboxyl group can be converted to a prodrug. As a prodrug, a peptide containing an amino acid residue or a peptide wherein plural (e.g., 2 to 4) amino residues is covalently bound to free amino group, amide group, hydroxy group or carboxyl group via peptide bond.

The amino acid residue includes the same or different and desired amino acid residue, for example 20 naturally occurring amino acids, 4-hydroxyproline, hydroxylysine, demosine, isodemosine, 3-methylhistidine, norvaline, β-alanine, γ-aminolactic acid, citrulline, homocysteine, homoserine, ornithine, methioninesulfone, etc.

Further, the prodrug includes a carbonate, a carbamate, an amide and a lower alkyl ester which covalently binds to oxygen atom and/or to a nitrogen atom of hydroxamic acid group, too.

When the compound (1) of the present invention has carboxyl group, prodrugs described in Chemistry and Industry, 1980, 435; Advanced Drug Discovery Reviews, 3, 39 (1989) are illustrated. For example, there are illustrated esters which is easily hydrolysable in a living body such as a lower alkyl ester, e.g., ethyl ester, etc., lower alkoxycarbonyloxyalkyl ester, e.g., as ethoxycarbonyloxymethyl group, etc., lower cycloalkoxycarbonyloxyalkyl ester, e.g., cyclohexyloxycarbonyloxy(1-methyl)methyl group, etc., acyloxymethyl ester, glucorate, lactate, morpholinoethyl ester, etc.

The prodrug of the compound (1) of the present invention having hydroxy group is for instance, an ester such as acetate, etc.

The compound (1) of the present invention, its pharmaceutically acceptable salt or its prodrug is administered orally or perenterally (e.g., intravenously, subcutaneously, intravenous drip, intramuscularly, intranasaly, in ophthalmic solutions, in suppository, intradermally (ointment, cream, lotion, etc.)). The preparation for oral application includes for example, tablets, capsules, pills, granules, powders, solutions, syrups, suspensions. The preparation for perenteral administration includes an aqueous solution or oily solution for injection, ointments, creams, lotions, aerosols, suppositories, patches, etc.

These preparations are prepared in accordance with the conventional methods and can contain excipients, bindings, stabilizer, lubricants, disintegrants, etc., which are conventionally used. An acceptable buffer, solvilizing agent, isotonizing agent, etc., may be added to the preparation for injection. If necessary a sweetening agent or a flavor can also be used.

The sweetening agent or flavor includes ones conventionally used, for example a sweetening agent, a sour, a flavor, etc.

The excipients includes, for example sugars, such as lactose, sucrose, glucose, mannitol, sorbitol; starches such as corn starch, potato starch, α-starch, dextrin, carboxymethyl starch, etc.; cellulose derivatives, such as crystalline cellulose, lower substituted hydroxypropylcellulose, hydroxypropylmethyl cellulose, carboxymethyl cellulose, calcium carboxymethyl cellulose, innerbriged sodium carboxymethyl cellulose, etc.; gum arabic; dexran; an organic excipient such as pullulan, etc.; and an inorganic excipient, such as a silicate derivative such as light silicic acid anhydride, synthesized aluminum silicate, metasilicic acid aluminum magnesium, etc.; a phosphate such as calcium phosphate; a carbonate such as calcium carbonate, etc.; a sulfate such as calcium sulfate, etc.

The lubricant includes, for example metal salt of stearic acid such as stearic acid, calcium stearate, magnesium stearate, etc., talc; colloidal silica; wax such as bee gum, whale wax; boric acid: adipic acid; a sulfate such as sodium sulfate; glycol; fumaric acid; sodium benzoate; DL-leucine; sodium fatty acid salt; a laurylate such as sodium laurylate, magnesium laurylate; silicic acids such as silicic acid anhydride, silicic acid hydrate, etc.; and the above mentioned starches.

The binding agent includes, for example polyvinylpyrrolidone, macrogole, the same compound as the above excipient.

The disintegrant includes the same compound as the above excipient and chemically modified starch or cellulose such as sodium cross carmelose, sodium carboxymethyl starch, bridged polyvinylpyrrolidone.

The stabilizer includes, for example, paraoxybenzoates such as methylparaben, propylparaben; alcohols such as chlorobutanol, benzyl alcohol, phenylethyl alcohol, etc.; benzalconium chloride; phenols such as phenol, cresol, etc.; thimerosal; dehydroacetic acid; and sorbic acid.

For the oral application, a tablet containing excipients may be used with a granulation-binding agent as well as various disintegrants. The lubricant is very important for forming a tablet. And the same kind of a solid ingredient may be added in gelatin capsules (the preferable ingredients are lactose or milk sugar, and high molecular weight polyethyleneglycol). When an aqueous suspension and/or elixir for oral application are desirable, its active ingredient may be combined with various sweetening agent, flavor, coloring agent or dye, and if necessary, emulsifying agent, suspending agent together with a diluent. The diluent includes water, ethanol, propylene glycol, glycerin or a mixture thereof. In case of administration to an animal, the active ingredient is contained in the concentration of 5-5000 ppm, preferably 25-5000 ppm in the animal food or drinking water.

For perenteral administration (intramuscularly, intraperitoneally, intraarticularly, subcutaneously and intravenously), usually a sterilized solution for injection of the active ingredient is prepared. The compound of the present invention may be dispersed in sesame oil, arachis oil, or aqueous propyleneglycol solution. These solutions may be bufferized by adjusting pH to preferably more than 8, if necessary. These solutions are preferably made isotonic with aqueous diluent. These solutions are suitable for intravenous administration. These oily solutions are suitable for inraarticular, intramuscular or subcutaneous administration. All these solutions are prepared under sterilized condition in accordance with a conventional standard method well known in this field.

For a nasal administration or inhalation, the active compound is supplied to a patient, a solution or a suspension from a pump spray vessel which is squeezed by the patient or emitted by a pump, in aerosol spray from a pressured vessel or nebulizer, by using a suitable propellant, such as dichlorodifluoromethane, trichlorofluoromethane, dichlorotetrafluoroethane, carbon dioxide or some other suitable gus. In case of a pressured aerosol, the dosage unit can be determined by a valve supplying a calculated definite amount. The pressured vessel or nebulizer can include a solution or suspension of an active compound. Capsules or cartridges (which are prepared from gelatin, for example) for an inhalator or insufflator are prepared by admixing a compound of the present invention and a suitable powder base such as lactose or starch.

In addition, the compound of the present invention is treated with a conventional base for suppository such as cacao fat or other glyceride or ingredients used for retention type enema to prepare a suppository.

It is expected to be effective that the amount of the compound (1), its pharmaceutically acceptable salt or its prodrug is variable depending on condition of the disease, age, administration route, etc. For example, for oral administration, a lower limited dose is 0.01 mg (preferably 1 mg), and an upper limited dose is 5000 mg (preferably 500 mg), and the dose is administered once or divided several times per day per adult according to the condition of disease. For intravenous administration, a lower limited dose is 0.01 mg (preferably 0.1 mg), and an upper limited dose is 1000 mg (preferably 30 mg), and the dose is administered once or several times divided, per day per adult according to the condition of the disease.

The compound (1), its pharmaceutically acceptable salt or its prodrug is useful as a matrix metal proteinases inhibitor. Therefore, the compound is used for therapeutic and prophylactic agent for a disease related to excessive or undesirable matrix metalloproteinase.

Diseases related to excess or undesired matrix metalloproteinase include arthritis (e.g., osteoarthritis, rheumatoid arthritis), inflammatory enteropathy, Crohn's disease, emphysema, acute dyspnea syndrome, asthma, chronic obstructive disease, acute bronchitis, bronchitis, Alzheimer's disease, transplanting toxicity, cachexia, allergic reaction, allergic contact anaphylaxis, allergic conjunctive, allergic rhinitis, cancer (e.g., solid cancer such as colon cancer, breast carcinoma, lung cancer, prostata carcinoma, and malignant hemapoiesis, e.g., leukemia, lymphoma), tissue ulcer, restonosis, periodontis, eoidermolysis bulla, osteoporosis, loosening of artificial joint implants, atherosclerosis (e.g., atherosclerosic local laceration, athermanous placoido cleavage), aortic aneurysm (e.g., abdominal aneurysm and cerebral aortic aneurysm), congestive heart failure, myocardial infarction, seizure, cerebral ischemia, caput injury, myelon injury, neurodegenerative disease (acute and chronic), autoimmunity disease, Huntington disease, Parkinsonism, migraine, depression, peripheral neuropathy, pain, cerebral amyloidal avasculopathy, nootropic or performance intensity, amyotrophic lateral sclerosis, multiple sclerosis, eyepiecevasculogenesis, corneal injury, macula retinal degeneration, unusual wound healing, burn, diabetes, diabetic peripheral neuropathy, diabetic retinitis, diabetic ulcer, tumor infiltration, tumor growth, tumor metastasis, epicauma (macula), pleurisy, AIDS, sepsis, septic shock, contusion, acute infection, alcoholism, ALS, anaphylaxis, angina, hemangiofibroma, anorexia, ARDS, aspirin independent antithrombosisi, atopic dermatitis, benign vegetation, bleeding, fracture, burn, cachexia, myocardosis, cerebral apoplexy, cerebral angio dementia, CHF, chronic dermato wound, coronary thrombosis, cystic fibrosis, decubitus ulcer, Duchene's myodystorophy, emphysema, endometriosis, epidermolysis, oculopathy, fibrosis, gastritis, glomerulitis, glomerular nephritis, gout, transplantation rejection, disease of gums, GVHD, Hashimoto's disease, caput injury, head ache, angioma, hepatitis, trichauxis, hypertension, insulin resistance, spacial nephritis, ischemia, ischemic malum cordis, Kaposis sarcoma, cornification, keratitis, renal insufficiency, leishmaniasis, leprosy, leukemia, leukocyte infiltration, hepatocirrhosis, malaria, lower jaw temporomandibular arthritis, dysmnesia, meningitis, migraine, abortion, multiple cerebral infarction dementia, myodystrophy, muscle pain, myasthenia gravis, myelinosis, cardiac infarction, myopia, neovascular glaucoma, neuritis, carcinoma of eye, fasciculitis, Paget's disease, pain, pancreatis, Parkinsonism, periodontitis, peripheral disease, polyarteritis nodosa, polychondritis, premature birth, embryo membrane dehiscence, prion disease, retinitis proliferans, protein urea, pseudo gout, psoriasis, pterigium, pulmonary emphysema, radiation obstacles, rattle snake morsus(bite), Reiter's syndrome, renal fibrosis, distal occlusion, recurrent disorder, restenosis, scleritis, scleroderma, senile dementia, senility, septis, septic shock, Sharp-syndrome, Sjögren's syndrome, SLE, spondylolysis, stegnosis, infertility, seizure, thrombostasis, toxicity by chemotherapy, toxic shock, tuberculosis, uremia, vasculitis, ventricle dilation, epidermolysis bullosa and other diseases specified by expression of metalloproteinase.

The compound of the present invention may be used together with other medicament which has been used for treatment of the specified disease for the same purpose. For example, for treatment of rheumatoid arthritis or osteoarthritis, the compound of the present invention may be used together with TNFα inhibitor, anti TNF monoclonal antibody and TNF receptor immunoglobulin molecule (Enbrel: Reg. T. M.), lower dosage methotrexate, leflunomide, hydroxycycloxin, d-penicillamine, auranofin, a standard nonsteroidal anti-inflammatory agent, e.g., piroxicam, diclofenac, propionic acid, e.g., naproxen, flurbiprofen, fenbufen, ketoprofen and ibuprofen, fenamate, e.g., mefenamic acid, indomethacin, sulindac, apazone, pyrazolone, e.g., phenylbutazone, salicylic acids, e.g., aspirin, cyclooxygenase (COX)2 inhibitor, e.g., meloxicam.celecoxib and rofecoxib, analgesics and intra articular agent, e.g., corticosteroid, and hyaluronic acid, e.g., a combination of hyalgan and synvisc, etc.

The compound of the present invention may be used together with an anticancer, e.g., endostatin and angiostatin, or cytotoxic agent, such as adriamycin, daunomycin, cisplatin, etoposide, taxol, taxotere and an alkaloid, e.g., vincristine, and antimetabolite, such as methotrexate. The compound of the present invention may be also used together with acardiovascular agent, such as calcium channel blocker, hyperlipemia, such as statin, fibrate, β-blocker, an ACE inhibitor, angiotensin-2 receptor antagonist and platelet aggregation inhibitor.

The compound of the present invention may be used together with a central nervous system drug, e.g., antidepressant (e.g. sertraline), anti-Parkinson agent (e.g., deprenyl, L-dopa, requip, mirapex, MAOB inhibitor, e.g., serenzin and rasagiline, comPan inhibitor, such as A-2 inhibitor, dopamine reuptake inhibitor, NMDA antagonist, nicotine agonist, dopamine agonist, and neural oxygen-nitrogen synthesis inhibitor), and anti-alzheimer agent, such as aricept, tacrine, COX2 inhibitor, propentofylline or metrofonate.

The compound of the present invention may be used together with osteoporosis, e.g., droloxifen, fosamax, etidronate and immunosuppressant, such as FK-506 and rapamycin.

The present invention relates to also a MMP-3 and/or MMP-13 inhibitor non-selective to MMP-1 and MMP-14 containing a compound of the following formula (2), (2)

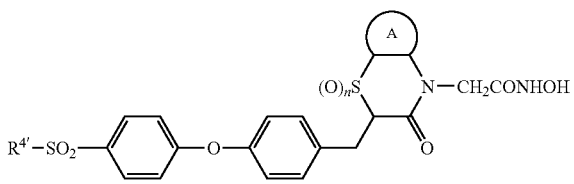

wherein ring A is optionally substituted benzene ring or 5 to 6 membered aromatic hererocycle, $R^{4'}$ is C1-4 lower alkyl group and n is an integer of 0~2.

In the formula (2), n is preferably 0, $R^{4'}$ is preferably C1-3 lower alkyl group, more preferably methyl group.

In formula (2), when ring A is substituted, the ring A may be substituted by 1~3 substituents. The substituents on the ring A are the same as ones on the above aryl group or heteroaryl group, preferably, carboxy group, cyano group, halogen atom, hydroxy group, lower alkyl group, optionally substituted lower alkyl group, lower alkoxycarbonyl group, lower alkoxy group, lower alkyl sulfonyl group, carbamoyl group, sulfamoyl group optionally substituted by lower alkyl group, especially preferably, carboxy group, optionally substituted lower alkyl group. Substituents on the said lower alkyl group include hydroxy group, lower alkoxy group, carboxy group, carbamoyl group optionally substituted by lower alkyl group, lower alkoxycarbonyl group, etc.

In the formula (2), the ring A is preferably benzene, pyridine, thiophene, or pyrazole. Preferable embodiments of compounds of the formula (2) are illustrated as following formula (3) or (4).

(3)

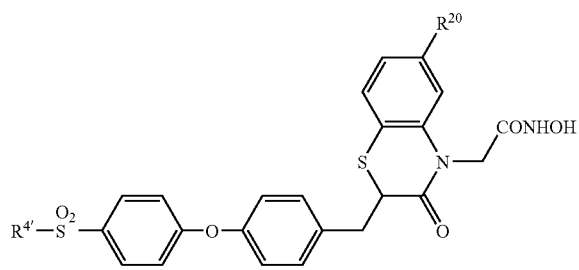

(4)

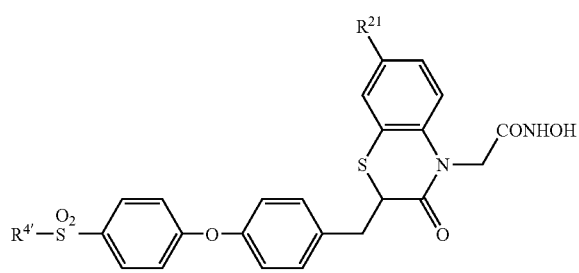

wherein $R^{4'}$ is the same as defined above, $R^{20}$ and $R^{21}$ are the same as substituents on the ring A.

The compound of the formula (2) is administered in the same manner as in the above compound (1).

The compound of the formula (2) is known and is prepared by the method described in WO 00/63197.

EXAMPLE

The present invention is in detail explained by the following examples, but the invention is not limited by these examples.

The following examples show the process for preparation of the compound of the present invention. NMR data are reported in ppm (δ), and are referenced to the deuterium lock signal from the sample solvent. The commercially available regents were used without further purification. The room temperature or ambient temperature means 20° C. to 30° C. All non-aqueous reactions were run under nitrogen atmosphere. The concentration under reduced pressure was carried out by a rotary evaporator.

The obtained object compound is separated or purified by for example, if necessary, recrystalization, reprecipitation or the method usually used in separation or purification of an organic compound, such as absorption column chromatography using a carrier such as silica gel, alumina, Florisil such as magnesium silica gel;the method using a synthetic observant such as partition column chromatography using a carrier such as cephadex LH-20 (Pharmacia), Amberlite XAD-11 (Rohm and Haas), or DiaionHP-20 (Mitsubishi Chemical), the method using ion exchange chromatography, or normal phase-reverse column chromatography with silica gel or lower alkylated silica gel (preferably, high performance liquid chromatography.) and in combination of these method, if necessary, and by eluting with an appropriate solvent.

Example 1

Synthesis of 4-(4-methylsulfonylphenoxy)phenylsulfonyl chloride

Step (i)

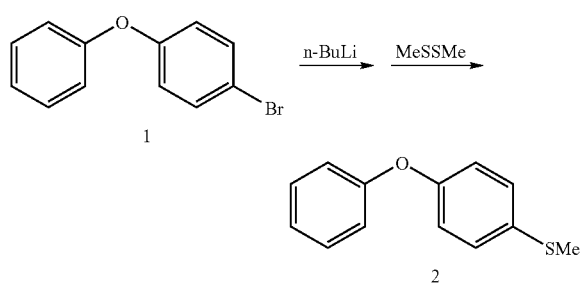

Compound 1 (69 g) in THF (350 ml) was cooled at inner temperature of −70° C. under nitrogen atmosphere. Thereto was dropped n-butyllithium in hexane (f=1.56, 187 ml) at inner temperature of less than −65° C. After dropping off, the mixture was stirred for 1 hour at the same temperature. Then, methyldisulfide (26.2 ml) was dropped thereto at inner temperature of less than −60° C. The stirring was continued and the temperature was gradually raised to room temperature. After stirring overnight, to the reaction mixture was added water (50 ml) and the reaction was quenched. The reaction mixture was concentrated under reduced pressure, and the residue was extracted with ammonium chloride solution and ethyl acetate. The organic layer was washed, dried over sodium sulfate, and was concentrated under reduced pressure, and the residue was purified with silica gel column chromatography (hexane/ethyl acetate=9/1) to give compound 2 (61.7 g, pale yellow liquid).

Step (ii)

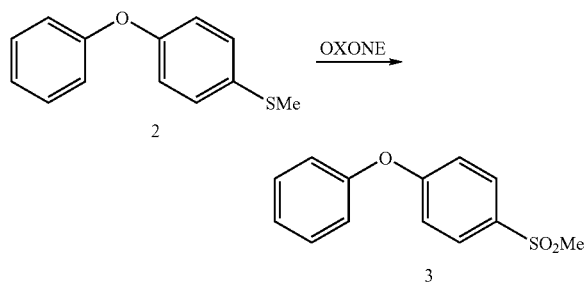

To a mixture of compound 2 (20 g), ethyl acetate (250 ml), methanol (250 ml) and water (200 ml) was added OXONE (Reg. T. M.) (122 g, Aldrich) dividedly. After stirring for 3 hours, to the reaction mixture was added ethyl acetate (200 ml) and the precipitate was filtered off. The filtrate was concentrated under reduced pressure and then thereto was added water. The solution was extracted with ethyl acetate. The organic layer was washed with water and then, dried over sodium sulfate and concentrated under reduced pressure. Thus obtained white solid was twice dried under reduced pressure to give compound 3 (46 g). Step(iii)

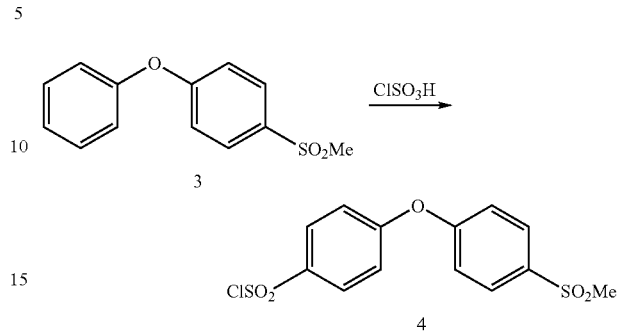

Chlorosulfuric acid (60 g) was stirred under nitrogen atmosphere under ice cooling. Thereto was added compound 3 (20 g) and the mixture was allowed to stand to room temperature. After stirring for over night, the reaction mixture was poured on ice water (500 ml). The resulting white solid was filtered, washed with water, and dried under reduced pressure to give compound 4 (21 g, 77%) as a white solid. $^1$H-NMR (DMSO-D$_6$) δ3.19 (s, 3H), 7.09 (m, 2H), 7.17 (m, 2H), 7.67 (m, 2H), 7.90 (m, 2H)

Example 2

Synthesis of N-hydroxy 1-[isobutyl({4-[4-(methylsulfonyl)phenoxy]phenyl}sulfonyl)amino]cyclopentanecarboxamide

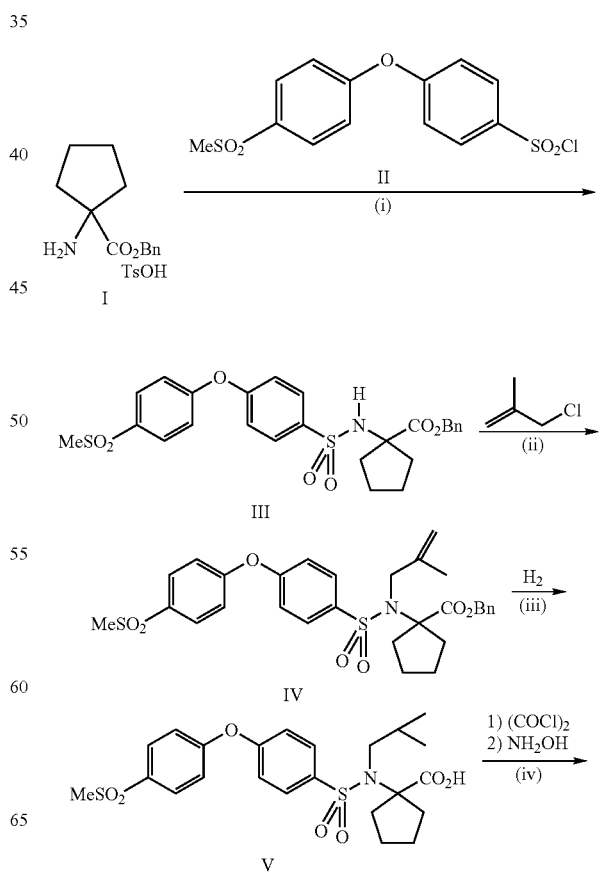

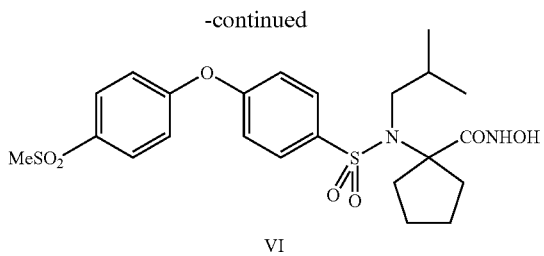

VI

Step (i)

A mixture of compound I (37 g), diisopropylethylamine (35 ml), and dimethylformamide (400 ml) was stirred at 0° C. Thereto was dividedly added compound II (33 g). During stirring overnight, it was raised to room temperature. After adding an aqueous hydrochloric acid solution, the mixture was extracted with ethyl acetate. The organic layer was separated, washed successively with an aqueous potassium carbonate solution and brine, and dried over sodium sulfate, and concentrated under reduced pressure to give compound III (37.6 g).

Step (ii)

To compound III (37.6 g) were added dimethylformamide (200 ml), β-methacryl chloride (8.36 g), potassium carbonate (14.72 g) and potassium iodide (1.18 g) and then, during stirring at 70° C. for 14 hours it was cooled to room temperature. The mixture was extracted with ethyl acetate and water. The organic layer was washed with brine, dried over sodium sulfate, and concentrated under reduced pressure. The residue was purified with silica gel column chromatography (eluting solvent: hexane/ethyl acetate=7/3 to 6/4) to give compound IV (38.2 g).

Step (iii)

To compound IV (38.2 g) were added ethyl acetate (300 ml) and 5% palladium/carbon (2 g) and the mixture was stirred at room temperature under hydrogen atmosphere at normal pressure for 8 hours. Then catalyst was filtered off with celite under reduced pressure to give compound V (32.1 g).

Step (iv)

To compound (32.1 g) in dichloromethane (400 ml) was added dimethylformamide (0.1 g) and the mixture was stirred at 0° C. Thereto was added oxalyl chloride (7.46 ml). One hour later, the mixture was raised to room temperature and stirred for 6 hours. After concentration under reduced pressure, to the residue was added tetrahydrofuran (250 ml). This solution was dropped at 0° C. to a mixture of hydroxylamine hydrochloride (22.9 g), sodium hydrogencarbonate (38.8 g), tetrahydrofuran (200 ml), and water (20 ml) under stirring. After concentrating the reaction solution under reduced pressure, the mixture was extracted with ethyl acetate and aqueous hydrochloric acid. The organic layer was dried over sodium sulfate and concentrated under reduced pressure. The residue was purified with silica gel column chromatography (eluting solvent: hexane/ethyl acetate=4/6 to 3/7), to give compound VI (32.4 g).

$^1$H-NMR (DMSO-D$_6$) δ0.83 (d, J=6.4 Hz, 6H), 1.47 (m, 2H), 1.57 (m, 2H), 1.83 (m, 2H), 1.95 (m, 1H), 2.29 (m, 2H), 3.18 (d, J=7.2 Hz, 2H), 3.23 (s, H), 7.24-7.33 (m, 4H), 7.84 (m, 2H), 7.97 (m, 2H), 8.78 (s, 1H), 10.30 (s, 1H)

Example 3

Synthesis of N$^1$-hydroxy-N$^2$-(2-isopropoxyethyl)-N$^2$-({4-[4-(methylsulfonyl)phenoxy]phenyl}sulfonyl)glycinamide

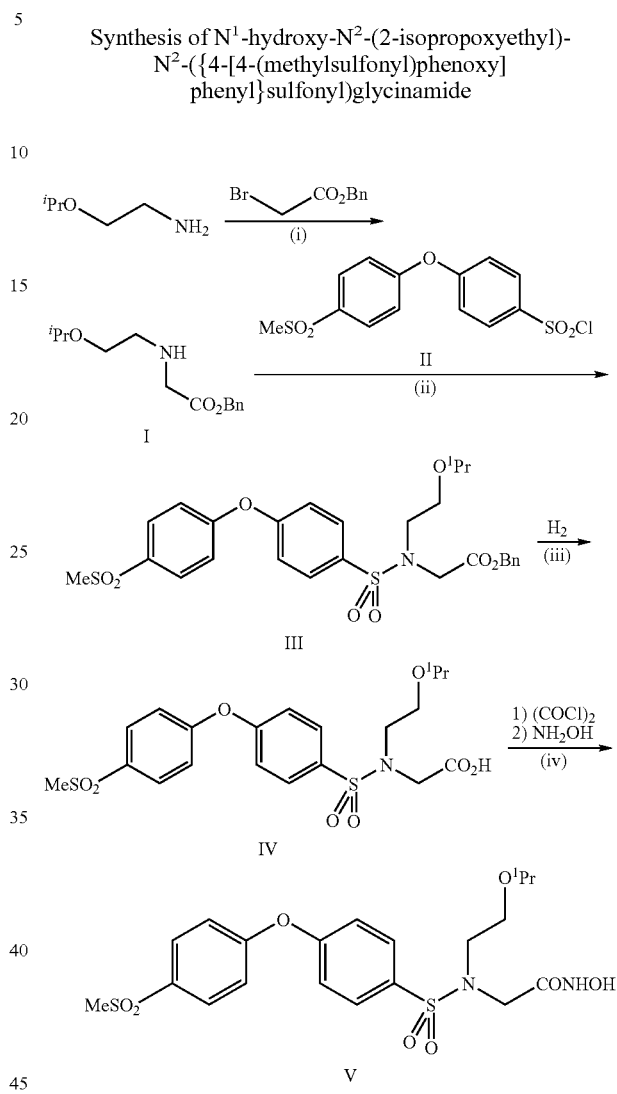

Step (i)

2-Isopropoxyethylamine (2.5 g), diisopropylethylamine (4.22 ml), and dimethylformamide (30 ml) were stirred at 0° C., and thereto was dropped benzyl bromoacetate (3.3 ml). The mixture was raised to room temperature and 8 hours later, and extracted with ethyl acetate and brine with a separating funnel. The organic layer was dried over sodium sulfate and concentrated under reduced pressure. The residue was purified by silica gel column chromatography (eluting solvent: hexane/ethyl acetate=1/4) to give compound I (4.3 g).

Step (ii)

To a mixture of compound I (1 g), diisopropylethylamine (1.4 ml), and dimethylformamide (30 ml) was dividedly added at 0° C. compound II (1.4 g). The mixture was raised to room temperature and 12 hours later, and extracted with ethyl acetate and aqueous hydrochloric acid with a separating funnel. The organic layer was dried over sodium sulfate and concentrated under reduced pressure. The residue was purified with silica gel column chromatography (eluting solvent: hexane/ethyl acetate=1/1) to give compound III (1.5 g).

Step (iii)

To compound III (1.47 g) were added ethyl acetate (30 ml) and 5% palladium/carbon (0.1 g), and the mixture was stirred for 8 hours at room temperature under hydrogen atmosphere under normal pressure and then, catalyst was filtered off with celite. The solution was concentrated under reduced pressure to give compound IV (1.2 g).

Step (iv)

To compound IV (1.19 g) were added dichloromethane (20 ml) and dimethylformamide (10 mg) and then, thereto was added at 0° C. oxalyl chloride (0.3 ml). After stirring at room temperature for 5 hours, the mixture was concentrated under reduced pressure. To the residue was added tetrahydrofuran (15 ml). The solution was added at 0° C. to a mixture of hydroxylamine hydrochloride (0.9 g), sodium hydrogencarbonate (1.5 g), tetrahydrofuran (20 ml) and water (5 ml) under stirring. The reaction solution was extracted with ethyl acetate and aqueous hydrochloric acid. The organic layer was dried over sodium sulfate and concentrated under reduced pressure. The residue was crystallized from chloroform to give compound V (0.8 g).

$^1$H-NMR (DMSO-D$_6$) δ1.02 (d, J=6.0 Hz, 6H), 3.23 (s, 3H), 3.33 (m, 2H), 3.48 (m, 3H), 3.81 (m, 2H), 7.26-7.33 (m, 4H), 7.90 (m, 2H), 7.98 (m, 2H), 8.90 (s, 1H), 10.53 (s, 1H)

Example 4

Synthesis of N-{4-[(hydroxyamino)carbonyl]tetrahydoro-2H-pyran-4-yl}-N-({4-[4-(methylsulfonyl)phenoxy]phenyl}sulfonyl)-β-alaninedimethylamide

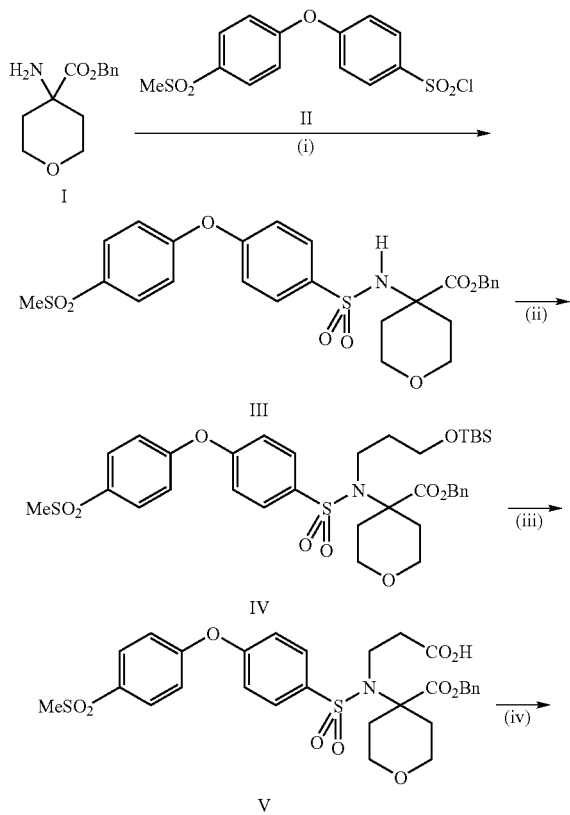

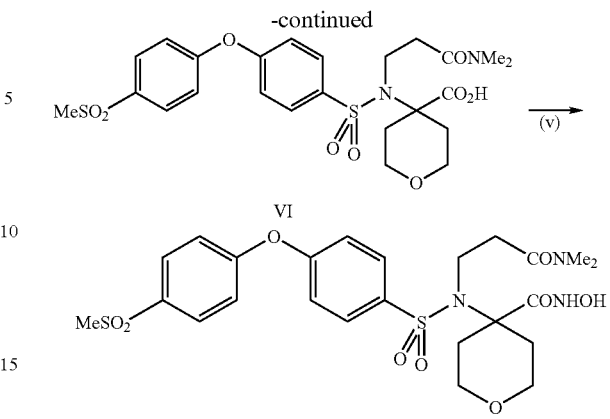

Step (i)

Compound I (4 g), diisopropylethylamine (5.9 ml) and tetrahydrofuran (100 ml) were stirred at 0° C. and thereto was dividedly added compound II (6.0 g). After 4 hours the reaction mixture was concentrated under reduced pressure. The residue was extracted with ethyl acetate and brine. The organic layer was dried over sodium sulfate and concentrated under reduced pressure. The residue was purified with silica gel column chromatography (eluting solvent: hexane/ethyl acetate=2/1, 1/2) to give compound III (3.0 g).

Step (ii)

Potassium hexamethyldisilazide (1.5 g) was added to compound III (3.0 g) in dimethylformamide (50 ml) under stirring at 0° C. After 10 minutes, the mixture was raised to room temperature and 90 minutes later, 3-(tert-butyl dimethylsilyl) oxy-1-iodopropane (2.12 g) in dimethylformamide (5 ml) was added thereto. After stirring for 2 days, the reaction mixture was extracted with ethyl acetate and brine, and the extract was dried over sodium sulfate and concentrated under reduced pressure. The residue was purified with silica gel column chromatography (eluting solvent: hexane/ethyl acetate=2/1, 1/2, 0/1) to give compound IV (1.2 g) together with an alcohol, namely a desilicated compound of compound IV (0.6 g).

Step (iii)

To compound IV (1.17 g) in dichloromethane (50 ml) was added at 0° C. trifluoroboran-diethyl ether complex (0.43 ml). After 2 hours, the mixture was extracted with 0.5N hydrochloric acid and chloroform with a separating funnel and the extract was dried over sodium sulfate and concentrated under reduced pressure.

To this residue were added the alcohol compound (0.6 g) prepared in the step (ii) and acetone (40 ml). To this solution was added at room temperature Jone's reagent until the mixture became orange color. After 20 minutes the precipitate was filtered off with celite, and the filtrate was extracted with ethyl acetate and water with a separating funnel. The organic layer was concentrated under reduced pressure and then, extracted with toluene and aqueous potassium carbonate solution. The water layer was acidified with aqueous hydrochloric acid and extracted with ethyl acetate. The organic layer was dried over sodium sulfate and concentrated under reduced pressure to give compound V (1.24 g).

Step (iv)

Isopropylchloroformate (0.1 ml) was dropped to a mixture solution of compound V (0.47 g), N-methylmorpholine (0.25 ml), and tetrahydrofuran (30 ml) at −15° C. After 15 minutes, dimethylamine in tetrahydrofuran (2 M, 0.76 ml) was added thereto. After 30 minutes, the mixture was extracted with aqueous hydrochloric acid and ethyl acetate with a separating funnel. The organic layer was dried over sodium sulfate and concentrated under reduced pressure. The residue was purified with silica gel column chromatography (eluting solvent: hexane/ethyl acetate=1/4). To the purified amide compound were added ethyl acetate (30 ml) and 5% palladium/carbon (80 mg) and the mixture was stirred at room temperature under hydrogen atmosphere under normal pressure. After 4 hours, catalyst was filtered off with celite and the filtrate was concentrated under reduced pressure to give compound VI (0.4 g).

Step (v)

To compound VI (0.42 g) and diisopropylamine(0.15 ml) in dimethylformamide (10 ml) was added at room temperature O-(1H-benzotriazol-1-yl)-N,N,N',N'-tetramethyluroniumhexafluorophosphate (HBTU, 0.3 g). After 3 hours, thereto were added diisopropylamine (0.3 ml) and O-benzyl hydroxylamine hydrochloride (0.2 g), and the mixture was stirred at 80° C. for 12 hours. Then the mixture was cooled to room temperature and extracted with ethyl acetate and bicarbonate with a separating funnel. The organic layer was washed successively with aqueous hydrochloric acid and brine, dried over sodium sulfate and concentrated under reduced pressure. The residue was purified with silica gel column chromatography (eluting solvent: methanol/ethyl acetate=0/1, 1/100). To the purified product were added tetrahydrofuran (10 ml), methanol (20 ml) and 5% palladium/carbon (0.1 g) and the mixture was stirred for 4 hours at room temperature under hydrogen atmosphere under normal pressure. Catalyst was filtered off and the filtrate was concentrated under reduced pressure to give compound VII (0.1 g).

$^1$H-NMR (DMSO-D$_6$) δ1.91 (m, 2H), 2.29 (m, 2H), 2.67 (m, 2H), 2.79 (s, 3H), 2.94 (s, 3H), 3.23 (s, 3H), 3.38 (t, J=10.8 Hz, 2H), 3.49 (m, 2H), 3.71 (m, 2H), 7.28 (m, 2H), 7.33 (m, 2H), 7.89 (m, 2H), 7.98 (m, 2H), 8.96 (s, 1H), 10.69 (s, 1H)

Among compounds of Example 5-48, compounds of Example 5-7, 9-24, 32-35, 37-38, 41-42 and 46-48 were prepared in the same manner as in Example 2, and compounds of Example 8, 36, 39-40 and 43-44 were prepared in the same manner as in Example 3 and compounds of Example 25-31 and 45 were prepared in the same manner as in Example 4.

Example 5

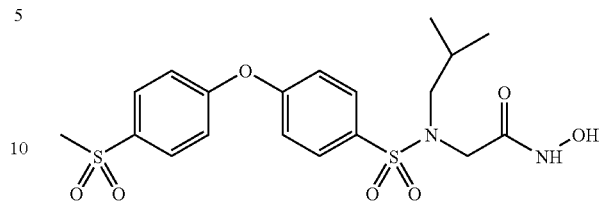

N$^{1'}$-Hydroxy-N$^{2'}$-isobutyl-N$^{2'}$-({4-[4-(methylsulfonyl)phenoxy]phenyl}sulfonyl)glycinamide $^1$H-NMR (DMSO-D$_6$) δ0.82 (d, J=6.8 Hz, 6H), 1.85 (m, 1H), 2.92 (d, J=7.6 Hz, 2H), 3.23 (s, 3H), 3.71 (s, 2H), 7.23-7.31 (m, 4H), 7.87 (m, 2H), 7.97 (m, 2H), 8.91 (s, 1H), 10.58 (s, 1H).

Example 6

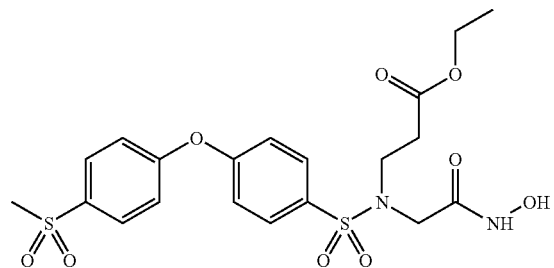

Ethyl N-[2-(hydroxyamino)-2-oxoethyl]-N-({4-[4-(methylsulfonyl)phenoxy]phenyl}sulfonyl)-β-alaninate $^1$H-NMR (DMSO-D$_6$) δ1.17 (t, J=7.2 Hz, 3H), 2.63 (t, J=7.6 Hz, 2H), 3.23 (s, 3H), 3.41 (t, J=7.6 Hz, 2H), 3.79 (s, 2H), 4.04 (q, J=7.2 Hz, 2H), 7.23-7.34 (m, 4H), 7.88 (m, 2H), 7.98 (m, 2H), 8.94 (s, 1H), 10.62 (s, 1H).

Example 7

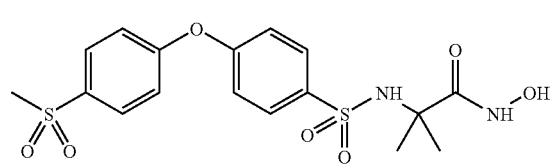

N^{1'}-Hydroxy-2-methyl-N^{2'}-({4-[4-(methylsulfonyl)phenoxy]phenyl}sulfonyl)alaninamide ¹H-NMR (DMSO-D$_6$) δ1.25 (s, 6H), 3.22 (s, 3H), 7.25-7.31 (m, 4H), 7.80 (br, 1H), 7.88 (m, 2H), 7.96 (m, 2H), 8.74(s, 1H), 10.40 (s, 1H).

Example 8

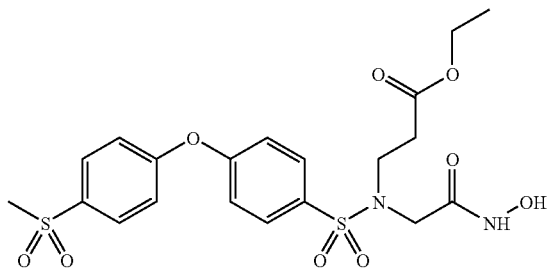

Ethyl N-[2-(hydroxyamino)-2-oxoethyl]-N-({4-[4-(methylsulfonyl)phenoxy]phenyl}sulfonyl)-β-alaninate ¹H-NMR (DMSO-D$_6$) δ1.17 (t, J=7.2 Hz, 3H), 2.63 (t, J=7.6 Hz, 2H), 3.23 (s, 3H), 3.41 (t, J=7.6 Hz, 2H), 3.79(s, 2H), 4.04 (q, J=7.2 Hz, 2H), 7.23-7.34 (m, 4H), 7.88 (m, 2H), 7.98 (m, 2H), 8.94 (s, 1H), 10.62 (s, 1H).

Example 9

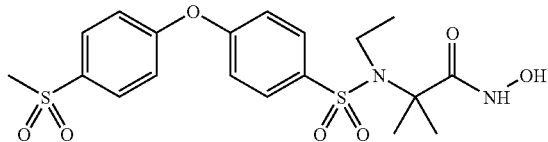

N^{1'}-Hydroxy-N^{2'}-ethyl-2-methyl-N^{2'}-({4-[4-(methylsulfonyl)phenoxy]phenyl}sulfonyl)alaninamide ¹H-NMR (DMSO-D$_6$) δ1.12 (t, J=6.8 Hz, 3H), 3.19-3.24 (m, 5H), 7.25-7.33 (m, 4H), 7.96-8.03 (m, 4H), 8.76 (s, 1H), 10.39 (s, 1H).

Example 10

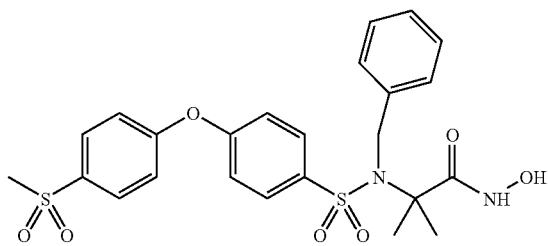

N^{2'}-Benzyl-N^{1'}-hydroxy-2-methyl-N^{2'}-({4-[4-(methylsulfonyl)phenoxy]phenyl}sulfonyl)alaninamide ¹H-NMR (DMSO-D$_6$) δ1.46 (s, 6H), 3.23 (s, 3H), 4.56 (s, 2H), 7.17-7.24 (m, 7H), 7.32 (m, 2H), 7.94-7.99 (m, 4H), 8.78 (s, 1H), 10.41 (s, 1H).

Example 11

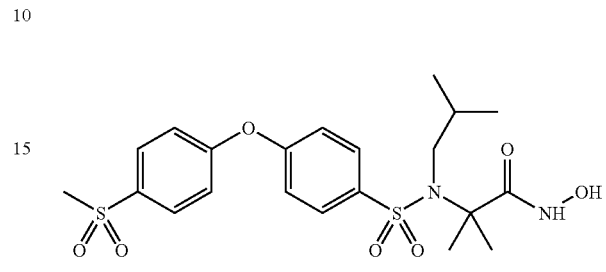

N^{1'}-Hydroxy-N^{2'}-isobutyl-2-methyl-N^{2'}-({4-[4-(methylsulfonyl)phenoxy]phenyl}sulfonyl)alaninamide ¹H-NMR (DMSO-D$_6$) δ0.74 (d=6.8 Hz, 6H), 1.45 (s, 6H), 1.86 (m, 1H), 3.07 (d, J=7.6 Hz, 2H), 3.23 (s, 3 H), 7.25-7.30 (m, 4H), 7.96-7.99 (m, 4H), 8.75 (s, 1H), 10.36 (s, 1H).

Example 12

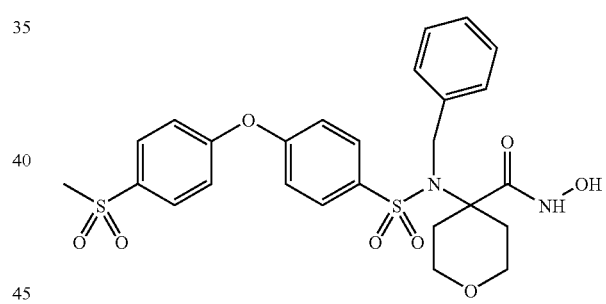

4-[Benzyl({4-[4-(methylsulfonyl)phenoxy]phenyl}sulfonyl)amino]-N-hydroxytetrahydoro-2H-pyrane-4-carboxamide ¹H-NMR (DMSO-D$_6$) δ1.82 (m, 2H), 2.38 (m, 2H), 3.23 (s, 3H), 3.64 (m, 2H), 4.68 (s, 2H), 7.22-7.39 (m, 9H), 7.88 (m, 2H), 7.97 (m, 2H), 8.92 (s, 1H), 10.68 (s, 1H).

Example 13

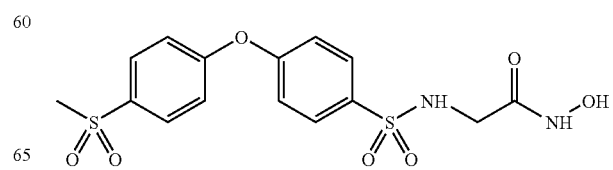

N[1']-Hydroxy-N[2']-({4-[4-(methylsulfonyl)phenoxy]phenyl}sulfonyl)glycinamide $^1$H-NMR (DMSO-D$_6$) δ3.26 (s, 3H), 3.35 (s, 2H), 7.28-7.32(m, 4H), 7.85 (m, 2H), 7.96 (m, 2H), 8.02 (brs, 1H), 8.88 (s, 1H), 10.56 (s, 1H).

Example 14

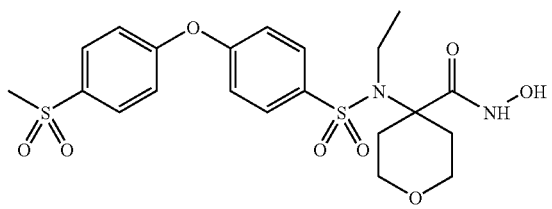

4-[Ethyl({4-[4-(methylsulfonyl)phenoxy]phenyl}sulfonyl)-N-hydroxytetrahydro-2H-pyrane-4-carboxamide $^1$H-NMR (DMSO-D$_6$) δ1.16 (t, J=6.8 Hz, 3H), 1.90 (m, 2H), 2.30 (m, 2H), 3.23 (s, 3H), 3.36(q, J=6.8 Hz, 2H), 3.72 (m, 2H), 7.26-7.35 (m, 4H), 7.90 (m, 2H), 7.97 (m, 2H), 8.94 (s, 1H), 10.65 (s, 1H).

Example 15

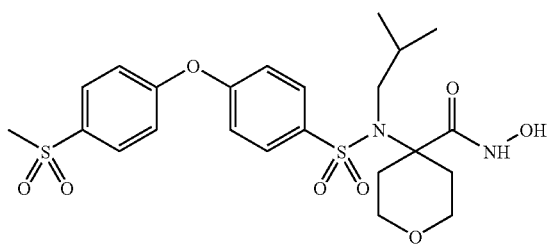

N-Hydroxy-4-[isobutyl({4-[4-(methylsulfonyl)phenoxy]phenyl}sulfonyl)amino]tetrahydro-2H-pyrane-4-carboxamide $^1$H-NMR (DMSO-D$_6$) δ0.84 (d, J=6.8 Hz, 6H), 1.82-2.02 (m, 3H), 2.27 (m, 2H), 3.18-3.32 (m, 7H), 3.72 (m, 2H), 7.28-7.33 (m, 4H), 7.85 (m, 2H), 7.98 (m, 2H), 8.95 (s, 1H), 10.65 (s, 1H).

Example 16

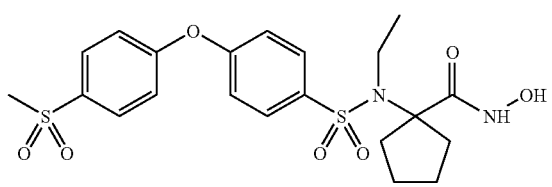

1-[Ethyl({4-[4-(methylsulfonyl)phenoxy]phenyl}sulfonyl)amino]-N-hydroxycyclopentanecarboxamide $^1$H-NMR (DMSO-D$_6$) δ1.15 (t, J=7.2 Hz, 6H), 1.47-1.62 (m, 4H), 1.90 (m, 2H), 2.30(m, 2H), 3.23(s, 3H), 3.37(q, J=7.2 Hz, 2H), 7.25(m, 2H), 7.31 (m, 2H), 7.90 (m, 2H), 7.97 (m, 2H), 8.77 (s, 1H), 10.34 (s, 1H).

Example 17

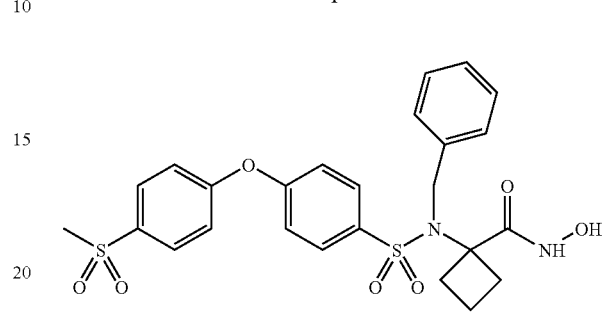

1-[Benzyl({4-[4-(methylsulfonyl)phenoxy]phenyl}sulfonyl)amino]-N-hydroxycyclobutanecarboxamide $^1$H-NMR (DMSO-D$_6$) δ1.68 (m, 2H), 2.40 (m, 4H), 3.24 (s, 3H), 4.56 (m, 2H), 7.16 (m, 2H), 7.27-7.36 (m, 4H), 7.69 (m, 2H), 7.97 (m, 2H), 8.89 (s, 1H), 10.80 (s, 1H).

Example 18

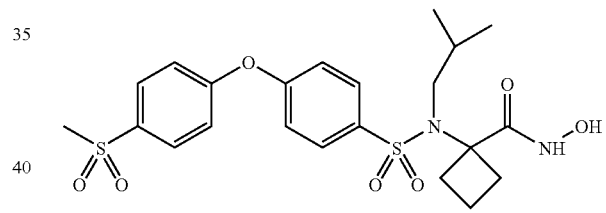

N-Hydroxy-1-[isobutyl({4-[4-(methylsulfonyl)phenoxy]phenyl}sulfonyl)amino]cyclobutanecarboxamide $^1$H-NMR (DMSO-D$_6$) δ0.85 (d, J=6.4 Hz, 6H), 1.66 (m, 2H), 1.89 (m, 1H), 2.36 (m, 4H), 2.97 (d, J=7.6 Hz, 2H), 3.23 (s, 3H), 7.25 (m, 2H), 7.32 (m, 2H), 7.82 (m, 2H), 7.97 (m, 2H), 8.88 (s, 1H), 10.58 (s, 1H).

Example 19

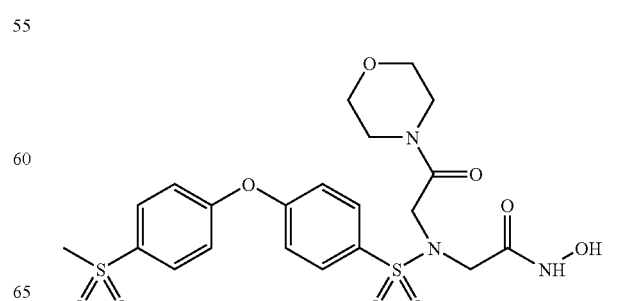

N-{1-[(Hydroxyamino)carbonyl]methyl}-N-({4-[4-(methylsulfonyl)phenoxy]phenyl}sulfonyl)-glycine morpholinoamide ¹H-NMR (DMSO-D₆) δ3.23 (s, 3H), 3.41 (m, 4H), 3.56 (m, 4H), 3.81 (s, 2H), 4.29 (s, 2H), 7.26-7.32 (m, 4H), 7.91 (m, 2H), 7.97 (m, 2H), 8.90 (s, 1H), 10.90 (s, 1H).

Example 20

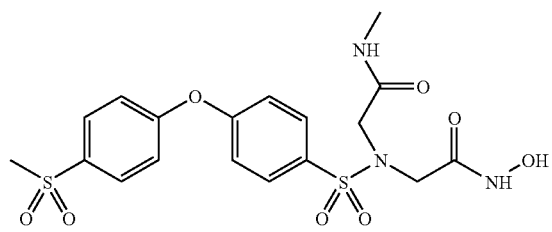

N'¹'-Hydroxy-N'²'-[2-(methylamino)-2-oxoethyl]-N'²'-({4-[4-(methylsulfonyl)phenoxy]phenyl}sulfonyl)glycinamide ¹H-NMR (DMSO-D₆) δ2.60 (d, J=4.4 Hz, 3H), 3.23 (s, 3H), 3.83 (s, 2H), 3.85 (s, 2H), 7.32 (m, 4H), 7.89 (m, 2H), 7.98 (m, 2H), 8.54 (br, 1H), 9.03 (s, 1H), 11.09 (s, 1H).

Example 21

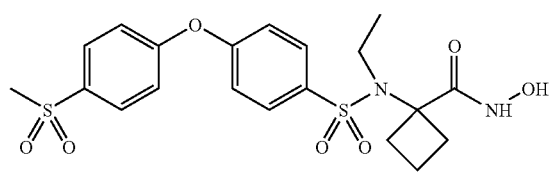

1-[Ethyl({4-[4-(methylsulfonyl)phenoxy]phenyl}sulfonyl)amino]-N-hydroxycyclobutanecarboxamide ¹H-NMR (DMSO-D₆) δ1.15 (t, J=7.2 Hz, 3H), 1.69 (m, 2H), 2.40 (m, 4H), 3.23 (s, 3H), 3.26 (q, J=7.2 Hz, 2H), 7.24 (m, 2H), 7.32 (m, 2H), 7.842 (m, 2H), 7.97 (m, 2H), 8.87 (s, 1H), 10.59 (s, 1H).

Example 22

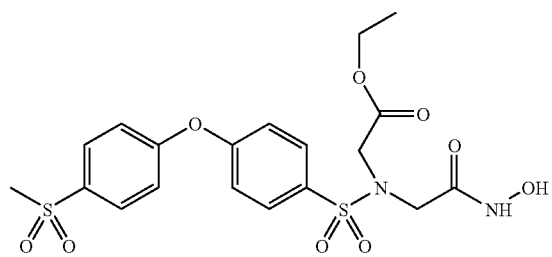

Ethyl N-{[(hydroxyamino)carbonyl]methyl}-N-({4-[4-(methylsulfonyl)phenoxy]phenyl}sulfonyl)-glycinate ¹H-NMR (DMSO-D₆) δ1.14 (t, J=7.2 Hz, 3H), 3.23 (s, 3H), 3.86 (s, 2H), 4.04 (q, J=7.2 Hz, 2H), 4.17 (s, 2H), 7.26-7.32 (m, 4H), 7.89 (m, 2H), 7.98 (m, 2H), 8.94 (s, 1H), 10.61 (s, 1H).

Example 23

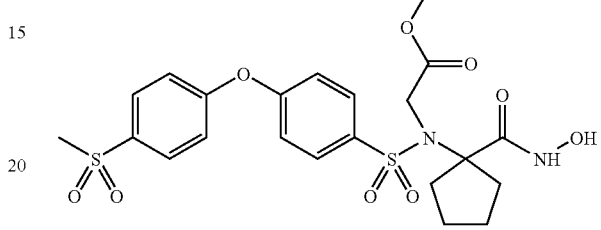

Ethyl N-{1-[(hydroxyamino)carbonyl]cyclopentyl}-N-({4-[4-(methylsulfonyl)phenoxy]phenyl}sulfonyl) glycinate ¹H-NMR (DMSO-D₆) δ1.17 (t, J=7.2 Hz, 3H), 1.53 (m, 4H), 1.89 (m, 2H), 2.23 (m, 2H), 3.23 (s, 3H), 4.02 (q, J=7.2 Hz, 2H), 4.29 (s, 2H), 7.26 (m, 2H), 7.31 (m, 2H), 7.92 (m, 2H), 7.98 (m, 2H), 8.87 (s, 1H), 10.42 (s, 1H).

Example 24

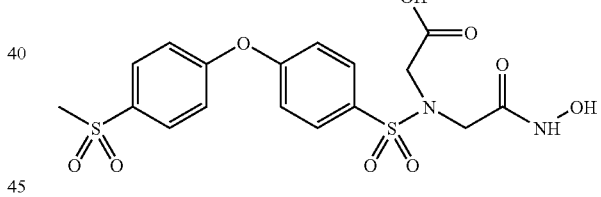

N-{[(Hydroxyamino)carbonyl]methyl}-N-({4-[4-(methylsulfonyl)phenoxy]phenyl}sulfonyl)-glycine ¹H-NMR (DMSO-D₆) δ3.23 (s, 3H), 3.88 (s, 2H), 4.07 (s, 2H), 7.26-7.32 (m, 2H), 7.90 (m, 2H), 7.97 (m, 2H), 8.99+9.24 (s, 1H), 10.23+10.70 (s, 1H), 13.02 (br, 1H).

Example 25

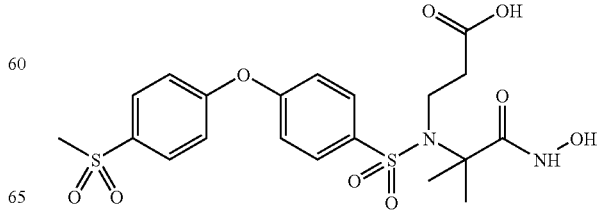

N-{[(Hydroxyamino)carbonyl]-dimethylmethyl}-N-({4-[4-(methylsulfonyl)phenoxy]phenyl}sulfonyl)-β-alanine ¹H-NMR (DMSO-D₆) δ1.46 (s, 6H), 2.60 (m, 2H), 3.23 (s, 3H), 3.38 (m, 2H), 7.26-7.34 (m, 4H), 7.96-8.00 (m, 4H), 8.80 (s, 1H), 10.41 (s, 1H), 12.31 (brs, 1H).

Example 26

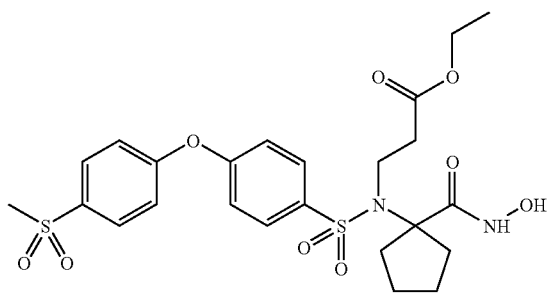

Ethyl N-{1-[(hydroxyamino)carbonyl]cyclopentyl}-N-({4-[4-(methylsulfonyl)phenoxy]phenyl}sulfonyl)-β-alaninate ¹H-NMR (DMSO-D₆) δ1.18 (t, J=7.2 Hz, 3H), 1.55 (m, 4H), 1.89 (m, 2H), 2.26 (m, 2H), 2.71 (m, 2H), 3.23 (s, 3H), 3.54 (m, 2H), 4.05 (q, J=7.2 Hz, 2H), 7.26-7.34 (m, 4H), 7.89 (m, 2H), 7.98 (m, 2H), 8.80 (s, 1H), 10.43 (s, 1H).

Example 27

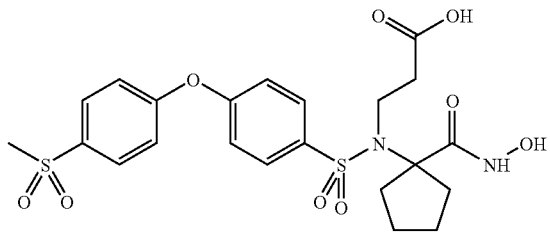

N-{1-[(Hydroxyamino)carbonyl]cyclopentyl}-N-({4-[4-(methylsulfonyl)phenoxy]phenyl}sulfonyl)-β-alanine 1H-NMR (DMSO-D₆) δ1.56 (m, 4H), 1.90 (m, 2H), 2.26 (m, 2H), 2.63 (m, 2H), 3.23 (s, 3H), 3.50 (m, 2H), 4.05 (q, J=7.2 Hz, 2H), 7.27 (m, 4H), 7.32 (m, 4H), 7.89 (m, 2H), 7.98 (m, 2H), 8.80 (s, 1H), 10.44 (s, 1H), 12.31 (brs, 1H).

Example 28

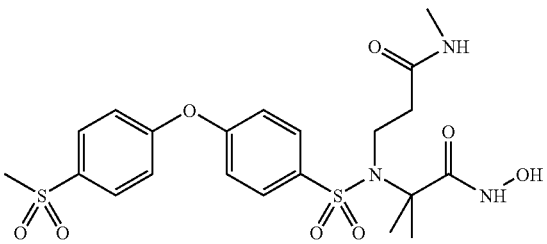

N$^{t3'}$-[2-(Hydroxyamino)-2-oxo-1,1-dimethylethyl]-N$^{t1'}$-methyl-N$^{t3'}$-({4-[4-(methylsulfonyl)phenoxy]phenyl}sulfonyl)-β-alaninamide ¹H-NMR (DMSO-D₆) δ1.47 (s, 6H), 2.45 (s, 3H), 2.55 (m, 2H), 3.23 (s, 3H), 3.37 (m, 2H), 7.26-7.35 (m, 4H), 7.82 (m, 1H), 7.97-8.00 (m, 4H), 8.77 (s, 1H), 10.43 (s, 1H).

Example 29

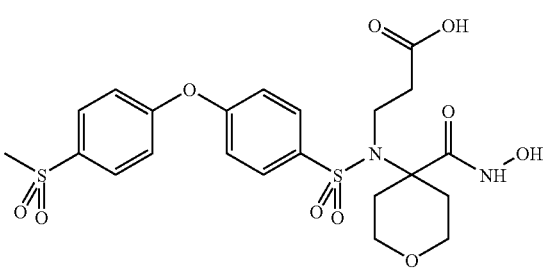

N-{4-[(Hydroxyamino)carbonyl]tetrahydoro-2H-pyran-4-yl}-N-({4-[4-(methylsulfonyl)phenoxy]phenyl}sulfonyl)-β-alanine ¹H-NMR (DMSO-D₆) δ1.89 (m, 2H), 2.28 (m, 2H), 2.62 (m, 2H), 3.23 (s, 3H), 3.37 (m, 2H), 3.50 (m, 2H), 3.71 (m, 2H), 7.26-7.39 (m, 4H), 7.90 (m, 2H), 7.98 (m, 2H), 8.97 (s, 1H), 10.69 (s, 1H), 12.28 (brs, 1H).

Example 30

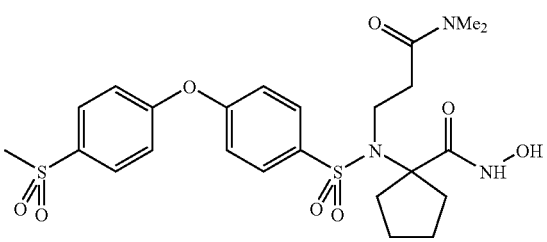

N-{1-[(Hydroxyamino)carbonyl]cyclopentyl}-N-({4-[4-(methylsulfonyl)phenoxy]phenyl}sulfonyl)-β-alanine dimethylamide $^1$H-NMR (DMSO-D$_6$) 1.55 (m, 4H), 1.89 (m, 2H), 2.28 (m, 2H), 2.69 (m, 2H), 2.78 (s, 3H), 2.93 (s, 3H), 3.23 (s, 3H), 3.48 (m, 2H), 7.26 (m, 2H), 7.32 (m, 2H), 7.88 (m, 2H), 7.98 (m, 2H), 8.76 (s, 1H), 10.36 (s, 1H).

Example 31

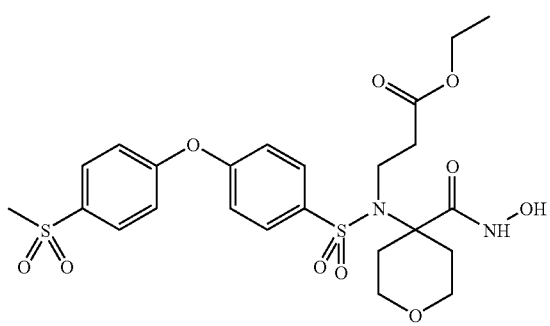

Ethyl N-{4-[(hydroxyamino)carbonyl]tetrahydro-2H-pyran-4-yl}-N-({4-[4-(methylsulfonyl)phenoxy]phenyl}sulfonyl)-β-alaninate $^1$H-NMR (DMSO-D$_6$) 1.19 (t, J=6.82 Hz, 3H), 1.88 (m, 2H), 2.28 (m, 2H), 2.69 (m, 2H), 3.23 (s, 3H), 3.36 (m, 2H), 3.53 (m, 2H), 3.70 (m, 2H), 4.05 (q, J=6.8 Hz, 2H), 7.27-7.35 (m, 4H), 7.90 (m, 2H), 7.98 (m, 2H), 8.97 (s, 1H), 10.69 (s, 1H).

Example 32

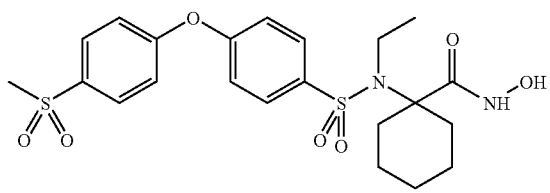

1-[Ethyl({4-[4-(methylsulfonyl)phenoxy]phenyl}sulfonyl)amino]-N-hydroxycyclohexanecarboxamide $^1$H-NMR (DMSO-D$_6$) δ1.12 (m, 1H), 1.15 (t, J=6.8 Hz, 3H), 1.35 (m, 2H), 1.50 (m, 3H), 1.68 (m, 2H), 2.28 (m, 2H), 3.23 (s, 3H), 3.32 (q, J=6.8 Hz, 2H), 7.26 (m, 2H), 7.31 (m, 2H), 7.90 (m, 2H), 7.98 (m, 2H), 8.80 (s, 1H), 10.53 (s, 1H).

Example 33

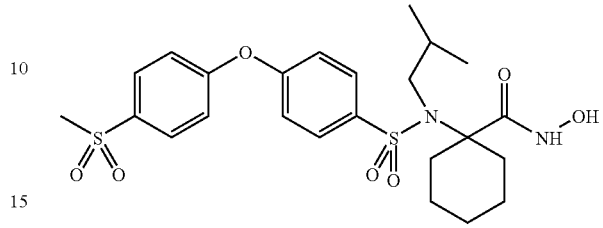

N-Hydroxy-1-[isobutyl({4-[4-(methylsulfonyl)phenoxy]phenyl}sulfonyl)amino]cyclohexanecarboxamide $^1$H-NMR (DMSO-D$_6$) δ0.82 (d, J=6.8 Hz, 1H), 1.04 (m, 1H), 1.27 (m, 2H), 1.50 (m, 3H), 1.66 (m, 2H), 1.98 (m, 1H), 2.26 (m, 2H), 3.18 (d, J=7.2 Hz, 2H), 3.23 (s, 3H), 7.42-7.31 (m, 4H), 7.86 (m, 2H), 7.98 (m, 2H), 8.82 (s, 1H), 10.57 (s, 1H).

Example 34

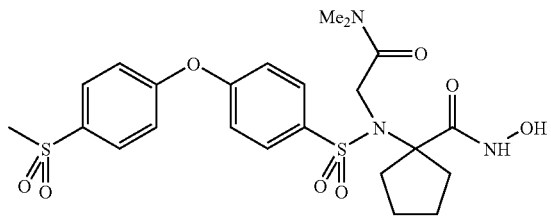

N-{1-[(Hydroxyamino)carbonyl]cyclopentyl}-N-({4-[4-(methylsulfonyl)phenoxy]phenyl}sulfonyl)-glycinedimethylamide $^1$H-NMR (DMSO-D$_6$) δ1.55 (m, 4H), 1.82 (m, 2H), 2.14 (m, 2H), 2.79 (s, 3H), 2.99 (s, 3H), 3.33 (s, 3H), 4.29 (s, 2H), 7.22-7.31 (m, 4H), 7.94-8.00 (m, 4H), 8.79 (s, 1H), 11.64 (s, 1H).

Example 35

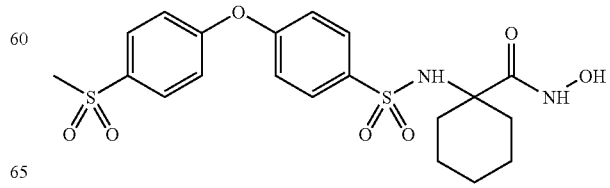

49

N-Hydroxy-1-[({4-[4-(methylsulfonyl)phenoxy]phenyl}sulfonyl)amino]cyclohexanecarboxamide $^1$H-NMR (DMSO-D$_6$) δ1.28 (m, 6H), 1.65 (m, 2H), 1.78 (m, 2H), 3.22 (s, 3H), 7.25-7.33 (m, 4H), 7.59 (s, 1H), 7.84 (m, 2H), 7.95 (m, 2H), 8.62 (s, 1H), 10.25 (s, 1H).

Example 36

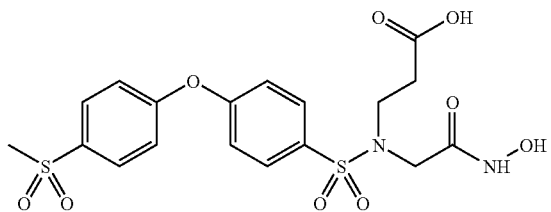

N-[2-(Hydroxyamino)-2-oxoethyl]-N-({4-[4-(methylsulfonyl)phenoxy]phenyl}sulfonyl)-β-alanine $^1$H-NMR (DMSO-D$_6$) β2.55 (t, J=7.6 Hz, 2H), 3.23 (s, 3H), 3.41 (t, J=7.6 Hz, 2H), 3.79 (s, 2H), 7.28-7.34 (m, 4H), 7.88 (m, 2H), 7.98 (m, 2H), 8.92 (s, 1H), 10.63 (s, 1H), 12.37 (brs, 1H).

Example 37

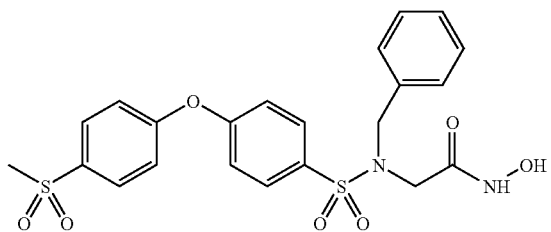

N$^{t2'}$-Benzyl-N$^{t1'}$-hydroxy-N$^{t2'}$-({4-[4-(methylsulfonyl)phenoxy]phenyl}sulfonyl)glycinamide $^1$H-NMR (DMSO-D$_6$) δ3.23 (s, 3H), 3.67 (s, 2H), 4.34 (s, 2H), 7.24-7.36 (m, 9H), 7.93 (m, 2H), 7.99 (m, 2H), 8.89 (s, 1H), 10.53 (s, 1H).

Example 38

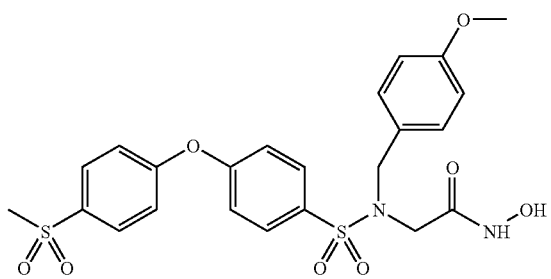

50

N$^{t1'}$-Hydroxy-N$^{t2'}$-(4-methoxybenzyl)-N$^{t2'}$-({4-[4-(methylsulfonyl)phenoxy]phenyl}sulfonyl)glycinamide $^1$H-NMR (DMSO-D$_6$) δ3.23 (s, 3H), 3.63 (s, 2H), 3.73 (s, 2H), 4.35 (s, 2H), 6.89 (m, 2H), 7.16 (m, 2H), 7.27 (m, 2H), 7.31 (m, 2H), 7.92 (m, 2H), 7.98 (m, 2H), 8.88 (s, 1H), 10.52 (s, 1H).

Example 39

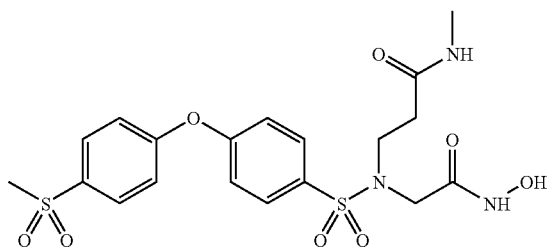

N$^{t3'}$-[2-(Hydroxyamino)-2-oxoethyl]-N$^{t1'}$-methyl-N$^{t3'}$-({4-[4-(methylsulfonyl)phenoxy]phenyl}sulfonyl)-β-alaninamide $^1$H-NMR (DMSO-D$_6$) β2.40 (t, J=7.6 Hz, 2H), 2.54 (d, J=4.4 Hz, 3H), 3.23 (s, 3H), 3.76 (s, 2H), 7.28-7.35 (m, 4H), 7.88 (m, 3H), 7.98 (m, 2H), 8.94 (s, 1H), 10.68 (s, 1H).

Example 40

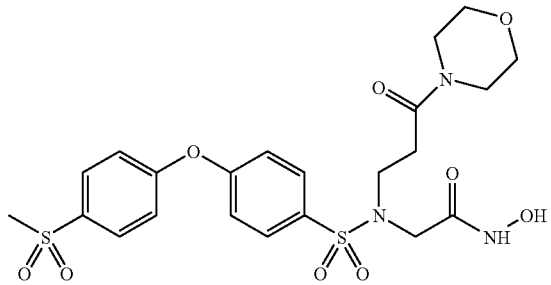

N-{1-[(Hydroxyamino)carbonyl]methyl}-N-({4-[4-(methylsulfonyl)phenoxy]phenyl}sulfonyl)-β-alaninemorpholinoamide $^1$H-NMR (DMSO-D$_6$) δ2.66 (m, 2H), 3.23 (s, 3H), 3.38 (m, 6H), 3.51-3.58 (m, 4H), 3.81 (s, 2H), 7.28-7.43 (m, 4H), 7.88 (m, 2H), 7.98 (m, 2H), 8.93 (s, 1H), 10.66 (s, 1H).

Example 41

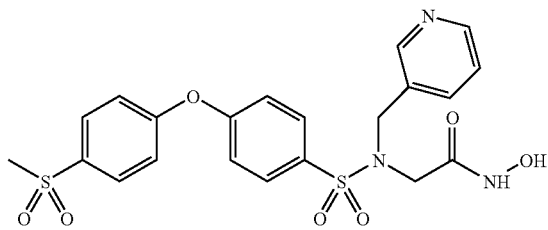

N'¹'-Hydroxy-N'²'-({4-[4-(methylsulfonyl)phenoxy]phenyl}sulfonyl)-N'²'-(3-pyridinylmethyl)glycinamide ¹H-NMR (DMSO-D₆) δ3.23 (s, 3H), 3.73 (s, 2H), 4.45 (s, 2H), 7.26-7.36 (m, 4H), 7.37 (m, 1H), 7.71 (m, 1H), 7.89 (m, 2H), 7.99 (m, 2H), 8.43 (m, 1H), 7.49 (m, 1H), 8.92 (s, 1H), 10.59 (s, 1H).

Example 42

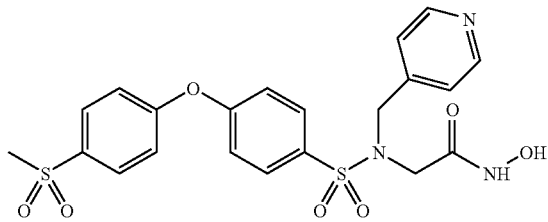

N'¹'-Hydroxy-N'²'-({4-[4-(methylsulfonyl)phenoxy]phenyl}sulfonyl)-N'²'-(4-pyridinylmethyl)glycinamide ¹H-NMR (DMSO-D₆) δ3.23 (s,3H), 4.04 (s, 2H), 4.685 (s, 2H), 7.29-7.35 (m, 4H), 7.85 (br, 2H), 7.94-8.01 (m, 4H), 7.72-8.79 (br, 3H), 12.30 (s, 1H).

Example 43

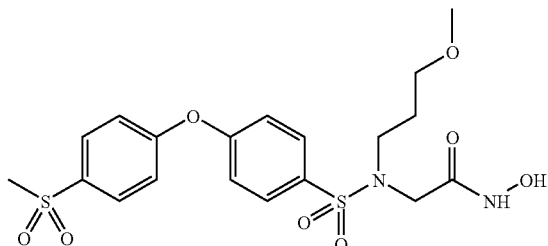

N¹-Hydroxy-N²-(3-methoxypropyl)-N²-({4-[4-(methylsulfonyl)phenoxy]phenyl}sulfonyl)glycinamide ¹H-NMR (DMSO-D₆) δ1.70 (m, 4H), 3.16-3.21 (m, 5H), 3.23 (s, 3H), 3.29 (t, J=6.0 Hz, 2H), 3.73 (s, 2H), 7.27-7.34 (m, 4H), 7.88 (m, 2H), 7.98 (m, 2H), 8.93 (s, 1H), 10.62 (s, 1H).

Example 44

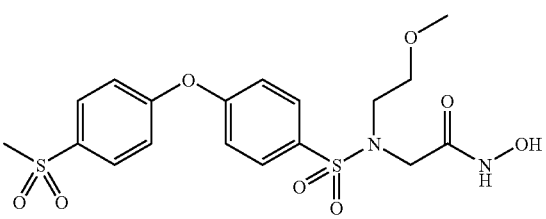

N¹-Hydroxy-N²-(2-methoxyethyl)-N²-({4-[4-(methylsulfonyl)phenoxy]phenyl}sulfonyl)glycinamide ¹H-NMR (DMSO-D₆) δ3.19 (s, 3H), 3.23 (s, 3H), 3.36 (t=6.0 Hz, 2H), 3.45 (t, J=6.0 Hz,2H), 3.80 (s, 2H), 7.23-7.33 (m, 4H), 7.89 (m, 2H), 7.98 (m, 2H), 8.91 (s, 1H), 10.53 (s, 1H).

Example 45

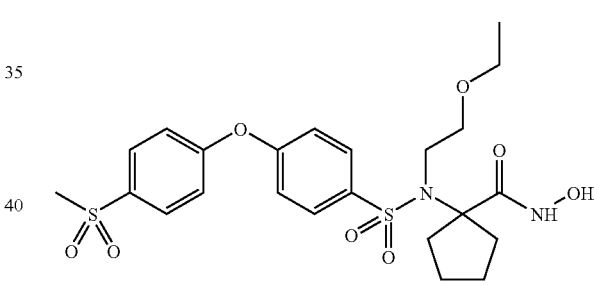

1-[(2-Ethoxyethyl)({4-[4-(methylsulfonyl)phenoxy]phenyl}sulfonyl)amino]-N-hydroxycyclopentanecarboxamide ¹H-NMR (DMSO-D₆) δ1.09 (t, J=6.8 Hz, 3H), 1.53 (m, 4H), 1.95 (m, 2H), 2.24 (m, 2H), 3.23 (s, 3H), 3.39-3.49 (m, 4H), 3.52 (m, 2H), 3.81 (m, 2H), 7.25-7.34 (m, 4H), 7.90 (m, 2H), 7.98 (m, 2H), 8.81 (s, 1H), 10.32 (s, 1H).

Example 46

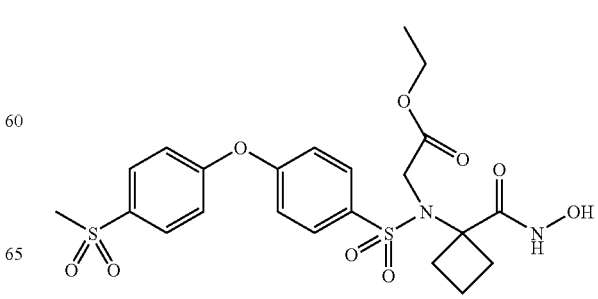

Ethyl N-{1-[(hydroxyamino)carbonyl]cyclobutyl}-N-({4-[4-(methylsulfonyl)phenoxy]phenyl}sulfonyl)glycinate ¹H-NMR (DMSO-D₆) δ1.18 (t, J=7.2 Hz, 3H), 1.69 (m, 2H), 2.36 (m, 4H), 3.23 (s, 3H), 4.10(q, J=7.2 Hz, 2H), 4.17 (s, 2H), 7.25 (m, 2H), 7.31 (m, 4H), 7.84 (m, 2H), 7.97 (m, 2H), 8.88 (s, 1H), 10.64 (s, 1H).

Example 47

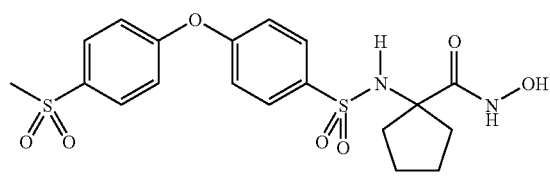

N-Hydroxy-1-[({4-[4-(methylsulfonyl)phenoxy]phenyl}sulfonyl)amino]cyclopentanecarboxamide ¹H-NMR (DMSO-D₆) δ1.27 (m, 2H), 1.41 (m, 2H), 1.79 (m, 4H), 3.17 (s, 3H), 7.19-7.22 (m, 4H), 7.76 (br, 1H), 7.79 (m, 2H), 7.89 (m, 2H), 8.64 (s, 1H), 10.21 (s, 1H).

Example 48

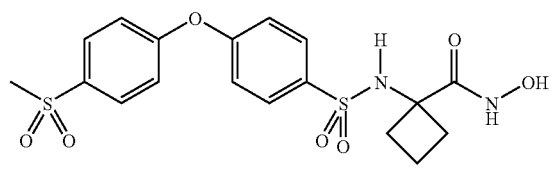

N-Hydroxy-1-[({4-[4-(methylsulfonyl)phenoxy]phenyl}sulfonyl)amino]cyclobutanecarboxamide ¹H-NMR (DMSO-D₆) δ1.64 (m, 2H), 2.05 (m, 2H), 2.29 (m, 4H), 3.23 (s, 3H), 7.26-7.31 (m, 4H), 7.84 (m, 2H), 7.96 (m, 2H), 8.21 (br, 1H), 8.71 (br, 1H), 10.41 (s, 1H).

Example 49

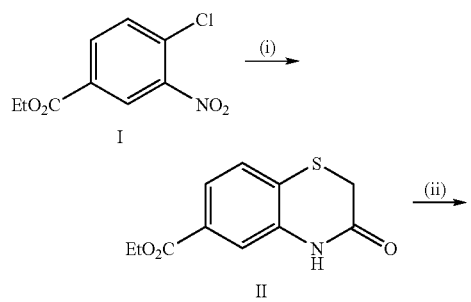

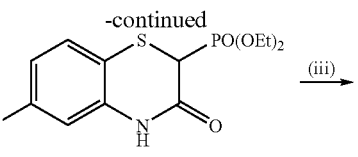

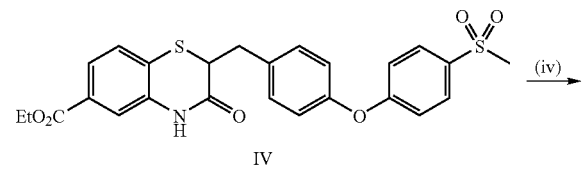

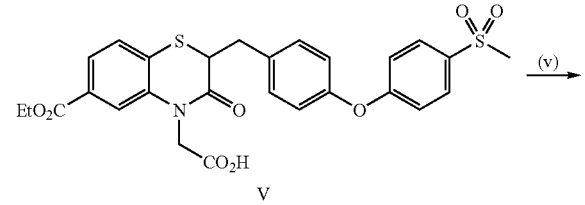

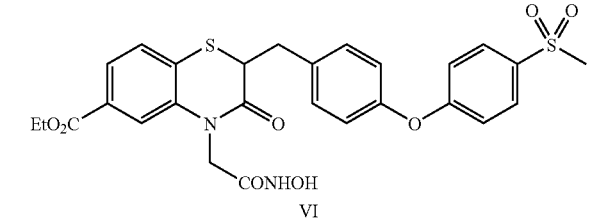

Step (i):

To a mixture of thioglycolic acid (10.8 g), potassium carbonate (65 g) and dimethylformamide (300 ml) was added ethyl 4-chloro-3-nitrobenzoate (28.1 g) in DMF (100 ml), and the mixture was heated at 80° C. After stirring for 6 hours, the solid was filtered off and the filtrate was concentrated under reduced pressure. To the residue were added diethyl ether (50 ml) and water (100 ml) to filter a yellow solid. The solid was acidified with 4N-hydrochloric acid and extracted with ethyl acetate. The organic layer was dried over sodium sulfate and concentrated. Thus obtained product (27.63 g) was served as the following reaction without further purification.

To the above product (12.9 g) in tetrahydrofuran (300 ml) was added 10% Pd/C (13 g) and the mixture was vigorously stirred for 9 hours at room temperature under hydrogen atmosphere. Catalyst was filtered off and the filtrate was concentrated under reduced pressure. To the crude product (9.4 g) and N-hydroxybenztriazole (HOBt) (5.9 g) in dimethylformamide (200 ml) was added 1-ethyl-3-(3-dimethylaminopropyl)carbodiimide.hydrochloride (EDC.HCl) (7.4 g). The mixture was stirred for overnight at room temperature and concentrated under reduced pressure. The residue was dissolved in ethyl acetate, washed successively with 1N-hydrochloric acid and an aqueous 5% sodium carbonate solution and brine. The organic layer was dried over sodium sulfate and concentrated. The residue was recrystallized from diethyl ether and hexane to give compound II (8.5 g) as a white solid.

Step (ii):

To compound II (8.43 g) in dichloromethane (80 ml) was dropped sulfuryl chloride (4.8 g) and the mixture was stirred for 6 hours at room temperature. The mixture was condensed under reduced pressure and the residue was recrystallized from chloroform and hexane to give a white solid (8.8 g).

A mixture of thus obtained a white solid (8.7 g) and triethylphosphite (11.7 g) was stirred for 10 hours at 120° C. After removal the solvent under reduced pressure, the residue was recrystallized from tetrahydrofuran and diethyl ether to give compound III (10.5 g) as a pale yellow solid.

Step (iii):

To 4-(4-methylsulfonylphenoxy)benzaldehyde (1.5 g) and compound III (1.9 g) in tetrahydrofuran(80 ml) under nitrogen atmosphere under ice cooling was added 60% sodium hydride (0.5 g). After 4 hours the reaction mixture was concentrated under reduced pressure. After ethyl acetate (10 ml) and hexane (50 ml) were added to the residue, 1N-hydrochloric acid (20 ml) and water (80 ml) were added thereto in that order, followed by hexane (100 ml). The mixture was stirred for 20 minutes at room temperature. The solid product was collected by filtration and dried under reduced pressure to give a yellow solid (2.6 g).

To the yellow solid (2.6 g) were added dioxane (300 ml), methanol (50 ml), tetrahydrofuran (80 ml) and 5% Pd/C (2.6 g). The mixture was stirred for 6 hours under hydrogen atmosphere under normal pressure at room temperature. After removal of catalyst by filtration, the filtrate was concentrated under reduced pressure to give compound IV (2.3 g) as a white solid.

Step (iv):

To compound IV (2.3 g) in dimethylformamide (20 ml) under nitrogen atmosphere under ice cooling was added 60% sodium hydride (0.2 g) and then, the mixture was stirred at room temperature for 1 hour. Then under ice cooling, thereto was dropped t-butyl bromoacetate (1 ml). After 6 hours, the mixture was poured into ammonium chloride solution, and extracted with ethyl acetate. The organic layer was dried over sodium sulfate, and concentrated under reduced pressure. The residue was treated with silica gel column chromatography (hexane/ethyl acetate=3/1 to 7/3) to give an addition compound (2.4 g). To this compound were added dichloromethane (15 ml) and 1,2-ethanedithiol (0.8 ml) and to the mixture was added at 0° C. trifluoroacetic acid (20 ml). After 3 hours, the solution was concentrated under reduced pressure. Thereto were added diisopropyl ether (20 ml) and hexane (200 ml), and the resulting solid was collected by filtration and dried over to give compound V (2.4 g).

Step (v):

To compound V (2.4 g) and N-methylmorpholine (0.6 ml) in tetrahydrofuran (50 ml), was dropped at −15° C. under nitrogen atmosphere isopropylchloroformate (0.5 ml). After 20 minutes, O-trimethylsilylhydroxylamine (0.7 ml) was dropped thereto. The mixture was gradually raised to room temperature and extracted with 1N-hydrochloric acid and ethyl acetate. The organic layer was dried over sodium sulfate and concentrated under reduced pressure. The residue was treated with silica gel column chromatography (hexane/ethyl acetate=1/1 to 1/4) give compound VI (1.9 g).

$^1$H-NMR (CDCl$_3$) δ1.41 (t, J=7.2 Hz, 3H), 2.88 (m, 1H), 3.06 (m, 1H), 3.20 (m, 1H), 3.75 (m, 1H), 4.40 (q, J=7.2 Hz, 2H), 4.50 (d, J=16 Hz, 1H), 4.74 (d, J=16 Hz, 1H), 7.00 (m, 2H), 7.08 (m, 1H), 7.18 (m, 2H), 7.45 (d, J=8.0 Hz, 1H), 7.78 (d, J=8.0 Hz, 1H), 7.89 (m, 2H) 8.09 (m, 1H), 9.03 (br, 1H)

Example 50

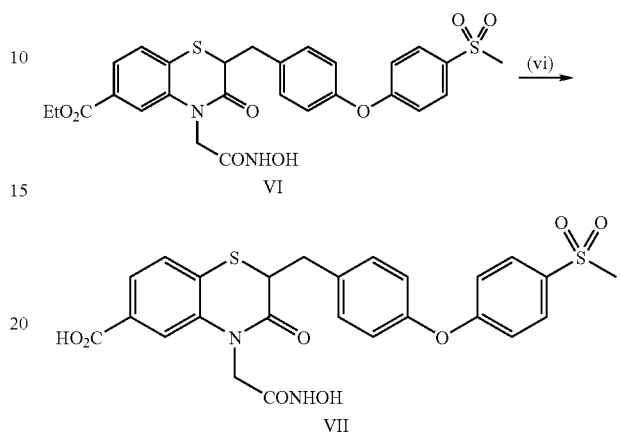

To compound (VI) (0.5 g) of Example 49 in tetrahydrofuran (8 ml) was at 0° C. dropped an aqueous 0.5N lithium hydroxide solution (3.5 ml). The mixture was gradually raised to room temperature and stirred for overnight. Thereto was added 3N-hydrochloric acid (70 ml) and the mixture was extracted with ethyl acetate (80 ml×2). The organic layer was dried over sodium sulfate and concentrated under reduced pressure. The residue was recrystallized from tetrahydrofuran and hexane to give compound VII (0.4 g).

$^1$H-NMR (DMSO-D$_6$) δ2.81 (m, 1H), 3.19 (S, 3H), 3.40 (m, 1H), 4.02 (m, 1H), 4.52+4.73+4.95 (2H, NCH2CO), 7.06 (m, 2H), 7.13(m, 2H), 7.33 (m, 2H), 7.51 (d, J=8 Hz, 1H), 7.62 (dd, J=1.6, 8 Hz, 1H), 7.67 (d, J=1.6 Hz, 1H), 7.91 (m, 2H), 9.05+9.46 (s, 1H), 10.41+10.85 (s, 1H), 13.19 (br, 1H)

Compounds of Example 51-58 listed in the below table can be prepared by the above methods (Processes 2 and 4).

TABLE 1

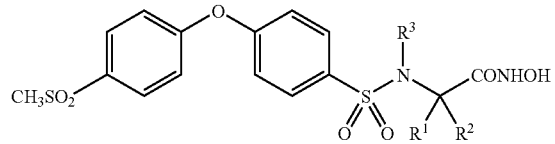

| Example | R$^1$ | R$^2$ | R$^3$ |
|---|---|---|---|
| 51 | —(CH$_2$)$_4$— | | CH$_2$CH$_2$CH$_3$ |
| 52 | —(CH$_2$)$_4$— | | CH(CH$_3$)CH$_2$CH$_3$ |
| 53 | —(CH$_2$)$_3$— | | CH$_2$CH$_2$CH$_3$ |
| 54 | —(CH$_2$)$_3$— | | CH(CH$_3$)CH$_2$CH$_3$ |
| 55 | —(CH$_2$)$_3$— | | CH$_2$COOH |
| 56 | —(CH$_2$)$_2$—O—(CH$_2$)$_2$— | | CH$_2$CH$_2$CH$_3$ |
| 57 | —(CH$_2$)$_2$—O—(CH$_2$)$_2$— | | CH(CH$_3$)CH$_2$CH$_3$ |
| 58 | H | CH(CH$_3$)$_2$ | CH$_2$COOH |

Compounds of Example 59-80 listed in the below table can be prepared by the above method (Process 4).

TABLE 2

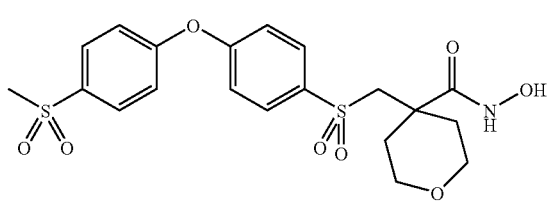

| Example | R¹ | R² | R³ |
|---|---|---|---|
| 59 | —(CH$_2$)$_4$— | | CH$_2$CH$_2$OCH(CH$_3$)$_2$ |
| 60 | —(CH$_2$)$_4$— | | CH$_2$CH$_2$CH$_2$OCH$_3$ |
| 61 | —(CH$_2$)$_4$— | | CH(CH$_3$)$_2$ |
| 62 | —(CH$_2$)$_4$— | | CH$_2$CH$_2$OCH$_3$ |
| 63 | —(CH$_2$)$_4$— | | CH$_2$CH$_2$CH$_2$OCH(CH$_3$)$_2$ |
| 64 | —(CH$_2$)$_3$— | | CH$_2$CH$_2$OCH$_2$CH$_3$ |
| 65 | —(CH$_2$)$_3$— | | CH$_2$CH$_2$OCH(CH$_3$)$_2$ |
| 66 | —(CH$_2$)$_3$— | | CH$_2$CH$_2$CH$_2$OCH$_3$ |
| 67 | —(CH$_2$)$_3$— | | CH(CH$_3$)$_2$ |
| 68 | —(CH$_2$)$_3$— | | CH$_2$CH$_2$OCH$_3$ |
| 69 | —(CH$_2$)$_3$— | | CH$_2$CH$_2$CH$_2$OCH(CH$_3$)$_2$ |
| 70 | —(CH$_2$)$_2$—O—(CH$_2$)$_2$— | | CH$_2$CH$_2$OCH$_2$CH$_3$ |
| 71 | —(CH$_2$)$_2$—O—(CH$_2$)$_2$— | | CH$_2$CH$_2$OCH(CH$_3$)$_2$ |
| 72 | —(CH$_2$)$_2$—O—(CH$_2$)$_2$— | | CH$_2$CH$_2$CH$_2$OCH$_3$ |
| 73 | —(CH$_2$)$_2$—O—(CH$_2$)$_2$— | | CH(CH$_3$)$_2$ |
| 74 | —(CH$_2$)$_2$—O—(CH$_2$)$_2$— | | CH$_2$CH$_2$OCH$_3$ |
| 75 | —(CH$_2$)$_2$—O—(CH$_2$)$_2$— | | CH$_2$CH$_2$CH$_2$OCH(CH$_3$)$_2$ |
| 76 | H | CH(CH$_3$)$_2$ | CH$_2$CH$_2$OCH$_2$CH$_3$ |
| 77 | H | CH(CH$_3$)$_2$ | CH$_2$CH$_2$OCH(CH$_3$)$_2$ |
| 78 | H | CH(CH$_3$)$_2$ | CH$_2$CH$_2$CH$_2$OCH$_3$ |
| 79 | H | CH(CH$_3$)$_2$ | CH$_2$CH$_2$OCH$_3$ |
| 80 | H | CH(CH$_3$)$_2$ | CH$_2$CH$_2$CH$_2$OCH(CH$_3$)$_2$ |

The following compound can be prepared by the above method (Process 8).

N-hydroxy-4-[({4-[4-(methylsulfonyl)phenoxy]phenyl}sulfonyl)methyl]tetrahydoro-2H-pyrane-4-carboxamide The following compound can be prepared by the above method (Process 9).

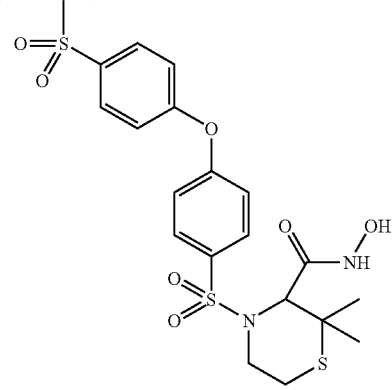

N-Hydroxy-2,2-dimethyl4-({4-[4-(methylsulfonyl)phenoxy]phenyl}sulfonyl)thiomorpholine-3-carboxamide The following compound can be prepared by the above method (Process 11).

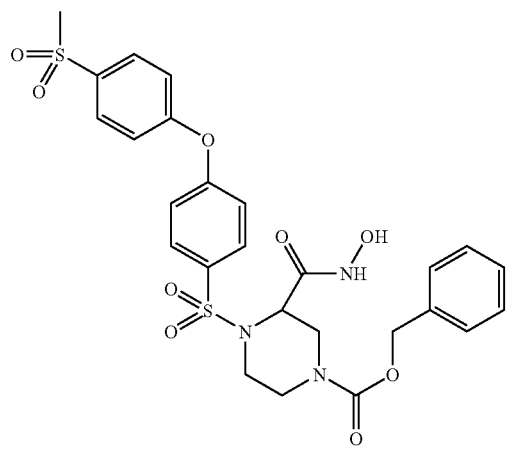

Benzyl 3-[(hydroxamino)carbonyl]-4-({4-[4-(methylsulfonyl)phenoxy]phenyl}sulfonyl)piperazine-1-carboxylate The following compound can be prepared by the above method (Process 11).

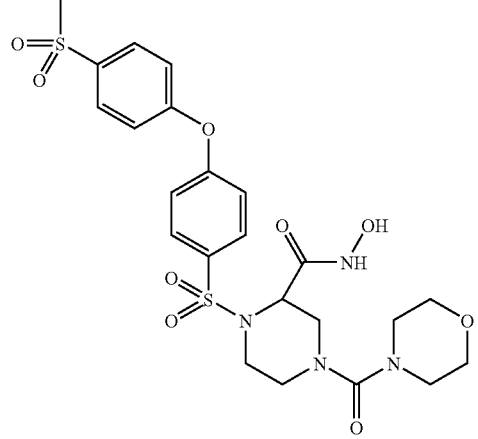

N-Hydroxy-1-({4-[4-(methylsulfonyl)phenoxy]phenyl}sulfonyl)-4-(morpholin-4-ylcarbonyl)piperazine-2-carboxamide.

The following compound can be prepared by the above method (Process 11).

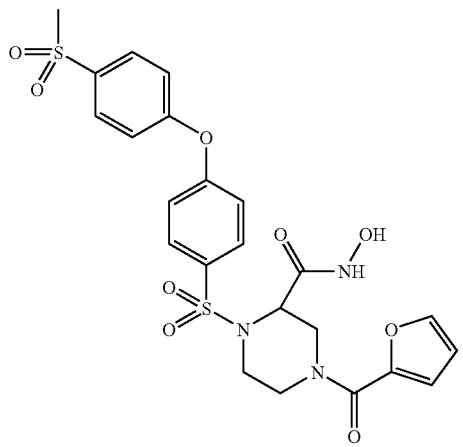

4-(2-Furoyl)-N-hydroxy-1-({4-[4-(methylsulfonyl)phenoxy]phenyl}sulfonyl)piperazine-2-carboxamide The following compound can be prepared by the above method (Process 10).

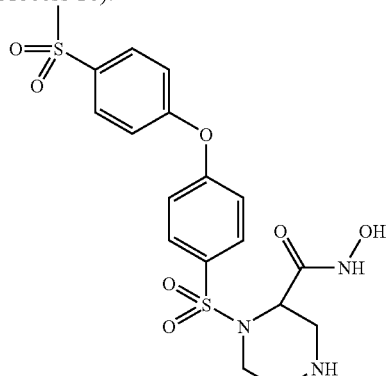

N-Hydroxy 1-({4-[4-(methylsulfonyl)phenoxy]phenyl}sulfonyl)piperazine-2-carboxamide.

The following compound can be prepared by the above method (Process 9).

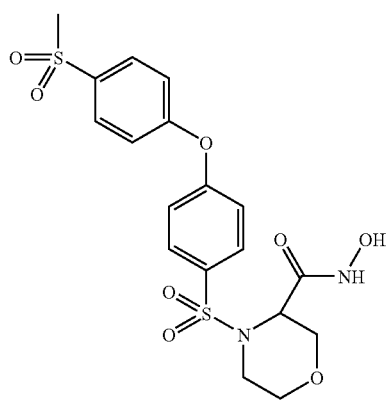

N-Hydroxy-4-({4-[4-(methylsulfonyl)phenoxy]phenyl}sulfonyl)morpholine-3-carboxamide.

The following compound can be prepared by the above method (Process 11).

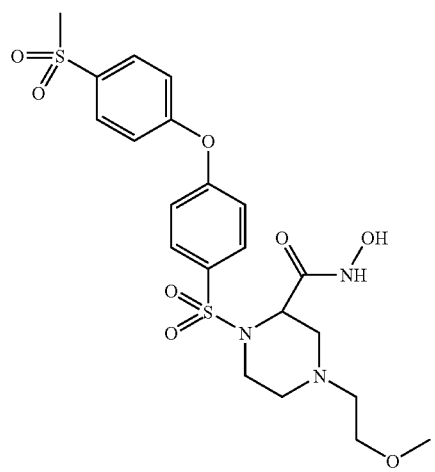

N-Hydroxy-4-(2-methoxyethyl)-1-({4-[4-(methylsulfonyl)phenoxy]phenyl}sulfonyl)piperazine-2-carboxamide.

The following compound can be prepared by the same manner as in Example 2.

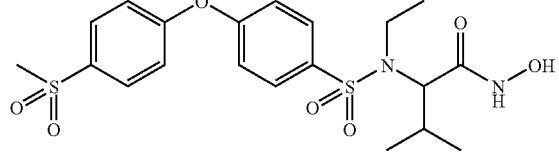

$N^2$-Ethyl-$N^1$-hydroxy-$N^2$-({4-[4-(methylsulfonyl)phenoxy]phenyl}sulfonyl)valinamide.

The following compound can be prepared by the same manner as in Example 2.

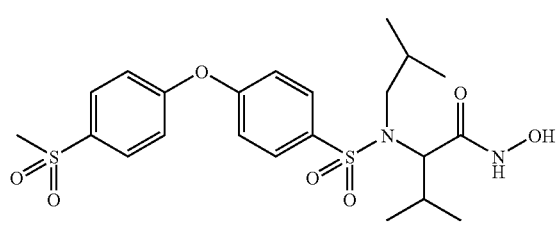

N¹-Hydroxy-N²-isobutyl-N²-({4-[4-(methylsulfonyl)phenoxy]phenyl}sulfonyl)valinamide.

The following compound can be prepared by the same manner as in Example 4.

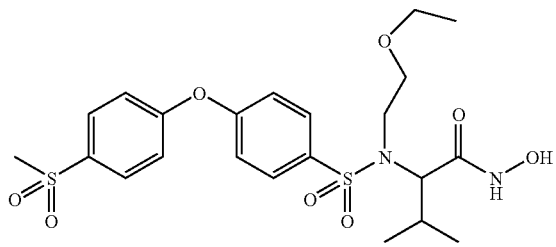

N¹-Hydroxy-N²-(2-ethoxyethyl)-N²-({4-[4-(methylsulfonyl)phenoxy]phenyl}sulfonyl)valinamide.

The following compound can be prepared by the same manner as in Example 4.

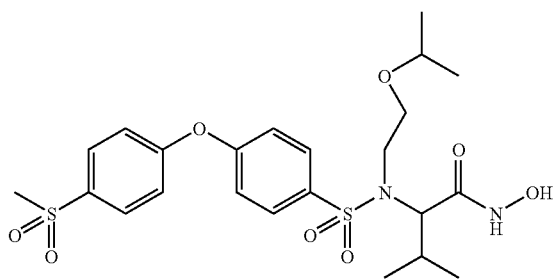

N¹-Hydroxy-N²-(2-isopropoxyethyl)-N²-({4-[4-(methylsulfonyl)phenoxy]phenyl}sulfonyl)valinamide.

The following compound can be prepared by the same manner as in Example 4.

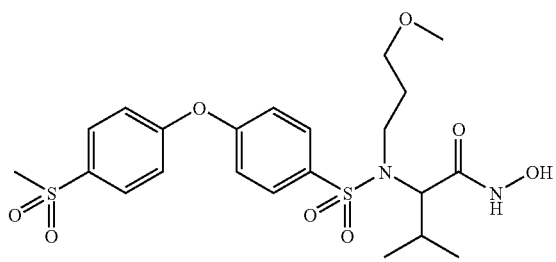

N¹-Hydroxy-N²-(2-methoxypropyl)-N²-({4-[4-(methylsulfonyl)phenoxy]phenyl}sulfonyl)valinamide.

Preparation 1

Process for Preparation of Tablets

Each ingredient is mixed, and if necessary after granulating, is compressed to prepare tables.

| Ingredient | Amount (mg/tab.) |
|---|---|
| Compound of Example 2 | 20 |
| Lactose | 70 |
| Corn starch | 17 |
| Lower substituted hydroxypropylcellulose | 8 |
| Hydroxypropylcellulose | 4 |
| Magnesium stearate | 1 |
| Total | 120 |

Preparation 2

Process for Preparation of Tablet

Each ingredient is mixed, and if necessary after granulating, is compressed to prepare tablets.

| Ingredient | Amount (mg/tab.) |
|---|---|
| Compound of Example 24 | 20 |
| D-mannitol | 60 |
| Calcium hydrogenphosphate | 25 |
| Calcium carmelose | 8 |
| Hydroxypropylmethylcellulose | 4 |
| Talc | 3 |
| Total | 120 |

Test

TTC buffer solution was attached to a MMP-2 enzyme assay kit, and the solution was made of 50 mM tris, 1 mM calcium chloride solution and 0.05% Triton X-100 solution, and was adjusted to pH 7.5.

ABTS was attached to a MMP-2 enzyme assay kit.

Streptavidin-POD means streptoavidin-peroxydase.

Tris-HCL means 2-amino-2-hydroxymethyl-1,3-propanediol hydrochloride.

0.05% Brij 35 means 0.05% solution of polyoxyethylene-dodecylethane.

2.5 mM 4-Aminophenyl mercury acetate (AMPA) solution was a solution which was made of 4-aminophenyl mercury acetate (35 mg), 0.1N aqueous sodium hydroxide solution (10 ml) and TTC buffer solution (30 ml), and was adjusted to pH 7.0 to 7.5.

NaN₃ means sodium azide.

MOCAc-Pro-Leu-Gly-Leu-A2pr(DNP)-Ala-Arg-NH₂ means (7-methoxycoumalin-4-yl)-Pro-Leu-Gly-Leu-L-[N-(2,4-dinitrophenyl)-L-2,3-diaminopropionyl]-Ala-Arg-NH₂ (Peptide Lab.).

DMSO means dimethyl sulfoxide.

MOPS means 3-(N-morpholino)propanesulfonic acid.

Test 1 Test on MMP-3 Inhibiting Activity

MMP-3 Activation

C-terminal truncated cDNA in which the cDNA encodes human prostromelysin, was subcloned (proMMP-3, cDNA sequence in Nature, 348, 699-704 (1990)), was expressed in *E. coli* and then, the expressed protein was purified in accordance with the method described in Biochemistry 30, 6476-6483 (1991). proMMP-3 activation was carried out by treating with 1 mM 4-aminophenyl mercuric acetate for 60 minutes at 37° C.

Inhibition Test Method

Enzyme activity test was conducted by the method of C. G. Knight (FEBS Lett., 296(3), 263-266 (1992)).

A mixture of activated MMP-3 (20 nM, 10 µl), buffer solution (70 µl, pH 7.5 solution containing 100 mM Tris-HCl solution, 10 mM calcium chloride solution, 100 mM sodium chloride solution and 0.05% Brij-35 solution), MOCAc-Pro-Leu-Gly-Leu-A2pr(DNP)-Ala-Arg-NH$_2$ in 0.1% DMSO solution (100 µM, 10 µl) and a test compound in DMSO solution was incubated for 1.5 hours at 37° C. The mixture was put on a 96 well-plate (100 µl/well) and the plate was cultured at 37° C. The enzyme activity in the presence of the compound was measured based on fluorescence intensity (λex 320 nm, λem 405 nm), and IC$_{50}$ was calculated.

Test 2 Test on MMP-13 Inhibition Activity

MMP-13 Activation

In order to subcloning C-terminal truncated cDNA in which the cDNA encodes procollagenase-3 (proMMP-13) (J. Biol. Chem., 269(24), 16766-16773 (1994)), two synthesized oligonucleotide primer fragments:
(5'-GGAATTC CATATGCTGCCGCTGCCGAGTGGTGGTGATGA AGATG-3' and 5'-TTT GGATCCTTAGCCGTACAGGCTTTGAATACCTT GTACATCGTCATCAGG-3': In former the sequence for specific NdeI site (under line) including first methionine is included, and in latter terminal codon and BamHI site (under lined) are included.) were used with human cartilage cell cDNA library for PCR. Due to these primers and Pfu DNA polymelase (STRATAGENE) for PCR, there was obtained a fragment of 767 bp encoding original 84 amino acids of complete MMP-13 and encoding 164 amino acids. The said fragment was cut out with digestion by NdeI and BamHI, and the fragment was annealed to NdeI site and BamHI site of pET11a (STRATAGENE). The recombinant plasmid was transformed into E. coli BL21 (DE3) and the bacteria were cultivated. The crude cell extract was prepared according to the method of Biochemistry. The said extract was dialyzed with 20 mM Tris-HCl (pH 7.2)/5 mM CaCl$_2$/0.02% NaN$_3$ solution, treated with SP-sepharose HP column (1.6×10 cm, Amasham-Pharmacia biotec), and the eluting was carried out by liner gradient from 0 to 0.3 m of sodium chloride solution (50 ml) (partially purified proMMP-13 was eluted at about 0.2M.) The eluted fraction was dialyzed with 20 mM Tris-HCl (pH 7.9)/5 mM CaCl$_2$/200 mM (NH$_4$)$_2$SO$_4$/0.02% NaN$_3$ solution, treated with phenylsepharose HP column (1.6×5 cm, Amersham-Pharmacia biotec), and the eluting was carried out by liner gradient from 0.2M to 0M sulfuric acid ammonium solution (purified proMMP-13 was eluted at about 50 mM.). The eluted fraction was concentrated by YM-5 ultrafilter membrane, and activated by 4-aminophenyl mercuric acetate. Activated MMP-13 was treated with gel filtration chromatography in accordance with the method of Biochemistry to be separated from propeptide.

Inhibiting Test Method

Enzyme activity test was carried out by the method of G. Knight (FEBS Lett., 296(3), 263-266 (1992)).

A mixture of activated MMP-13 (20 nM, 10 µl), buffer solution (70 µl, pH 7.5 solution containing 100 mM Tris-HCl solution, 10 mM calcium chloride solution, 100 mM sodium chloride solution and 0.05% Briji-35 solution), MOCAc-Pro-Leu-Gly-Leu-A2pr(DNP)-Ala-Arg-NH$_2$ in 0.1% DMSO solution (100 µM, 10 µl) and a test compound in DMSO solution was incubated for 1.5 hours at 37° C. The mixture was put on a 96 well-plate (100 µl/wel), and the plate was incubated at 37° C. The enzyme activity in the presence of the compound was measured based on fluorescence intensity (λex 320 nm, λem 405 nm), and IC$_{50}$ was calculated.

Test 3 MMP-2 Inhibition Activity Test

MMP-2 enzyme assay kit (Gelatinase Activity Assay, Roche.Diagonistics) was used.

MMP-2 Activation

A mixture of 1.2U human MMP-2 (20 µl, Boeringer Manheim 30U freezed dry product), TTC buffer (980 µl) and 2.5 mM 4-aminophenyl mercuric acetate solution (144 µl) was incubated at 37° C. for 30 minutes and then it was preserved under ice cooling until use.

Inhibition Test Method

A mixture of DMSO solution (2 µl) containing a definite concentration of the compound, biotin labeled gelatin (188 µl) and activated MMP-2 solution (10 µl) was put on a 96 well-assay plate (protein nonabsorbance type), well agitated and incubated at 37° C. for 1 hour. This solution was transferred to a Streptavidin-coating plate and agitated at 15° C, to 30° C. for 30 minutes. And then the solution was washed with TTC buffer solution (200 µl) three times. Thereto was added Streptavidin-POD (200 µl) and the mixture was agitated at 15° C. to 25° C. for 60 minutes, followed by washing with TTC buffer (200 µl) three times. Then, ABTS solution (200 µl) was added thereto and after standing at room temperature for 40 minutes, furuorescence intensity was measure at 405 nm and IC$_{50}$ was calculated.

In case of the above test, a control and a blank were prepared when the well was prepared as mentioned below. DMSO (2 µl) was used as a control instead of a sample solution. In the case of a blank, DMSO (2 µl) instead of the sample solution and the solution (10 µl) prepared in the same manner as preparation of activated MMP-2 solution but without adding 1.2U human MMP-2, instead of activated MMP-2 solution (10 µl), were used.

Test 4 MMP-9 Inhibiting Activity Test

MMP-9 Activation

A mixture of buffer solution (190 µl; pH 7.5 solution containing 50 mM Tris-HCl solution, 0.5 m sodium chloride solution and 5 mM calcium chloride solution), human MMP-9 (10 µl) and trypsin solution (20 µl; trypsin 3 mg in activated buffer (5 ml)) was incubated at 37° C. for 10 minutes. Thereto was added aprotinine solution (20 µl; aprotinine (3 mg) in buffer (5 ml)) and the mixture was incubated at 37° C. for 10 minutes, followed by addition of buffer (2 ml). The mixture was preserved under cooling with ice until use.

Inhibition Test Method

A mixture of DMSO solution (2 µl) containing definite concentration of the compound, biotin labeled gelatin (188 µl) and activated MMP-9 solution (10 µl) was put on a 96 well-assay plate (protein nonabsorbance type), well agitated, and incubated at 37° C. for 1 hour. This solution was transferred to Streptavidin-coating plate, and agitated at 15° C. to 30° C. for 30 minutes. And then the solution was washed with TTC buffer solution (200 µl) three times. Thereto was added Streptavidin-POD (200 µl) and the mixture was agitated at 15° C. to 25° C. for 60 minutes, followed by washing with TTC buffer (200 µl) three times. Then, ABTS solution (200 µl) was added thereto and after standing at room temperature for 40 minutes, furuorescence intensity was measured at 405 nm and IC$_{50}$ was calculated.

In case of the above test, DMSO (2 μl) was used as a control instead of a sample solution. In the case of a blank, DMSO (2 μl) instead of the sample solution and the solution (10 μl) prepared in the same manner as preparation of activated MMP-2 solution but without adding 1.2 Uhuman MMP-9, instead of activated MMP-9 solution (10 μl), were used.

Test 5 MMP-14 (MTI-MMP) Inhibiting Activity Test

Human recombinant MTI-MMP used the product prepared by Biogenesis and supplied by Cosmobio (Nakarai Tesku).

Inhibition Test Method

An assay buffer solution (70 μl, pH 7.5 solution containing 0.1M Tris-HCl solution, 0.1M calcium chloride solution, 10 mM sodium chloride solution and 0.05% Brij-35 solution), 0.1 w/w % a compound in DMSO (10 μl), MMP substrate solution (MOCAc-Pro-Leu-Gly-Leu-A2pr(DNP)-Ala-Arg-$NH_2$ (Peptide Lab.) diluted with the assay buffer solution (50 μM, 10 μl)) and human recombinant MT1-MMP (0.4 pg/10 μl/well) were well agitated under stirring. The enzyme activity of the mixture was measured based on fluorescence intensity (λex 320 nm/λem 405 nm) by a fluorescence reader. After the mixture was incubated at 37° C. for 0.5 hour, the fluorescence intensity (λex 320 nm/λem 405 nm) was measured every hour, and $IC_{50}$ was calculated.

The inhibition value was calculated by withdrawing average value of blank well from fluorescence mean value of well in which MT1-MMP was added. As the blank was used the mixed solution prepared by adding assay buffer (10 μl) instead of MT1-MMP solution.

Test 6 MMP-1 Inhibition Activity Test

MMP-1 (stroma collagenase: EC3.4.24.7, human rheumatic synovium fibroblast, calbiochem cat. 444208) was activated with AMPA at 37° C. for 60 minutes. A test compound was preincubated with activated MMP-1 at 37° C. for 60 minutes in the reaction mixture containing 50 mM MOPS (pH 7.2), 10 mM aqueous calcium chloride solution, and 10 μM zinc chloride. Thereto was added 25 μM Mca-Pro-Leu-Dpa-Ala-Arg-$NH_2$, and the mixture was incubated at 37° C. for 120 minutes. The enzyme activity was measured by fluorescence intensity of Mca-Pro-Leu-Gly, and $IC_{50}$ was calculated.

The results on Tests 1~6 were shown in Table 3. In the table the value of inhibition activity means $IC_{50}$ (nM).

TABLE 3

| | MMP activity | | | | | |
|---|---|---|---|---|---|---|
| | MMP-13 inhibition activity value | MMP-3 inhibition activity value | MMP-14 inhibition activity value | MMP-2 inhibition activity value | MMP-9 inhibition activity value | MMP-1 inhibition activity value |
| Comp. Ex. 1 | 7.4 | 88 | 87.3 | >100 | >100 | NT |
| Ex. 2 | 5.7 | 21.2 | 3802 | <100 | 300 | 7210 |
| Ex. 3 | 0.5 | 4.8 | 172 | >100 | 1000 | NT |
| Ex. 5 | 1.3 | 15.4 | 105 | 100 | >100 | NT |
| Ex. 10 | 34.4 | 85.8 | >5000 | 2400 | 6800 | NT |
| Ex. 12 | 4 | 16 | 893.3 | <100 | <100 | >10000 |
| Ex. 13 | 10.8 | 13.5 | >5000 | 900 | 4700 | >10000 |
| Ex. 15 | 24.6 | 5.2 | >5000 | 300 | 700 | NT |
| Ex. 18 | 3.1 | 29.9 | 799 | 100 | 500 | 3300 |
| Ex. 22 | 1.9 | 26.6 | 668 | 1200 | 1400 | >10000 |
| Ex. 23 | 4.1 | 21.6 | >5000 | 2100 | 2300 | >10000 |
| Ex. 24 | 16.3 | 128.2 | >5000 | >10000 | >10000 | NT |
| Ex. 26 | 1.9 | 14.3 | 395.4 | 300 | >100 | 3900 |
| Ex. 27 | 21.3 | 89.4 | >5000 | >10000 | >10000 | NT |
| Ex. 31 | 11.2 | 59 | >5000 | 800 | 4900 | NT |
| Ex. 36 | 3.81 | 37.1 | 937.8 | 2900 | >100 | NT |
| Ex. 42 | 4.02 | 67.5 | >5000 | <100 | 4300 | >10000 |
| Ex. 43 | <0.5 | 8.5 | 82 | 1500 | 600 | NT |
| Ex. 44 | 0.5 | 2.7 | 343 | >100 | >10000 | NT |
| Ex. 45 | 0.6 | 1.5 | >1500 | >100 | >100 | 4960 |
| Ex. 46 | 10.5 | 11.6 | >1500 | >100 | >100 | NT |
| Ex. 48 | 6.9 | 35.9 | >1500 | >100 | >100 | NT |
| Ex. 50 | 3 | 38 | >1000 | >100 | 244 | NT |

NT: not tested

A compound of comparative example 1 shown in the following structure was prepared in the same manner as in examples 49 and 50.

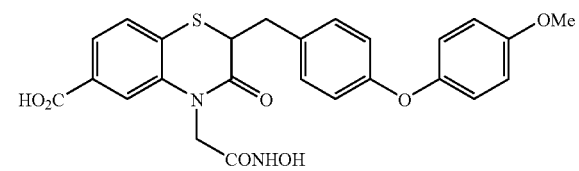

Test 7 Adjuvant Arthritis (in vivo)

For this test Lewis male rats were used. The suspension prepared by suspending *Mycobacterium butyricum* in liquid paraffin in concentration of 0.5% was subcutaneously injected in a right hind paw. Ten days later the rats in which the definite secondary inflammation on a left hind paw wasobserved were selected, and to the rats the compound (Example 2) suspended in 0.5% methyl cellulose was orally administered for twelve successive days once a day. Five hours later after finishing administration the volume of the hind paws was compared with the volume when the administration was initiated, and the inhibition activity of edema was evaluated based on this difference.

The result was shown in Table 4.

TABLE 4

| Compound | Amount (per os, mg/kg) | Rat (number) | Increase of edema(ml) | |
|---|---|---|---|---|
| | | | Injected limb | Non injected limb |
| Control | — | 10 | −0.24 ± 0.45 | 1.07 ± 0.31 |
| Example2 | 50 | 10 | −1.06 ± 0.47** | 0.74 ± 0.16** |

**P < 0.01(t test)

Test 8 Rat Meniscectomy Model Test (in vivo)

For this test male rats (6 weeks old SD (IGS)) were used. A meniscus of joint of a right hind limb was partially removed. Compound of Example 2 was orally administered for 3 weeks once a day in the amount of 50 mg/kg. The tissue speciman of the joint was prepared, and stained with safranin O/first green, and the degeneration of cartilage was evaluated. The degree of the degeneration of cartilage in the test compound group was calculated as 100% of the degree of that in the injured group. Cartilage degeneration rate was 33% (*; p<0.05, Steel-test)

---

The invention claimed is:

1. A hydroxamic acid compound represented by the following formula (1),

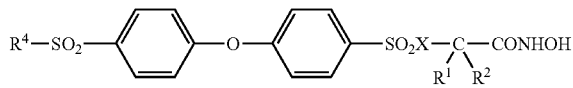

(1)

wherein $R^1$ and $R^2$ are each independently hydrogen atom, optionally substituted lower alkyl group, or lower haloalkyl group, or $R^1$ and $R^2$ are bound together to form C2~7 straight alkylene group, or a group represented by a formula, —$(CH_2)m$-Y—$(CH_2)q$- (wherein Y is —O—, —$NR^5$—, —S—, —SO—, or —$SO_2$—, m and q are each independently an integer of 1 to 5, and the total of m and q are 2~6, and $R^5$ is hydrogen atom, optionally substituted lower alkyl group, optionally substituted lower alkylcarbonyl group, optionally substituted lower alkoxycarbonyl group, optionally substituted lower alkylsulfonyl group, optionally substituted sulfamoyl group or optionally substituted carbamoyl group), X is methylene group or $NR^3$ (wherein $R^3$ is hydrogen atom, or optionally substituted lower alkyl group), and $R^4$ is C1~4 lower alkyl group, wherein a substituent of the lower alkyl groups in $R^1$ and $R^2$ is selected from the group consisting of halogen atom, hydroxy group, cyano group, lower alkoxy group, lower alkylthio group, lower alkylsulfinyl group, lower alkylsulfonyl group, lower cycloalkyl group, optionally substituted aryl group, optionally substituted aryloxy group, optionally substituted arylthio group, optionally substituted arylsulfonyl group, and —$NR^{17}R^{18}$;

a substituent of the lower alkyl group in $R^3$ is selected from the group consisting of carboxy group, hydroxy group, lower haloalkyl group, lower haloalkoxy group, cyano group, lower alkylcarbonyl group, lower alkylcarbonyloxy group, lower alkoxycarbonyl group, —$CONR^{11}R^{12}$, —$SO_2NR^{11}R^{12}$, —$NHCONR^{11}R^{12}$, —$NR^{13}COR^{14}$, —$NR^{13}SO_2R^{14}$, optionally substituted aryl group, optionally substituted aryloxy group, optionally substituted arylthio group, optionally substituted arylcarbonyl group, arylsulfonyl group, lower alkoxy group, lower alkylthio group, lower alkylsulfinyl group and lower alkylsulfonyl group, wherein each of above four groups is optionally substituted by a group selected from the group consisting of optionally substituted aryl group, lower alkoxy group, carbamoyl group substituted by 1 or 2 lower alkyl groups, and carbamoyl group substituted by lower cycloalkyl group;

a substituent of the lower alkyl group, lower alkylcarbonyl group, lower alkoxycarbonyl group, or lower alkylsulfonyl group in $R^5$ is selected from the group consisting of lower alkoxy group, lower cycloalkoxy group and aryloxy group;

a substituent of the carbamoyl group and sulfamoyl group in $R^5$ is selected from the group consisting of lower alkyl group and lower alkoxy group;

$R^{11}$ and $R^{12}$ are each independently hydrogen atom, lower alkyl group, or lower alkyl group substituted by lower alkoxy group:

$R^{13}$ and $R^{14}$ are each independently hydrogen atom, or lower alkyl group;

$R^{17}$ is hydrogen atom or lower alkyl group, and $R^{18}$ is hydrogen atom, lower alkyl group, lower alkylcarbonyl group, lower alkoxycarbonyl group, or lower alkylsulfonyl group; and a substituent of the aryl group, aryloxy group, arylthio group, arylcarbonyl group, arylcarbamoyl group, and arylsulfonyl group is selected from the group consisting of halogen atom, cyano group, hydroxy group, carboxy group, lower haloalkyl group, lower haloalkoxy group, lower alkoxy group, lower alkylthio group, lower alkylsulfinyl group, lower alkylsulfonyl group, lower cycloalkyl group, lower alkoxycarbonyl group, —$CONR^{11}R^{12}$, —$SO_2NR^{11}R^{12}$ (wherein $R^{11}$ and $R^{12}$ are the same as defined above), —$NR^{13}COR^{14}$, —$NR^{13}SO_2R^{14}$ (wherein $R^{13}$ and $R^{14}$ are the same as defined above), —$NR^{17}R^{18}$ (wherein $R^{17}$ and $R^{18}$ are the same as defined above), and lower alkyl group optionally substituted by the group consisting of lower alkoxy group, lower alkylthio group, lower alkylsulfinyl group, lower alkylsulfonyl group, lower alkylcarbonyl group, lower alkoxycarbonyl group, lower alkylcarbonyloxy group, cyano group, carboxy group, hydroxy group, —$NR^{17}R^{18}$ (wherein $R^{17}$ and $R^{18}$ are the same as defined above), —$CONR^{11}R^{12}$, —$SO_2NR^{11}R^{12}$ (wherein $R^{11}$ and $R^{12}$ are the same as defined above), —$NR^{13}COR^{14}$, and —$NR^{13}SO_2R^{14}$ (wherein $R^{13}$ and $R^{14}$ are the same as defined above), or a pharmaceutically acceptable salt thereof.

2. The hydroxamic acid compound the formula (1) according to claim 1, wherein $R^1$ and $R^2$ are each independently hydrogen atom, or C1~3 lower alkyl group, or a pharmaceutically acceptable salt thereof.

3. The hydroxamic acid compound of the formula (1) according to claim 1, wherein $R^1$ and $R^2$ are bound together to form C3~5 alkylene group, or a pharmaceutically acceptable salt thereof.

4. The hydroxamic acid compound of the formula (1) according to claim 1, wherein $R^1$ and $R^2$ are bound together to form a group represented by the formula, —$(CH_2)m$-Y—$(CH_2)q$-, or a pharmaceutically acceptable salt thereof.

5. The hydroxamic acid compound of the formula (1) according to claim 4, wherein m and q are respectively 2 in the formula, —$(CH_2)m$-Y—$(CH_2)q$-, or a pharmaceutically acceptable salt thereof.

6. The hydroxamic acid compound of the formula (1) according to claim 1, wherein X is N—$R^3$, and the $R^3$ is hydrogen atom, C1~4 lower alkyl group, carboxy group, phenyl group (the said phenyl group may be substituted by lower alkyl group, lower alkoxy group or halogen atom), or C1~4 lower alkyl group substituted by lower alkoxycarbonyl group, lower alkoxy group or lower cycloalkoxy group, or a pharmaceutically acceptable salt thereof.

7. The hydroxamic acid compound of the formula (1) according to claim 1, wherein X is methylene group and $R^1$ and $R^2$ are bound together to form C3~4 straight alkylene group or —$(CH_2)_2$—O—$(CH_2)_2$—, or a pharmaceutically acceptable salt thereof.

8. The hydroxamic acid compound of the formula (1) according to claim 1, wherein $R^4$ is methyl group, or a pharmaceutically acceptable salt thereof.

9. The hydroxamic acid compound of the formula (1) according to claim 1, wherein $R^1$ and $R^2$ are each independently, hydrogen atom or C1~4 lower alkyl group, or $R^1$ and $R^2$ are bound together to form C3~4 straight alkylene group or a formula, —$(CH_2)_2$—Y—$(CH_2)_2$—, X is N—$R^3$, and the $R^3$ is hydrogen atom, C1~4 lower alkyl group, carboxy group, phenyl group (the said phenyl group may be substituted by lower alkyl group, lower alkoxy group or halogen atom), C1~4 lower alkyl group substituted by lower alkoxycarbonyl group, lower alkoxy group or cycloalkoxy group, and $R^4$ is methyl group, or a pharmaceutically acceptable salt thereof.

10. The hydroxamic acid compound of the formula (1) according to in claim 1, wherein $R^1$ and $R^2$ are bound together to form C3~4 straight alkylene group or —$(CH_2)_2$—O—$(CH_2)_2$—, X is N—$R^3$, and the $R^3$ is C1~4 lower alkyl group which may be substituted by C1~4 lower alkoxy group, or a pharmaceutically acceptable salt thereof.

11. A method for treating a disease related to promotion of MMP-3 and/or MMP-13, comprising administering the hydroxamic acid compound or pharmaceutically acceptable salt thereof according to claim 1 as an active ingredient to a patient in need thereof, wherein the disease related to promotion of MMP-3 and/or MMP-13 is arthritis.

12. The method according to claim 11, wherein the arthritis is osteoarthritis or rheumatoid arthritis.

13. A pharmaceutical composition comprising the hydroxamic acid compound or pharmaceutically acceptable salt thereof according to claim 1 and a pharmaceutically acceptable carrier.

\* \* \* \* \*

SEQUENCE LISTING

<160> NUMBER OF SEQ ID NOS: 3

<210> SEQ ID NO 1
<211> LENGTH: 44
<212> TYPE: DNA
<213> ORGANISM: Artificial Sequence
<220> FEATURE:
<223> OTHER INFORMATION: Primer for proMMP-13 sequence

<400> SEQUENCE: 1
ggaattccat atgctgccgc tgccgagtgg tggtgatgaa gatg         44

<210> SEQ ID NO 2
<211> LENGTH: 51
<212> TYPE: DNA
<213> ORGANISM: Artificial Sequence
<220> FEATURE:
<223> OTHER INFORMATION: Primer for proMMP-13 sequence

<400> SEQUENCE: 2
tttggatcct tagccgtaca ggctttgaat accttgtaca tcgtcatcag g      51

<210> SEQ ID NO 3
<211> LENGTH: 6
<212> TYPE: PRT
<213> ORGANISM: Artificial Sequence
<220> FEATURE:
<221> NAME/KEY: misc_feature
<222> LOCATION: (1)
<223> OTHER INFORMATION: Xaa=7-methoxycoumalin-4-yl-proline
<220> FEATURE:
<221> NAME/KEY: misc_feature
<222> LOCATION: (5)
<223> OTHER INFORMATION: Xaa=L-[N-(2,4-dinitrophenyl)-L-2,
      3-diaminopropionyl]-alanine.
<220> FEATURE:
<223> OTHER INFORMATION: Peptide for assaying MMP-3 activity

<400> SEQUENCE: 3

Xaa Leu Gly Leu Xaa Arg
 1               5